United States Patent
Al-Ali et al.

(10) Patent No.: US 8,801,613 B2
(45) Date of Patent: Aug. 12, 2014

(54) CALIBRATION FOR MULTI-STAGE PHYSIOLOGICAL MONITORS

(75) Inventors: Ammar Al-Ali, San Juan Capistrano, CA (US); Walter M. Weber, Laguna Hills, CA (US); Valery G. Telfort, Montreal (CA)

(73) Assignee: Masimo Corporation, Irvine, CA (US)

( * ) Notice: Subject to any disclaimer, the term of this patent is extended or adjusted under 35 U.S.C. 154(b) by 450 days.

(21) Appl. No.: 12/960,325

(22) Filed: Dec. 3, 2010

(65) Prior Publication Data
US 2011/0196211 A1    Aug. 11, 2011

Related U.S. Application Data

(60) Provisional application No. 61/266,984, filed on Dec. 4, 2009.

(51) Int. Cl.
*A61B 8/00* (2006.01)
*A61B 7/00* (2006.01)

(52) U.S. Cl.
USPC ............................ 600/438; 600/528; 600/586

(58) Field of Classification Search
USPC ......... 600/310, 322, 323, 344, 437, 438, 528, 600/586
See application file for complete search history.

(56) References Cited

U.S. PATENT DOCUMENTS

| | | | |
|---|---|---|---|
| 3,682,161 A | 8/1972 | Alibert | |
| 3,910,701 A | 10/1975 | Henderson et al. | |
| 3,951,230 A | 4/1976 | Littmann | |
| 3,998,550 A | 12/1976 | Konishi et al. | |
| 4,014,321 A | 3/1977 | March | |
| 4,051,522 A | 9/1977 | Healy et al. | |
| 4,127,749 A | 11/1978 | Atoji et al. | |
| 4,157,708 A | 6/1979 | Imura | |
| 4,167,331 A | 9/1979 | Nielsen | |
| 4,266,554 A | 5/1981 | Hamaguri | |

(Continued)

FOREIGN PATENT DOCUMENTS

| CA | 2262236 | 4/2008 |
|---|---|---|
| DE | 112010004682.4 | 12/2010 |

(Continued)

OTHER PUBLICATIONS

Eldor et al., "A device for monitoring ventilation during anaesthesia; the paratracheal audible respiratory monitor", Canadian Journal of Anaesthesia, 1990, vol. 9, No. 1, p. 95-98.

(Continued)

*Primary Examiner* — Eric Winakur
(74) *Attorney, Agent, or Firm* — Knobbe, Martens, Olson & Bear, LLP

(57) ABSTRACT

A physiological monitor is provided for determining a physiological parameter of a medical patient with a multi-stage sensor assembly. The monitor includes a signal processor configured to receive a signal indicative of a physiological parameter of a medical patient from a multi-stage sensor assembly. The multi-stage sensor assembly is configured to be attached to the physiological monitor and the medical patient. The monitor of certain embodiments also includes an information element query module configured to obtain calibration information from an information element provided in a plurality of stages of the multi-stage sensor assembly. In some embodiments, the signal processor is configured to determine the physiological parameter of the medical patient based upon said signal and said calibration information.

22 Claims, 22 Drawing Sheets

(56) References Cited

U.S. PATENT DOCUMENTS

| | | |
|---|---|---|
| 4,267,844 A | 5/1981 | Yamanishi |
| 4,326,143 A | 4/1982 | Guth et al. |
| 4,446,871 A | 5/1984 | Imura |
| 4,531,527 A | 7/1985 | Reinhold, Jr. et al. |
| 4,537,200 A | 8/1985 | Widrow |
| 4,578,613 A | 3/1986 | Dorogusker et al. |
| 4,586,513 A | 5/1986 | Hamaguri |
| 4,621,643 A | 11/1986 | New et al. |
| 4,634,917 A | 1/1987 | Dvorsky et al. |
| 4,653,498 A | 3/1987 | New, Jr. et al. |
| 4,655,225 A | 4/1987 | Dahne et al. |
| 4,685,464 A | 8/1987 | Goldberger et al. |
| 4,694,833 A | 9/1987 | Hamaguri |
| 4,695,955 A | 9/1987 | Faisandier |
| 4,700,708 A | 10/1987 | New et al. |
| 4,714,341 A | 12/1987 | Hamaguri et al. |
| 4,770,179 A | 9/1988 | New et al. |
| 4,773,422 A | 9/1988 | Isaacson et al. |
| 4,781,195 A | 11/1988 | Martin |
| 4,800,885 A | 1/1989 | Johnson |
| 4,805,623 A | 2/1989 | Jobsis |
| 4,827,943 A | 5/1989 | Bornn et al. |
| 4,832,484 A | 5/1989 | Aoyagi et al. |
| 4,846,183 A | 7/1989 | Martin |
| 4,854,328 A | 8/1989 | Pollack |
| 4,863,265 A | 9/1989 | Flower et al. |
| 4,867,571 A | 9/1989 | Frick et al. |
| 4,869,254 A | 9/1989 | Stone et al. |
| 4,884,809 A | 12/1989 | Rowan |
| 4,907,876 A | 3/1990 | Suzuki et al. |
| 4,911,167 A | 3/1990 | Corenman et al. |
| 4,924,876 A | 5/1990 | Cameron |
| 4,934,372 A | 6/1990 | Corenman et al. |
| 4,938,218 A | 7/1990 | Goodman et al. |
| 4,942,877 A | 7/1990 | Sakai et al. |
| 4,955,379 A | 9/1990 | Hall |
| 4,958,638 A | 9/1990 | Sharpe et al. |
| 4,960,126 A | 10/1990 | Conlon et al. |
| 4,960,128 A | 10/1990 | Gordon et al. |
| 4,964,010 A | 10/1990 | Miyasaka et al. |
| 4,964,408 A | 10/1990 | Hink et al. |
| 4,967,571 A | 11/1990 | Sporri |
| 4,975,581 A | 12/1990 | Robinson et al. |
| 4,982,738 A | 1/1991 | Griebel |
| 4,986,665 A | 1/1991 | Yamanishi et al. |
| 4,997,769 A | 3/1991 | Lundsgaard |
| 5,025,791 A | 6/1991 | Niwa |
| RE33,643 E | 7/1991 | Isaacson et al. |
| 5,027,825 A | 7/1991 | Phelps et al. |
| 5,028,787 A | 7/1991 | Rosenthal et al. |
| 5,033,032 A | 7/1991 | Houghtaling |
| 5,033,472 A | 7/1991 | Sato et al. |
| 5,035,247 A | 7/1991 | Heimann |
| 5,041,187 A | 8/1991 | Hink et al. |
| 5,054,495 A | 10/1991 | Uemura et al. |
| 5,058,588 A | 10/1991 | Kaestle et al. |
| 5,069,213 A | 12/1991 | Polczynski |
| 5,077,476 A | 12/1991 | Rosenthal |
| 5,078,136 A | 1/1992 | Stone et al. |
| 5,137,023 A | 8/1992 | Mendelson et al. |
| 5,143,078 A | 9/1992 | Mather et al. |
| 5,163,438 A | 11/1992 | Gordon et al. |
| 5,189,609 A | 2/1993 | Tivig et al. |
| 5,190,040 A | 3/1993 | Aoyagi |
| 5,209,230 A | 5/1993 | Swedlow et al. |
| 5,226,053 A | 7/1993 | Cho et al. |
| 5,246,002 A | 9/1993 | Prosser |
| 5,247,931 A | 9/1993 | Norwood |
| 5,259,381 A | 11/1993 | Chung |
| 5,267,562 A | 12/1993 | Ukawa et al. |
| 5,267,563 A | 12/1993 | Swedlow et al. |
| 5,278,627 A | 1/1994 | Aoyagi |
| 5,297,548 A | 3/1994 | Pologe |
| 5,313,940 A | 5/1994 | Fuse et al. |
| 5,319,355 A | 6/1994 | Russek |
| 5,331,549 A | 7/1994 | Crawford, Jr. |
| 5,335,659 A | 8/1994 | Pologe et al. |
| 5,337,744 A | 8/1994 | Branigan |
| 5,337,745 A | 8/1994 | Benaron |
| 5,341,805 A | 8/1994 | Stavridi et al. |
| 5,348,004 A | 9/1994 | Hollub |
| 5,351,685 A | 10/1994 | Potratz |
| 5,355,880 A | 10/1994 | Thomas et al. |
| 5,355,882 A | 10/1994 | Ukawa et al. |
| 5,361,758 A | 11/1994 | Hall et al. |
| 5,368,224 A | 11/1994 | Richardson et al. |
| D353,195 S | 12/1994 | Savage et al. |
| D353,196 S | 12/1994 | Savage et al. |
| 5,372,136 A | 12/1994 | Steuer et al. |
| 5,377,302 A | 12/1994 | Tsiang |
| 5,377,676 A | 1/1995 | Vari et al. |
| 5,385,143 A | 1/1995 | Aoyagi |
| 5,387,122 A | 2/1995 | Goldberger et al. |
| 5,392,777 A | 2/1995 | Swedlow et al. |
| 5,413,101 A | 5/1995 | Sugiura |
| D359,546 S | 6/1995 | Savage et al. |
| 5,421,329 A | 6/1995 | Casciani et al. |
| 5,424,545 A | 6/1995 | Block et al. |
| 5,427,093 A | 6/1995 | Ogawa et al. |
| 5,429,128 A | 7/1995 | Cadell et al. |
| 5,431,170 A | 7/1995 | Mathews |
| 5,435,309 A | 7/1995 | Thomas et al. |
| D361,840 S | 8/1995 | Savage et al. |
| D362,063 S | 9/1995 | Savage et al. |
| 5,448,996 A | 9/1995 | Bellin et al. |
| 5,452,717 A | 9/1995 | Branigan et al. |
| D363,120 S | 10/1995 | Savage et al. |
| 5,456,252 A | 10/1995 | Vari et al. |
| RE35,122 E | 12/1995 | Corenman et al. |
| 5,479,934 A | 1/1996 | Imran |
| 5,482,036 A | 1/1996 | Diab et al. |
| 5,490,505 A | 2/1996 | Diab et al. |
| 5,490,523 A | 2/1996 | Isaacson et al. |
| 5,494,032 A | 2/1996 | Robinson et al. |
| 5,494,043 A | 2/1996 | O'Sullivan et al. |
| 5,503,148 A | 4/1996 | Pologe et al. |
| 5,520,177 A | 5/1996 | Ogawa |
| 5,533,507 A | 7/1996 | Potratz |
| 5,533,511 A | 7/1996 | Kaspari et al. |
| 5,534,851 A | 7/1996 | Russek |
| 5,539,831 A | 7/1996 | Harley |
| 5,551,423 A | 9/1996 | Sugiura |
| 5,553,615 A | 9/1996 | Carim et al. |
| 5,555,882 A | 9/1996 | Richardson et al. |
| 5,561,275 A | 10/1996 | Savage et al. |
| 5,562,002 A | 10/1996 | Lalin |
| 5,575,284 A | 11/1996 | Athan et al. |
| 5,577,500 A | 11/1996 | Potratz |
| 5,584,299 A | 12/1996 | Sakai et al. |
| 5,588,427 A | 12/1996 | Tien |
| 5,590,649 A | 1/1997 | Caro et al. |
| 5,590,652 A | 1/1997 | Inai |
| 5,595,176 A | 1/1997 | Yamaura |
| 5,596,992 A | 1/1997 | Haaland et al. |
| 5,602,924 A | 2/1997 | Durand et al. |
| 5,603,623 A | 2/1997 | Nishikawa et al. |
| 5,630,413 A | 5/1997 | Thomas et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,660,567 A | 8/1997 | Nierlich et al. |
| 5,662,106 A | 9/1997 | Swedlow et al. |
| 5,676,139 A | 10/1997 | Goldberger et al. |
| 5,676,141 A | 10/1997 | Hollub |
| 5,678,544 A | 10/1997 | Delonzor et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,690,104 A | 11/1997 | Kanemoto et al. |
| 5,692,503 A | 12/1997 | Kuenstner |

(56) References Cited

U.S. PATENT DOCUMENTS

| | | |
|---|---|---|
| 5,697,371 A | 12/1997 | Aoyagi |
| 5,701,894 A * | 12/1997 | Cherry et al. .................. 600/300 |
| 5,713,355 A | 2/1998 | Richardson et al. |
| 5,719,589 A | 2/1998 | Norman et al. |
| 5,720,284 A | 2/1998 | Aoyagi et al. |
| 5,724,983 A | 3/1998 | Selker et al. |
| D393,830 S | 4/1998 | Tobler et al. |
| 5,738,106 A | 4/1998 | Yamamori et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,587 A | 6/1998 | Gratton et al. |
| 5,779,630 A | 7/1998 | Fein et al. |
| 5,782,237 A | 7/1998 | Casciani et al. |
| 5,782,756 A | 7/1998 | Mannheimer |
| 5,782,757 A | 7/1998 | Diab et al. |
| 5,785,659 A | 7/1998 | Caro et al. |
| 5,790,729 A | 8/1998 | Pologe et al. |
| 5,791,347 A | 8/1998 | Flaherty et al. |
| 5,792,052 A | 8/1998 | Isaacson et al. |
| 5,793,485 A | 8/1998 | Gourley |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,810,723 A | 9/1998 | Aldrich |
| 5,810,724 A | 9/1998 | Gronvall |
| 5,810,734 A | 9/1998 | Caro et al. |
| 5,817,010 A | 10/1998 | Hibl |
| 5,818,985 A | 10/1998 | Merchant et al. |
| 5,819,007 A | 10/1998 | Elghazzawi |
| 5,823,950 A | 10/1998 | Diab et al. |
| 5,823,952 A | 10/1998 | Levinson et al. |
| 5,825,895 A | 10/1998 | Grasfield et al. |
| 5,827,182 A | 10/1998 | Raley et al. |
| 5,830,131 A | 11/1998 | Caro et al. |
| 5,830,137 A | 11/1998 | Sharf |
| 5,833,618 A | 11/1998 | Caro et al. |
| 5,839,439 A | 11/1998 | Nierlich et al. |
| RE36,000 E | 12/1998 | Swedlow et al. |
| 5,842,979 A | 12/1998 | Jarman |
| 5,851,178 A | 12/1998 | Aronow |
| 5,851,179 A | 12/1998 | Ritson et al. |
| 5,853,364 A | 12/1998 | Baker, Jr. et al. |
| 5,857,462 A | 1/1999 | Thomas et al. |
| 5,860,919 A | 1/1999 | Kiani-Azarbayjany et al. |
| 5,865,736 A | 2/1999 | Baker, Jr. et al. |
| 5,876,348 A | 3/1999 | Sugo |
| 5,885,213 A | 3/1999 | Richardson et al. |
| 5,890,929 A | 4/1999 | Mills et al. |
| 5,891,022 A | 4/1999 | Pologe |
| 5,891,024 A | 4/1999 | Jarman et al. |
| 5,904,654 A | 5/1999 | Wohltmann et al. |
| 5,910,108 A | 6/1999 | Solenberger |
| 5,916,154 A | 6/1999 | Hobbs et al. |
| 5,919,133 A | 7/1999 | Taylor |
| 5,919,134 A | 7/1999 | Diab |
| 5,921,921 A | 7/1999 | Potratz et al. |
| 5,928,156 A | 7/1999 | Krumbiegel |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling |
| 5,978,691 A | 11/1999 | Mills |
| 5,983,122 A | 11/1999 | Jarman et al. |
| 5,995,855 A | 11/1999 | Kiani et al. |
| 5,995,856 A | 11/1999 | Mannheimer et al. |
| 5,995,859 A | 11/1999 | Takahashi |
| 5,997,343 A | 12/1999 | Mills et al. |
| 5,999,841 A | 12/1999 | Aoyagi et al. |
| 6,002,952 A | 12/1999 | Diab et al. |
| 6,006,119 A | 12/1999 | Soller et al. |
| 6,011,986 A | 1/2000 | Diab et al. |
| 6,014,576 A | 1/2000 | Raley |
| 6,018,673 A | 1/2000 | Chin et al. |
| 6,018,674 A | 1/2000 | Aronow |
| 6,023,541 A | 2/2000 | Merchant et al. |
| 6,027,452 A | 2/2000 | Flaherty et al. |
| 6,029,665 A | 2/2000 | Berthon-Jones |
| 6,036,642 A | 3/2000 | Diab et al. |
| 6,045,509 A | 4/2000 | Caro et al. |
| 6,064,898 A | 5/2000 | Aldrich |
| 6,064,910 A | 5/2000 | Andersson et al. |
| 6,067,462 A | 5/2000 | Diab et al. |
| 6,068,594 A | 5/2000 | Schloemer et al. |
| 6,073,037 A | 6/2000 | Alam et al. |
| 6,081,735 A | 6/2000 | Diab et al. |
| 6,083,156 A | 7/2000 | Lisiecki |
| 6,083,172 A | 7/2000 | Baker, Jr. et al. |
| 6,088,607 A | 7/2000 | Diab et al. |
| 6,094,592 A | 7/2000 | Yorkey et al. |
| 6,104,938 A | 8/2000 | Huiku |
| 6,106,481 A | 8/2000 | Cohen |
| 6,110,522 A | 8/2000 | Lepper, Jr. et al. |
| 6,112,107 A | 8/2000 | Hannula |
| 6,122,042 A | 9/2000 | Wunderman et al. |
| 6,124,597 A | 9/2000 | Shehada |
| 6,128,521 A | 10/2000 | Marro et al. |
| 6,129,675 A | 10/2000 | Jay |
| 6,138,675 A | 10/2000 | Berthon-Jones |
| 6,144,868 A | 11/2000 | Parker |
| 6,149,588 A | 11/2000 | Noda et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,041 A | 12/2000 | Thomas et al. |
| 6,157,850 A | 12/2000 | Diab et al. |
| 6,165,005 A | 12/2000 | Mills et al. |
| 6,168,568 B1 | 1/2001 | Gavriely |
| 6,174,283 B1 | 1/2001 | Nevo et al. |
| 6,184,521 B1 | 2/2001 | Coffin, IV et al. |
| 6,192,261 B1 | 2/2001 | Gratton et al. |
| 6,206,830 B1 | 3/2001 | Diab et al. |
| 6,226,539 B1 | 5/2001 | Potratz |
| 6,229,856 B1 | 5/2001 | Diab et al. |
| 6,230,035 B1 | 5/2001 | Aoyagi et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,248,083 B1 | 6/2001 | Smith et al. |
| 6,253,097 B1 | 6/2001 | Aronow et al. |
| 6,254,551 B1 | 7/2001 | Varis |
| 6,256,523 B1 | 7/2001 | Diab et al. |
| 6,262,698 B1 | 7/2001 | Blum |
| 6,263,222 B1 | 7/2001 | Diab et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,301,493 B1 | 10/2001 | Marro et al. |
| 6,304,675 B1 | 10/2001 | Osbourn et al. |
| 6,304,767 B1 | 10/2001 | Soller et al. |
| 6,317,627 B1 | 11/2001 | Ennen et al. |
| 6,321,100 B1 | 11/2001 | Parker |
| 6,325,761 B1 | 12/2001 | Jay |
| 6,330,468 B1 | 12/2001 | Scharf |
| 6,334,065 B1 | 12/2001 | Al-Ali et al. |
| 6,337,798 B1 | 1/2002 | Hailey et al. |
| 6,341,257 B1 | 1/2002 | Haaland |
| 6,343,224 B1 | 1/2002 | Parker |
| 6,349,228 B1 | 2/2002 | Kiani et al. |
| 6,351,658 B1 | 2/2002 | Middleman et al. |
| 6,356,774 B1 | 3/2002 | Bernstein et al. |
| 6,360,113 B1 | 3/2002 | Dettling |

(56) References Cited

U.S. PATENT DOCUMENTS

| | | |
|---|---|---|
| 6,360,114 B1 | 3/2002 | Diab et al. |
| 6,363,269 B1 | 3/2002 | Hanna et al. |
| 6,368,283 B1 | 4/2002 | Xu et al. |
| 6,371,921 B1 | 4/2002 | Caro et al. |
| 6,374,129 B1 | 4/2002 | Chin et al. |
| 6,377,828 B1 | 4/2002 | Chaiken et al. |
| 6,377,829 B1 | 4/2002 | Al-Ali |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,408,198 B1 | 6/2002 | Hanna et al. |
| 6,411,833 B1 | 6/2002 | Baker, Jr. et al. |
| 6,415,166 B1 | 7/2002 | Van Hoy et al. |
| 6,415,233 B1 | 7/2002 | Haaland |
| 6,415,236 B2 | 7/2002 | Kobayashi et al. |
| 6,421,549 B1 | 7/2002 | Jacques |
| 6,430,437 B1 | 8/2002 | Marro |
| 6,430,525 B1 | 8/2002 | Weber et al. |
| 6,434,408 B1 | 8/2002 | Heckel |
| 6,441,388 B1 | 8/2002 | Thomas et al. |
| 6,443,907 B1 | 9/2002 | Mansy et al. |
| 6,453,184 B1 | 9/2002 | Hyogo et al. |
| 6,455,340 B1 | 9/2002 | Chua et al. |
| 6,463,310 B1 | 10/2002 | Swedlow et al. |
| 6,463,311 B1 | 10/2002 | Diab |
| 6,466,824 B1 | 10/2002 | Struble |
| 6,470,199 B1 | 10/2002 | Kopotic et al. |
| 6,480,729 B2 | 11/2002 | Stone |
| 6,486,588 B2 | 11/2002 | Doron et al. |
| 6,490,466 B1 | 12/2002 | Fein et al. |
| 6,491,647 B1 | 12/2002 | Bridger et al. |
| 6,497,659 B1 | 12/2002 | Rafert |
| 6,501,974 B2 | 12/2002 | Huiku |
| 6,501,975 B2 | 12/2002 | Diab et al. |
| 6,504,943 B1 | 1/2003 | Sweatt et al. |
| 6,505,059 B1 | 1/2003 | Kollias et al. |
| 6,505,060 B1 | 1/2003 | Norris |
| 6,505,061 B2 | 1/2003 | Larson |
| 6,505,133 B1 | 1/2003 | Hanna |
| 6,510,329 B2 | 1/2003 | Heckel |
| 6,515,273 B2 | 2/2003 | Al-Ali |
| 6,517,497 B2 | 2/2003 | Rymut et al. |
| 6,519,486 B1 | 2/2003 | Edgar, Jr. et al. |
| 6,519,487 B1 | 2/2003 | Parker |
| 6,522,398 B2 | 2/2003 | Cadell et al. |
| 6,525,386 B1 | 2/2003 | Mills et al. |
| 6,526,300 B1 | 2/2003 | Kiani et al. |
| 6,526,301 B2 | 2/2003 | Larsen et al. |
| 6,528,809 B1 | 3/2003 | Thomas et al. |
| 6,537,225 B1 | 3/2003 | Mills |
| 6,541,756 B2 | 4/2003 | Schulz et al. |
| 6,542,763 B1 | 4/2003 | Yamashita et al. |
| 6,542,764 B1 | 4/2003 | Al-Ali et al. |
| 6,545,652 B1 | 4/2003 | Tsuji |
| 6,546,267 B1 | 4/2003 | Sugiura |
| 6,553,241 B2 | 4/2003 | Mannheimer et al. |
| 6,564,077 B2 | 5/2003 | Mortara |
| 6,571,113 B1 | 5/2003 | Fein et al. |
| 6,580,086 B1 | 6/2003 | Schulz et al. |
| 6,582,964 B1 | 6/2003 | Samsoondar et al. |
| 6,584,336 B1 | 6/2003 | Ali et al. |
| 6,584,413 B1 | 6/2003 | Keenan et al. |
| 6,591,123 B2 | 7/2003 | Fein et al. |
| 6,594,511 B2 | 7/2003 | Stone et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,609,016 B1 | 8/2003 | Lynn |
| 6,611,698 B1 | 8/2003 | Yamashita et al. |
| 6,614,521 B2 | 9/2003 | Samsoondar et al. |
| 6,615,064 B1 | 9/2003 | Aldrich |
| 6,615,151 B1 | 9/2003 | Scecina et al. |
| 6,618,602 B2 | 9/2003 | Levin |
| 6,622,095 B2 | 9/2003 | Kobayashi et al. |
| 6,628,975 B1 | 9/2003 | Fein et al. |
| 6,631,281 B1 | 10/2003 | Kastle |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,647,280 B2 | 11/2003 | Bahr et al. |
| 6,650,917 B2 | 11/2003 | Diab et al. |
| 6,654,623 B1 | 11/2003 | Kastle |
| 6,654,624 B2 | 11/2003 | Diab et al. |
| 6,657,717 B2 | 12/2003 | Cadell et al. |
| 6,658,276 B2 | 12/2003 | Kianl et al. |
| 6,658,277 B2 | 12/2003 | Wasserman |
| 6,661,161 B1 | 12/2003 | Lanzo et al. |
| 6,662,033 B2 | 12/2003 | Casciani et al. |
| 6,665,551 B1 | 12/2003 | Suzuki |
| 6,668,183 B2 | 12/2003 | Hicks et al. |
| 6,671,526 B1 | 12/2003 | Aoyagi et al. |
| 6,671,531 B2 | 12/2003 | Al-Ali et al. |
| 6,675,031 B1 | 1/2004 | Porges et al. |
| 6,675,106 B1 | 1/2004 | Keenan et al. |
| 6,678,543 B2 | 1/2004 | Diab et al. |
| 6,681,126 B2 | 1/2004 | Solenberger |
| 6,684,090 B2 | 1/2004 | Ali et al. |
| 6,684,091 B2 | 1/2004 | Parker |
| 6,687,620 B1 | 2/2004 | Haaland et al. |
| 6,690,466 B2 | 2/2004 | Miller et al. |
| 6,694,157 B1 | 2/2004 | Stone et al. |
| 6,697,655 B2 | 2/2004 | Sueppel et al. |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,701,170 B2 | 3/2004 | Stetson |
| 6,708,049 B1 | 3/2004 | Berson et al. |
| 6,711,503 B2 | 3/2004 | Haaland |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,705 B2 | 4/2004 | Mills |
| 6,720,734 B2 | 4/2004 | Norris |
| 6,721,582 B2 | 4/2004 | Trepagnier et al. |
| 6,721,584 B2 | 4/2004 | Baker, Jr. et al. |
| 6,721,585 B1 | 4/2004 | Parker |
| 6,725,074 B1 | 4/2004 | Kastle |
| 6,725,075 B2 | 4/2004 | Al-Ali |
| 6,726,634 B2 | 4/2004 | Freeman |
| 6,728,560 B2 | 4/2004 | Kollias et al. |
| 6,735,459 B2 | 5/2004 | Parker |
| 6,741,875 B1 | 5/2004 | Pawluczyk et al. |
| 6,741,876 B1 | 5/2004 | Scecina et al. |
| 6,743,172 B1 | 6/2004 | Blike |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,766,038 B1 | 7/2004 | Sakuma et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,788,849 B1 | 9/2004 | Pawluczyk |
| 6,792,300 B1 | 9/2004 | Diab et al. |
| 6,800,373 B2 | 10/2004 | Gorczyca |
| 6,801,797 B2 | 10/2004 | Mannheimer et al. |
| 6,801,799 B2 | 10/2004 | Mendelson |
| 6,810,277 B2 | 10/2004 | Edgar, Jr. et al. |

(56) References Cited

U.S. PATENT DOCUMENTS

| | | |
|---|---|---|
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,829,501 B2 | 12/2004 | Nielsen et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,581 B1 | 1/2005 | El-Solh et al. |
| 6,839,582 B2 | 1/2005 | Heckel |
| 6,842,702 B2 | 1/2005 | Haaland et al. |
| 6,845,256 B2 | 1/2005 | Chin et al. |
| 6,847,835 B1 | 1/2005 | Yamanishi |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,861,641 B1 | 3/2005 | Adams |
| 6,869,402 B2 | 3/2005 | Arnold |
| 6,882,874 B2 | 4/2005 | Huiku |
| 6,898,452 B2 | 5/2005 | Al-Ali et al. |
| 6,912,049 B2 | 6/2005 | Pawluczyk et al. |
| 6,917,422 B2 | 7/2005 | Samsoondar et al. |
| 6,918,878 B2 | 7/2005 | Brodnick |
| 6,919,566 B1 | 7/2005 | Cadell |
| 6,920,345 B2 | 7/2005 | Al-Ali et al. |
| 6,921,367 B2 | 7/2005 | Mills |
| 6,922,645 B2 | 7/2005 | Haaland et al. |
| 6,928,311 B1 | 8/2005 | Pawluczyk et al. |
| 6,931,268 B1 | 8/2005 | Kiani-Azarbayjany et al. |
| 6,931,269 B2 | 8/2005 | Terry |
| 6,934,570 B2 | 8/2005 | Kiani et al. |
| 6,937,736 B2 | 8/2005 | Toda |
| 6,939,305 B2 | 9/2005 | Flaherty et al. |
| 6,943,348 B1 | 9/2005 | Coffin, IV |
| 6,944,487 B2 | 9/2005 | Maynard et al. |
| 6,949,075 B2 | 9/2005 | Hatlesad et al. |
| 6,950,687 B2 | 9/2005 | Al-Ali |
| 6,956,572 B2 | 10/2005 | Zaleski |
| 6,961,598 B2 | 11/2005 | Diab |
| 6,970,792 B1 | 11/2005 | Diab |
| 6,975,891 B2 | 12/2005 | Pawluczyk |
| 6,979,812 B2 | 12/2005 | Al-Ali |
| 6,985,764 B2 | 1/2006 | Mason et al. |
| 6,987,994 B1 | 1/2006 | Mortz |
| 6,993,371 B2 | 1/2006 | Kiani et al. |
| 6,996,427 B2 | 2/2006 | Ali et al. |
| 6,999,904 B2 | 2/2006 | Weber et al. |
| 7,001,337 B2 | 2/2006 | Dekker |
| 7,003,338 B2 | 2/2006 | Weber et al. |
| 7,003,339 B2 | 2/2006 | Diab et al. |
| 7,006,856 B2 | 2/2006 | Baker, Jr. et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| 7,112,173 B1 * | 9/2006 | Kantorovich et al. ........ 600/449 |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,194,306 B1 | 3/2007 | Turcott |
| 7,215,984 B2 | 5/2007 | Diab et al. |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B2 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,299,080 B2 | 11/2007 | Acosta et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,398,115 B2 | 7/2008 | Lynn |
| 7,415,297 B2 | 8/2008 | Al-Ali et al. |
| 7,416,531 B2 | 8/2008 | Mohler |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,539,533 B2 | 5/2009 | Tran |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| 7,670,726 B2 | 3/2010 | Lu |
| D614,305 S | 4/2010 | Al-Ali et al. |
| 7,690,378 B1 | 4/2010 | Turcott |
| 7,691,070 B2 | 4/2010 | Comanducci |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |

(56) References Cited

U.S. PATENT DOCUMENTS

| | | |
|---|---|---|
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,856,207 B2 | 12/2010 | Martch et al. |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,257,089 B2 | 9/2012 | Lecat |
| 8,260,577 B2 | 9/2012 | Weber et al. |
| 8,265,291 B2 | 9/2012 | Bridger |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Dalke et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,449,469 B2 | 5/2013 | Banet et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 2001/0044700 A1 | 11/2001 | Kobayashi et al. |
| 2001/0045532 A1 | 11/2001 | Schulz et al. |
| 2002/0021269 A1 | 2/2002 | Rast |
| 2002/0026107 A1 | 2/2002 | Kiani et al. |
| 2002/0035318 A1 | 3/2002 | Mannheimer et al. |
| 2002/0038078 A1 | 3/2002 | Ito |
| 2002/0038081 A1 | 3/2002 | Fein et al. |
| 2002/0051290 A1 | 5/2002 | Hannington |
| 2002/0059047 A1 | 5/2002 | Haaland |
| 2002/0082488 A1 | 6/2002 | Al-Ali et al. |
| 2002/0095078 A1 | 7/2002 | Mannheimer et al. |
| 2002/0111748 A1 | 8/2002 | Kobayashi et al. |
| 2002/0115919 A1 | 8/2002 | Al-Ali |
| 2002/0126036 A1 | 9/2002 | Flaherty et al. |
| 2002/0154665 A1 | 10/2002 | Funabashi et al. |
| 2002/0156353 A1 | 10/2002 | Larson |
| 2002/0159002 A1 | 10/2002 | Chang |
| 2002/0161291 A1 | 10/2002 | Kiani et al. |
| 2002/0165440 A1 | 11/2002 | Mason et al. |
| 2002/0183819 A1 | 12/2002 | Struble |
| 2002/0193670 A1 | 12/2002 | Garfield et al. |
| 2002/0198469 A1 | 12/2002 | Bridger et al. |
| 2003/0002685 A1 | 1/2003 | Werblud |
| 2003/0015368 A1 | 1/2003 | Cybulski et al. |
| 2003/0045784 A1 | 3/2003 | Palatnik et al. |
| 2003/0045785 A1 | 3/2003 | Diab et al. |
| 2003/0049232 A1 | 3/2003 | Page et al. |
| 2003/0076494 A1 | 4/2003 | Bonin et al. |
| 2003/0109775 A1 | 6/2003 | O'Neil et al. |
| 2003/0116769 A1 | 6/2003 | Song et al. |
| 2003/0117296 A1 | 6/2003 | Seely |
| 2003/0120160 A1 | 6/2003 | Yarita |
| 2003/0120164 A1 | 6/2003 | Nielsen et al. |
| 2003/0135099 A1 | 7/2003 | Al-Ali |
| 2003/0135129 A1 | 7/2003 | Cusimano et al. |

(56) References Cited

U.S. PATENT DOCUMENTS

| | | |
|---|---|---|
| 2003/0139657 A1 | 7/2003 | Solenberger |
| 2003/0158466 A1 | 8/2003 | Lynn et al. |
| 2003/0160257 A1 | 8/2003 | Bader et al. |
| 2003/0195402 A1 | 10/2003 | Fein et al. |
| 2004/0006261 A1 | 1/2004 | Swedlow et al. |
| 2004/0010202 A1 | 1/2004 | Nakatani |
| 2004/0033618 A1 | 2/2004 | Haass et al. |
| 2004/0059203 A1 | 3/2004 | Guerrero |
| 2004/0059209 A1 | 3/2004 | Al Ali et al. |
| 2004/0064259 A1 | 4/2004 | Haaland et al. |
| 2004/0081621 A1 | 4/2004 | Arndt et al. |
| 2004/0092805 A1 | 5/2004 | Yarita |
| 2004/0133087 A1 | 7/2004 | Ali et al. |
| 2004/0138538 A1 | 7/2004 | Stetson |
| 2004/0138540 A1 | 7/2004 | Baker, Jr. et al. |
| 2004/0147822 A1 | 7/2004 | Al-Ali et al. |
| 2004/0147823 A1 | 7/2004 | Kiani et al. |
| 2004/0152957 A1 | 8/2004 | Stivoric et al. |
| 2004/0158132 A1 | 8/2004 | Zaleski |
| 2004/0158134 A1 | 8/2004 | Diab et al. |
| 2004/0158135 A1 | 8/2004 | Baker, Jr. et al. |
| 2004/0158162 A1 | 8/2004 | Narimatsu |
| 2004/0162472 A1 | 8/2004 | Berson et al. |
| 2004/0167382 A1 | 8/2004 | Gardner et al. |
| 2004/0167416 A1 | 8/2004 | Lee |
| 2004/0171940 A1 | 9/2004 | Narimatsu |
| 2004/0176670 A1 | 9/2004 | Takamura et al. |
| 2004/0181134 A1 | 9/2004 | Baker, Jr. et al. |
| 2004/0199063 A1 | 10/2004 | O'Neil et al. |
| 2004/0204639 A1 | 10/2004 | Casciani et al. |
| 2004/0204868 A1 | 10/2004 | Maynard et al. |
| 2004/0228494 A1 | 11/2004 | Smith |
| 2004/0229391 A1 | 11/2004 | Ohya et al. |
| 2004/0262046 A1 | 12/2004 | Simon et al. |
| 2004/0267103 A1 | 12/2004 | Li et al. |
| 2004/0267140 A1 | 12/2004 | Ito et al. |
| 2005/0014999 A1 | 1/2005 | Rahe-Meyer |
| 2005/0043902 A1 | 2/2005 | Haaland et al. |
| 2005/0049469 A1 | 3/2005 | Aoyagi et al. |
| 2005/0054908 A1 | 3/2005 | Blank et al. |
| 2005/0070773 A1 | 3/2005 | Chin et al. |
| 2005/0070775 A1 | 3/2005 | Chin et al. |
| 2005/0075546 A1 | 4/2005 | Samsoondar et al. |
| 2005/0085704 A1 | 4/2005 | Schulz et al. |
| 2005/0085735 A1 | 4/2005 | Baker, Jr. et al. |
| 2005/0124871 A1 | 6/2005 | Baker, Jr. et al. |
| 2005/0131663 A1 | 6/2005 | Bangs et al. |
| 2005/0143634 A1 | 6/2005 | Baker, Jr. et al. |
| 2005/0143943 A1 | 6/2005 | Brown |
| 2005/0148834 A1 | 7/2005 | Hull et al. |
| 2005/0184895 A1 | 8/2005 | Petersen et al. |
| 2005/0187447 A1 | 8/2005 | Chew et al. |
| 2005/0187448 A1 | 8/2005 | Petersen et al. |
| 2005/0187449 A1 | 8/2005 | Chew et al. |
| 2005/0187450 A1 | 8/2005 | Chew et al. |
| 2005/0187452 A1 | 8/2005 | Petersen et al. |
| 2005/0187453 A1 | 8/2005 | Petersen et al. |
| 2005/0197549 A1 | 9/2005 | Baker, Jr. |
| 2005/0197579 A1 | 9/2005 | Baker, Jr. |
| 2005/0197793 A1 | 9/2005 | Baker, Jr. |
| 2005/0203357 A1 | 9/2005 | Debreczeny et al. |
| 2005/0209515 A1 | 9/2005 | Hockersmith et al. |
| 2005/0228253 A1 | 10/2005 | Debreczeny |
| 2005/0250997 A1 | 11/2005 | Takedo et al. |
| 2005/0272987 A1 | 12/2005 | Kiani-Azarbayjany et al. |
| 2005/0283059 A1 | 12/2005 | Iyer et al. |
| 2006/0030764 A1 | 2/2006 | Porges et al. |
| 2006/0047215 A1 | 3/2006 | Newman et al. |
| 2006/0129067 A1 | 6/2006 | Grajales et al. |
| 2006/0144397 A1 | 7/2006 | Wallace et al. |
| 2006/0149144 A1 | 7/2006 | Lynn et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0184052 A1 | 8/2006 | Iwasawa |
| 2006/0189880 A1 | 8/2006 | Lynn et al. |
| 2006/0195041 A1 | 8/2006 | Lynn et al. |
| 2006/0198533 A1 | 9/2006 | Wang et al. |
| 2006/0210120 A1 | 9/2006 | Rowe et al. |
| 2006/0211922 A1 | 9/2006 | Al-Ali et al. |
| 2006/0211923 A1 | 9/2006 | Al-Ali et al. |
| 2006/0211924 A1 | 9/2006 | Smith et al. |
| 2006/0211925 A1 | 9/2006 | Lamego et al. |
| 2006/0211932 A1* | 9/2006 | Al-Ali et al. ............... 600/344 |
| 2006/0226992 A1 | 10/2006 | Al-Ali et al. |
| 2006/0229509 A1 | 10/2006 | Al-Ali et al. |
| 2006/0235324 A1 | 10/2006 | Lynn |
| 2006/0238333 A1 | 10/2006 | Welch et al. |
| 2006/0238358 A1 | 10/2006 | Al-Ali et al. |
| 2006/0241358 A1 | 10/2006 | Al-Ali et al. |
| 2006/0241363 A1 | 10/2006 | Al-Ali et al. |
| 2006/0241510 A1 | 10/2006 | Halperin et al. |
| 2007/0049837 A1 | 3/2007 | Shertukde et al. |
| 2007/0093721 A1 | 4/2007 | Lynn et al. |
| 2007/0123763 A1 | 5/2007 | Al-Ali et al. |
| 2007/0129643 A1 | 6/2007 | Kwok et al. |
| 2007/0129647 A1 | 6/2007 | Lynn |
| 2007/0135725 A1 | 6/2007 | Hatlestad |
| 2007/0149860 A1 | 6/2007 | Lynn et al. |
| 2007/0149864 A1 | 6/2007 | Laakkonen |
| 2007/0149865 A1 | 6/2007 | Laakkonen |
| 2007/0173730 A1 | 7/2007 | Bikko |
| 2007/0185397 A1 | 8/2007 | Govari et al. |
| 2007/0239057 A1 | 10/2007 | Pu et al. |
| 2007/0282212 A1 | 12/2007 | Sierra et al. |
| 2008/0039735 A1 | 2/2008 | Hickerson |
| 2008/0071185 A1 | 3/2008 | Beck et al. |
| 2008/0076972 A1 | 3/2008 | Dorogusker et al. |
| 2008/0077198 A1 | 3/2008 | Webb et al. |
| 2008/0077435 A1 | 3/2008 | Muradia |
| 2008/0119716 A1 | 5/2008 | Boric-Lubecke et al. |
| 2008/0137876 A1 | 6/2008 | Kassal et al. |
| 2008/0161878 A1 | 7/2008 | Tehrani et al. |
| 2008/0188733 A1 | 8/2008 | Al-Ali et al. |
| 2008/0219464 A1 | 9/2008 | Smith |
| 2008/0275349 A1 | 11/2008 | Halperin et al. |
| 2009/0018429 A1 | 1/2009 | Saliga et al. |
| 2009/0093687 A1 | 4/2009 | Telfort et al. |
| 2009/0170664 A1 | 7/2009 | Shirasaki et al. |
| 2009/0187065 A1 | 7/2009 | Basinger |
| 2009/0299157 A1 | 12/2009 | Telfort et al. |
| 2009/0316925 A1 | 12/2009 | Eisenfeld et al. |
| 2010/0274099 A1 | 10/2010 | Telfort et al. |
| 2010/0298661 A1 | 11/2010 | McCombie et al. |
| 2010/0324377 A1 | 12/2010 | Woehrle |
| 2011/0009710 A1 | 1/2011 | Kroeger et al. |
| 2011/0009719 A1 | 1/2011 | Al-Ali et al. |
| 2011/0118573 A1 | 5/2011 | McKenna |
| 2011/0125060 A1 | 5/2011 | Telfort et al. |
| 2011/0172561 A1 | 7/2011 | Kiani et al. |
| 2011/0196211 A1 | 8/2011 | Al-Ali et al. |
| 2011/0209915 A1 | 9/2011 | Telfort et al. |
| 2011/0213271 A1 | 9/2011 | Telfort et al. |
| 2011/0213272 A1 | 9/2011 | Telfort et al. |
| 2011/0213273 A1 | 9/2011 | Telfort et al. |
| 2011/0213274 A1 | 9/2011 | Telfort et al. |
| 2011/0224567 A1 | 9/2011 | Al-Ali |
| 2011/0237914 A1 | 9/2011 | Lamego |
| 2011/0288431 A1 | 11/2011 | Alshaer et al. |
| 2012/0046530 A1 | 2/2012 | Al-Ali |
| 2012/0161970 A1 | 6/2012 | Al-Ali |
| 2012/0232359 A1 | 9/2012 | Al-Ali et al. |
| 2012/0232363 A1 | 9/2012 | Al-Ali et al. |

FOREIGN PATENT DOCUMENTS

| | | |
|---|---|---|
| EP | 0 231 379 | 8/1987 |
| EP | 41 92 23 | 3/1991 |
| EP | 0 569 670 | 2/1993 |
| EP | 0 529 412 | 3/1993 |
| EP | 0 675 540 | 10/1995 |
| EP | 0 675 541 | 10/1995 |
| EP | 0716628 | 12/1998 |
| EP | 0659058 | 1/1999 |

(56) References Cited

FOREIGN PATENT DOCUMENTS

| | | |
|---|---|---|
| EP | 0956820 A1 | 11/1999 |
| EP | 1 080 683 | 3/2001 |
| EP | 1207536 | 5/2002 |
| EP | 1207536 A2 | 5/2002 |
| EP | 1860992 | 12/2007 |
| EP | 2014234 | 1/2009 |
| EP | 1 895 892 | 5/2010 |
| EP | 2 305 104 | 4/2011 |
| EP | 2 476 369 | 7/2012 |
| EP | 2 139 383 | 2/2013 |
| FR | 2 847 796 | 6/2004 |
| GB | 2358546 | 11/1999 |
| GB | 2 358 546 | 7/2001 |
| GB | 2 487 882 | 8/2012 |
| JP | 60059900 | 4/1985 |
| JP | 61-28172 | 2/1986 |
| JP | 62-000324 | 1/1987 |
| JP | 6214898 | 1/1987 |
| JP | 63-275327 | 11/1988 |
| JP | 64-500495 | 2/1989 |
| JP | 2-126829 | 5/1990 |
| JP | 2-145457 | 12/1990 |
| JP | 05-207993 | 8/1993 |
| JP | H05-200017 | 8/1993 |
| JP | 6-505903 | 7/1994 |
| JP | 6-237013 | 8/1994 |
| JP | 7-281618 | 10/1995 |
| JP | 07-325546 | 12/1995 |
| JP | 9-192120 | 7/1997 |
| JP | 01-309872 | 6/1998 |
| JP | 10-155755 | 6/1998 |
| JP | 10-216112 | 8/1998 |
| JP | 10-509352 | 9/1998 |
| JP | 10-269344 A | 10/1998 |
| JP | 10-295676 | 11/1998 |
| JP | 10-305026 | 11/1998 |
| JP | 2001-50713 | 5/1999 |
| JP | 11-163412 | 6/1999 |
| JP | 11-164826 | 6/1999 |
| JP | 11-506834 | 6/1999 |
| JP | 11-183377 | 7/1999 |
| JP | H11-508691 | 7/1999 |
| JP | 2000-116625 | 4/2000 |
| JP | 2002-516689 | 6/2002 |
| JP | 2002-228579 | 8/2002 |
| JP | 2002-525151 | 8/2002 |
| JP | 2002-315739 | 10/2002 |
| JP | 2003-507718 | 2/2003 |
| JP | 2003-084108 | 3/2003 |
| JP | 2003-521985 | 7/2003 |
| JP | 2003-329719 | 11/2003 |
| JP | 2004-070179 | 3/2004 |
| JP | 2004-510467 | 4/2004 |
| JP | 2004-226277 | 8/2004 |
| JP | 2004-296736 | 10/2004 |
| JP | 2004-532526 | 10/2004 |
| JP | 2004-327760 | 11/2004 |
| JP | 2005-501589 | 1/2005 |
| JP | 2005-253478 | 9/2005 |
| JP | 2007-558237 | 3/2006 |
| JP | 2008-505706 | 2/2008 |
| JP | 4879913 | 12/2011 |
| JP | 2012-110746 | 6/2012 |
| JP | 2012-130756 | 7/2012 |
| JP | 5096174 | 9/2012 |
| JP | 5166619 | 3/2013 |
| WO | WO 88/01150 | 2/1988 |
| WO | WO 88/02020 | 2/1988 |
| WO | WO 92/16142 | 10/1992 |
| WO | WO 94/05207 | 3/1994 |
| WO | WO 94/13207 | 6/1994 |
| WO | WO 95/16387 | 6/1995 |
| WO | WO 95/29632 | 11/1995 |
| WO | WO 96/13208 | 5/1996 |
| WO | WO 96/41138 | 12/1996 |
| WO | WO 97/01985 | 1/1997 |
| WO | WO 98/43071 | 10/1998 |
| WO | WO 99/53277 | 10/1999 |
| WO | WO 00/10462 | 3/2000 |
| WO | WO 00/18290 | 4/2000 |
| WO | WO 00/42911 A1 | 7/2000 |
| WO | WO 00/59374 | 10/2000 |
| WO | WO 01/13790 | 3/2001 |
| WO | WO 01/30414 | 5/2001 |
| WO | WO 01/34033 | 5/2001 |
| WO | WO 01/58347 | 8/2001 |
| WO | WO 01/78059 | 10/2001 |
| WO | WO 01/87005 | 11/2001 |
| WO | WO 01/97691 | 12/2001 |
| WO | WO 02/03042 | 1/2002 |
| WO | WO 02/17780 | 3/2002 |
| WO | WO 02/24067 | 3/2002 |
| WO | WO 02/26123 | 4/2002 |
| WO | WO 02/089664 | 11/2002 |
| WO | WO 03/020129 | 3/2003 |
| WO | WO 03/058646 | 7/2003 |
| WO | WO 03/058646 A1 | 7/2003 |
| WO | WO 03/068060 | 8/2003 |
| WO | WO 03/077761 | 9/2003 |
| WO | WO 03/087737 | 10/2003 |
| WO | WO 2004/000111 | 12/2003 |
| WO | WO 2004/004411 | 1/2004 |
| WO | WO 2004/034898 | 4/2004 |
| WO | WO 2004/038801 | 5/2004 |
| WO | WO 2005/011488 | 2/2005 |
| WO | WO 2005/096931 | 10/2005 |
| WO | WO 2005/096931 A1 | 10/2005 |
| WO | WO 2005/099562 | 10/2005 |
| WO | WO 2006/094155 | 9/2006 |
| WO | WO 2006/094168 | 9/2006 |
| WO | WO 2008/017246 | 2/2008 |
| WO | WO 2008/148172 | 12/2008 |
| WO | WO 2009/093159 A1 | 7/2009 |
| WO | WO 2009/137524 | 11/2009 |
| WO | WO 2009/137524 A2 | 11/2009 |
| WO | WO 2009/155593 | 12/2009 |
| WO | WO 2011/047207 | 4/2011 |
| WO | WO 2011/047209 | 4/2011 |
| WO | WO 2011/047213 | 4/2011 |
| WO | WO 2011/047216 | 4/2011 |
| WO | WO 2011/147211 | 4/2011 |
| WO | WO 2011/069122 | 6/2011 |

OTHER PUBLICATIONS

Sierra et al., Monitoring Respiratory Rate Based on Tracheal Sounds. First Experieances, Proceedings of the 26th Annual Int'l Conf. of the IEEE EMBS (Sep. 2004), 317-320.
U.S. Appl. No. 12/904,775, filed Oct. 14, 2010, Fechter et al.
U.S. Appl. No. 12/904,789, filed Oct. 14, 2010, Telfort, Valery et al.
U.S. Appl. No. 12/904,823, filed Oct. 14, 2010, Al-Ali et al.
U.S. Appl. No. 12/904,836, filed Oct. 14, 2010, Al-Ali et al.
U.S. Appl. No. 12/904,890, filed Oct. 14, 2010, Telfort et al.
U.S. Appl. No. 12/904,907, filed Oct. 14, 2010, Telfort et al.
U.S. Appl. No. 12/904,931, filed Oct. 14, 2010, Telfort et al.
U.S. Appl. No. 12/904,938, filed Oct. 14, 2010, Telfort et al.
U.S. Appl. No. 12/905,036, filed Oct. 14, 2010, Kiani et al.
U.S. Appl. No. 12/905,384, filed Oct. 15, 2010, Al-Ali et al.
U.S. Appl. No. 12/905,449, filed Oct. 15, 2010, Al-Ali et al.
U.S. Appl. No. 12/905,489, filed Oct. 15, 2010, Weber et al.
U.S. Appl. No. 12/905,530, filed Oct. 15, 2010, Al-Ali et al.
Analog Devices, 12-Bit Serial Input Multiplying D/A Converter, Product Data Sheet, 2000.
International Search Report & Written Opinion, PCT Application PCT/US2010/052758, Feb. 10, 2011; 12 pages.
International Search Report & Written Opinion, PCT Application PCT/US2010/058981, Feb. 17, 2011; 11 pages.
International Search Report, PCT Application PCT/CA2003/000536, Dec. 11, 2003; 2 pages.
International Search Report, PCT Application PCT/US2009/069287, Mar. 30, 2010; 7 pages.
Welch Allyn, ECG ASIC, Product Data Sheete, 2001.

(56) References Cited

OTHER PUBLICATIONS

Analog Devices, "12-Bit Serial Input Multiplying D/A Converter, DAC8043A, Analog Devices, Inc.," 2000.
Avago Technologies, "HCNR200 and HCNR201, High-Linearity Analog Optocouplers," Data Sheet, Avago Technologies, Nov. 18, 2008.
Chambrin, M-C., "Alarms in the intensive care unit: how can the number of false alarms be reduced?"; Critical Care Aug. 2001, vol. 5 No. 4; p. 1-5.
Eldor et al., "A device for monitoring respiration during anesthesia; the para-tracheal monitor", Canadian Journal of Anesthesia, 1990, vol. 9, No. 1, p. 95-98.
European Office Action in Application No. 05732095.4, dated on Oct. 25, 2011 in 4 pages.
European Office Action in Application No. 057320954, dated Mar. 30, 2012.
European Office Action in Application No. 03711767.8, dated May 18, 2011.
European Office Action in Application No. 09743510.1, dated Oct. 10, 2011.
Japanese Final Office Action in Application No. 2007-506626, dated Aug. 26, 2011.
Japanese Office Action in Application No. 2007-506626, dated May 10, 2012.
Japanese Office Action in Application No. 2007-506626, dated Mar. 1, 2011.
Canadian Office Action in Application No. 2562258 mailed Jun. 22, 2012.
Gorges, M. et al., "Improving Alarm Performance in the Medical Intensive Care Unit Using Delays and Clinical Context"; Technology, Computing, and Simulation; vol. 108, No. 5, May 2009; p. 1546-1552.
Images showing tear down of a Measurement Specialties' stethoscope, Images taken on Sep. 7, 2007, in 38 pages.
Imhoff, M. et al., "Alarm Algorithms in Critical Care Monitoring"; Anesth Analg 2006;102:1525-37.
International Preliminary Report on Patentability for PCT/US2010/058981 dated Jun. 5, 2012.
International Preliminary Report on Patentability in PCT/US2010/052754 mailed Apr. 26, 2012.
International Preliminary Report on Patentability in US/2010/052756 mailed Apr. 26, 2012.
International Preliminary Report on Patentability in US/2010/052758 mailed Apr. 17, 2012.
International Preliminary Report on Patentability in US/2010/052760 mailed Apr. 17, 2012.
International Preliminary Report on Patentability in US/2010/052763 mailed Apr. 17, 2012.
International Search Report and Written Opinion in PCT/US2009/042902, mailed Dec. 8, 2009.
International Search Report and Written Opinion in PCT/US2010/052754, mailed Jul. 27, 2011.
International Search Report and Written Opinion in PCT/US2010/052756, mailed Feb. 6, 2012.
International Search Report and Written Opinion in PCT/US2010/052763, mailed May 13, 2011.
International Search Report and Written Opinion in PCT/US2009/069287, mailed Jun. 30, 2010, in 22 pages.
International Search Report and Written Opinion in PCT/US2010/052760, mailed Mar. 8, 2011 in 11 pages.
PCT Invitation to Pay Fees and Initial Search Report in PCT/US2010/052754, dated Mar. 15, 2011.
Sierra, G., et al.: "Monitoring Respiratory Rate Based on Tracheal Sounds. First Experiences", Proceedings of the 26th Annual International Conference of the IEEE EMBS, Sep. 2004, pp. 317-320.
Supplemental Partial European Search Report for EP Application No. 05732095.4, dated Jun. 26, 2009 in 4 pages.
Watt, R. C., "Alarms and Anesthesia. Challenges in the design of Intelligent systems for Patient Monitoring"; IEEE Engineering in Medicine and biology; Dec. 1993, p. 34-41.

WelchAllyn OEM Technologies, ECG ASIC, ECG 3-lead, 5-lead, 12-lead and RESP Signal Processing, ECG ASIC Part No. 000.91163 (2001).
Burritt, Mary F.; Current Analytical Approaches to Measuring Blood Analytes; vol. 36; No. 8(B); 1990.
European Examination Report dated Apr. 1, 2010, re EP App. No. 08 744 412.1-2319.
European Examination Report dated Mar. 18, 2011, re EP App. No. 08 744 412.1-2319.
European Examination Report dated Sep. 2, 2010, re EP App. No. 08 744 412.1-2319.
European Examination Report, re EP Application No. 12163719.3, dated Feb. 6, 2013.
European Extended Search Report of European Application No. 12163719.3, dated of Jun. 18, 2012, in 6 pages.
European Extended Search Report re EPO App. No. 10162402.1, SR dated Aug. 9, 2010.
European Office Action re EP Application No. 06 736 799.5, dated Nov. 30, 2012.
European Search Report, re EP Application No. 10 19 1029, dated Jun. 5, 2012.
Hall, et al., Jeffrey W.; Near-Infrared Spectrophotometry: A New Dimension in Clinical Chemistry; vol. 38; No. 9; 1992.
International Search Report and Written Opinion, re PCT App. No. PCT/US2006/007506, dated Jul. 17, 2006.
International Search Report for PCT/US2006/007516, mailed on Jan. 11, 2007, in 4 pages.
International Search Report of International Application No. PCT/US2008/058327, Mailing Date of Jun. 30, 2009, in 12 pages.
International Search Report; PCT/US2006/007389; Date of Mailing Jul. 17, 2006; pp. 1-9.
International Search Report; PCT/US2006/007506; Date of Mailing Jul. 17, 2006; pp. 1-10.
International Search Report; PCT/US2006/007539; Date of Mailing Jul. 17, 2006; pp. 1-9.
International Search Report; PCT-US2006-007387; Date of Mailing Jul. 17, 2006; pp. 1-9.
International Search Report; PCT-US2006-007388; Date of Mailing Jul. 17, 2006; pp. 1-9.
International Search Report; PCT-US2006-007536; Date of Mailing Jul. 17, 2006; pp. 1-9.
International Search Report; PCT-US2006-007537; Date of Mailing Jul. 17, 2006; pp. 1-10.
International Search Report; PCT-US2006-007538; Date of Mailing Jul. 17, 2006; pp. 1-9.
International Search Report; PCT-US2006-007540; Date of Mailing Jul. 17, 2006; pp. 1-9.
International Search Report; PCT-US2006-007958; Date of Mailing Jul. 17, 2006; pp. 1-8.
Japanese Final Office Action re Amendments re JP Application No. 2007-558249, dated Apr. 17, 2012.
Japanese First Office Action (Notice of Reasons for Rejection), re JP App. No. 2007-558207, dated Jun. 28, 2011.
Japanese First Office Action (Notice of Reasons for Rejection), re JP App. No. 2007-558247, dated Jun. 28, 2011.
Japanese Office Action (Decision of Rejection), re JP Application No. JP 2007-558328, dated Jun. 25, 2013.
Japanese Office Action (Notice of Allowance), re JP App. No. 2007-558247, dated Oct. 24, 2011.
Japanese Office Action (Notice of Reasons for Rejection) re JP App. No. 2007-558246, dated Jun. 28, 2011.
Japanese Office Action (Notice of Reasons for Rejection), re JP App. No. 2007-558238, dated Jun. 28, 2011.
Japanese Office Action (Official Inquiry) re JP App. No. 2007-558246, dated Dec. 11, 2012.
Japanese Office Action (Official Inquiry), re JP App. No. 2007-558238/Appeal No. 2012-004053, dated Dec. 11, 2012.
Japanese Office Action (Reasons for Rejection) re JP App. No. 2007-558246, dated Nov. 1, 2011.
Japanese Office Action re JP Application No. 2007-558249, dated Aug. 28, 2012.
Japanese Office Action re JP Application No. 2007-558249, dated Jul. 19, 2011.

(56) References Cited

OTHER PUBLICATIONS

Japanese Office Action re JP Application No. 2007-558249, dated Nov. 8, 2011.
Japanese Office Action re JP Application No. JP 2007-558208, dated Aug. 23, 2011.
Japanese Office Action re JP Application No. JP 2007-558248, dated Nov. 27, 2012.
Japanese Office Action re JP Application No. JP 2007-558248, dated Nov. 8, 2011.
Japanese Office Action re JP Application No. 2007-558209, dated Oct. 25, 2011.
Japanese Office Action re JP Application No. 2007-558209, dated Oct. 30, 2012.
Japanese Office Action re JP Application No. 2007-558245, dated Jan. 15, 2013.
Japanese Office Action re JP Application No. 2007-558245, dated Oct. 25, 2011.
Japanese Office Action, re JP Application No. 2007-558237, dated Aug. 2, 2011.
Japanese Office Action, re JP Application No. 2012-045419, dated Jun. 26, 2012.
Japanese Office Action, re JP Application No. JP 2007-558237, dated Oct. 16, 2012.
Kuenstner, et al., J. Todd; Measurement of Hemoglobin in Unlysed Blood by Near-Infrared Spectroscopy; vol. 48; No. 4, 1994.
Manzke, et al., B., Multi Wavelength Pulse OXimetry in the Measurement of Hemoglobin Fractions; vol. 2676, date unknown.
Naumenko, E. K.; Choice of Wavelengths for Stable Determination of Concentrations of Hemoglobin Derivatives from Absorption Spectra of Erythrocytes; vol. 63; No. 1; pp. 60-66 Jan.-Feb. 1996; Original article submitted Nov. 3, 1994.
Schmitt, Joseph M.; Simple Photon Diffusion Anaylsis of the Effects of Multiple Scattering on Pulse Oximetry; Mar. 14, 1991; revised Aug. 30, 1991.
Schmitt, Joseph M.; Zhou, Guan-Xiong; Miller, Justin, Measurement of Blood Hematocrit by Dual-wavelength Near-IR Photoplethysmography, published May 1992, Proc. SPIE vol. 1641, p. 150-161, Physiological Monitoring and Early Detection Diagnostic Methods, Thomas S. Mang; Ed. (SPIE homepage), in 12 pages.
Schnapp, et al., L.M.; Pulse Oximetry. Uses and Abuses.; Chest 1990; 98; 1244-125000110.1378/Chest.98.5.1244.

* cited by examiner

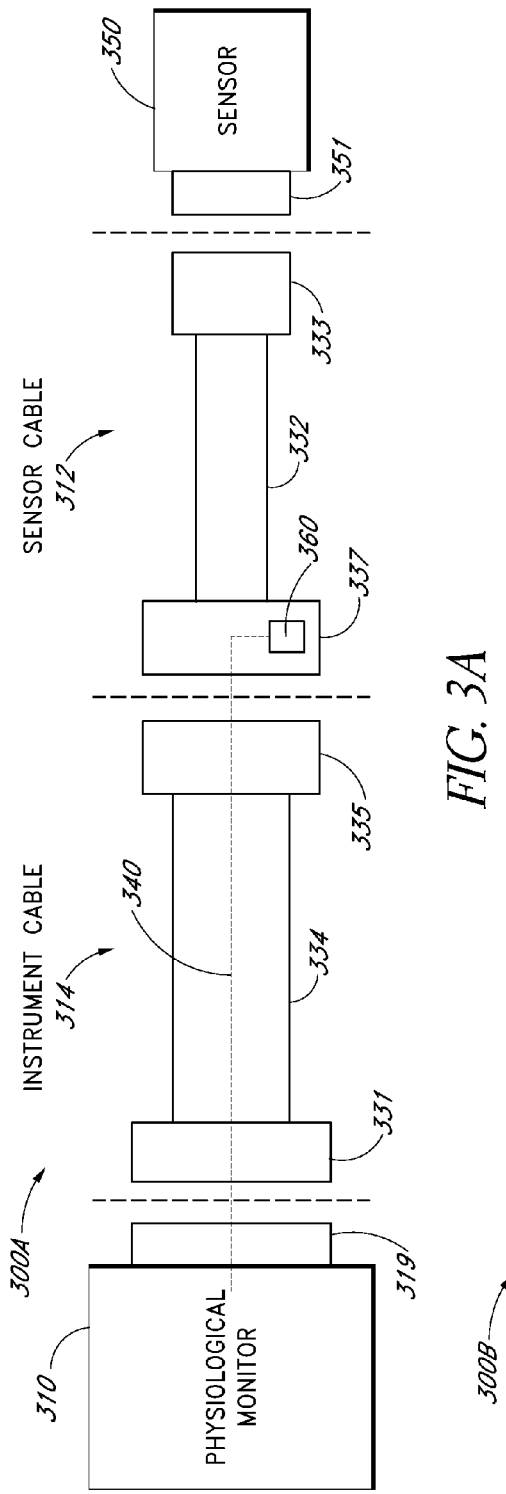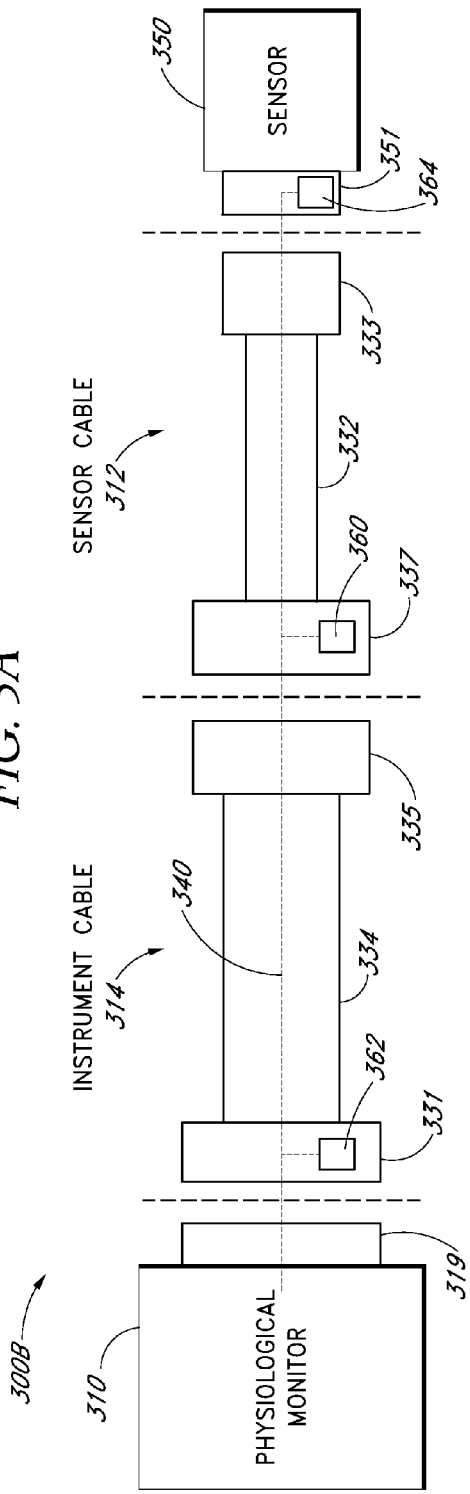

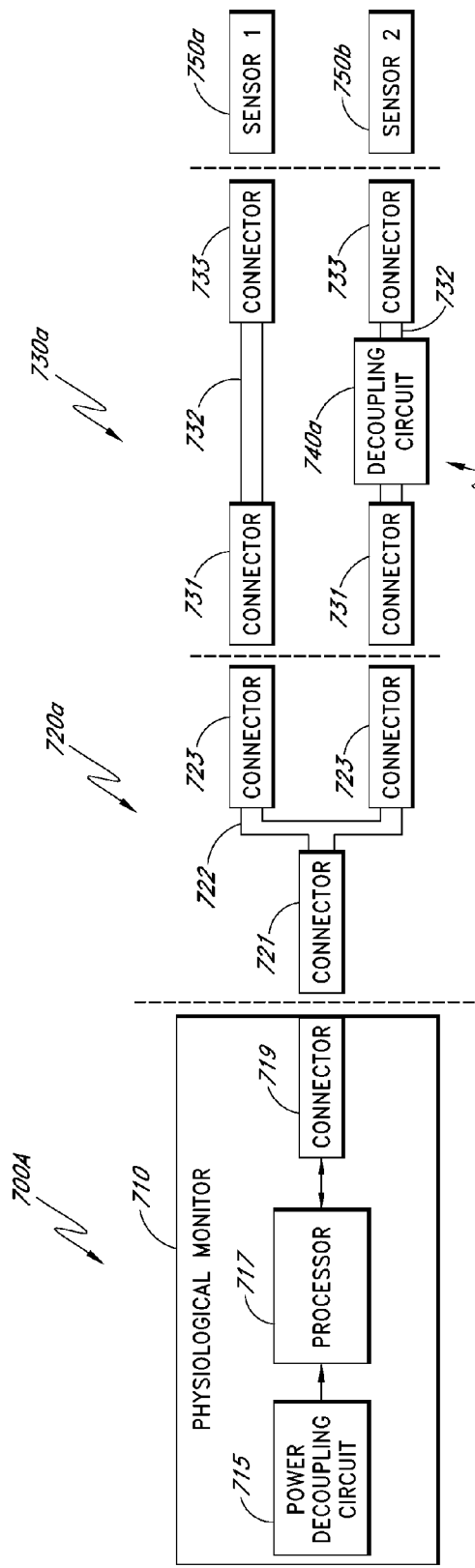
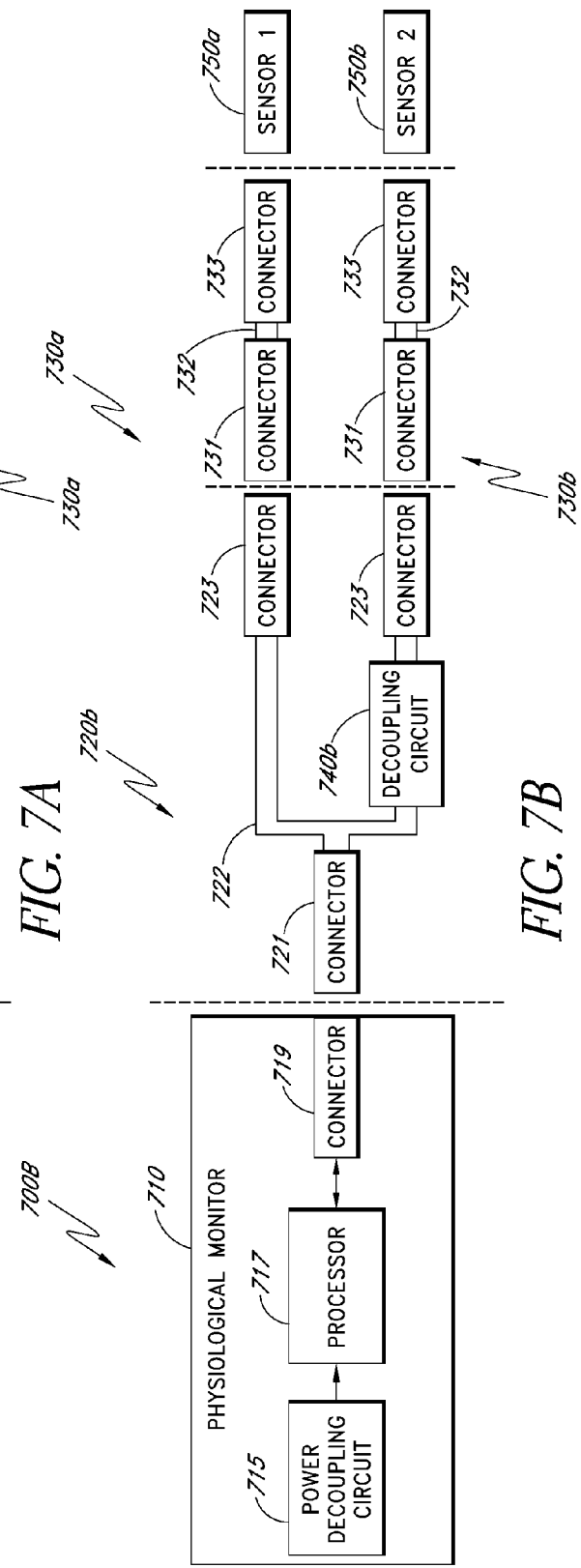
FIG. 7A
FIG. 7B

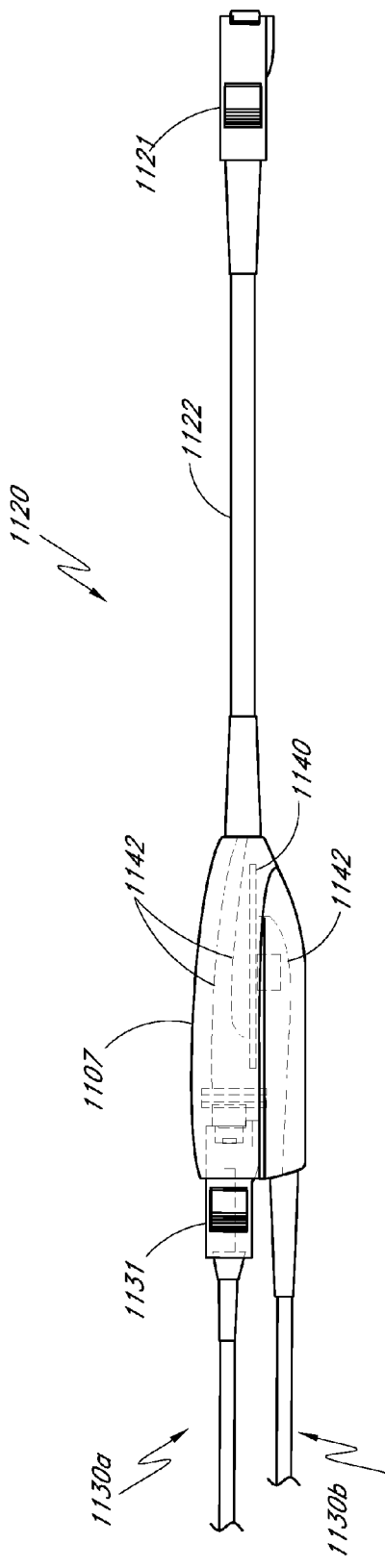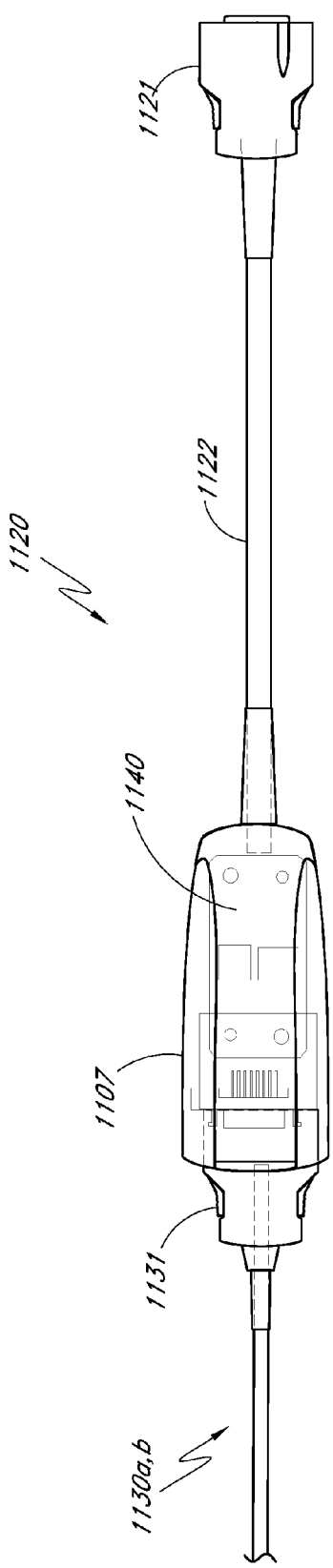
FIG. 11A
FIG. 11B

CALIBRATION FOR MULTI-STAGE PHYSIOLOGICAL MONITORS

RELATED APPLICATIONS

This application claims priority from U.S. Provisional Patent Application No. 61/266,984, filed Dec. 4, 2009, and entitled "Automatic Calibration for Multi-Stage Physiological Monitors."

Additionally, this application relates to the following U.S. patent applications, the disclosures of which are incorporated in their entirety by reference herein:

| App. No. | Filing Date | Title |
| --- | --- | --- |
| 60/893853 | Mar. 08, 2007 | MULTI-PARAMETER PHYSIOLOGICAL MONITOR |
| 60/893850 | Mar. 08, 2007 | BACKWARD COMPATIBLE PHYSIOLOGICAL SENSOR WITH INFORMATION ELEMENT |
| 60/893858 | Mar. 08, 2007 | MULTI-PARAMETER SENSOR FOR PHYSIOLOGICAL MONITORING |
| 60/893856 | Mar. 08, 2007 | PHYSIOLOGICAL MONITOR WITH FAST GAIN ADJUST DATA ACQUISITION |
| 12/044883 | Mar. 08, 2008 | SYSTEMS AND METHODS FOR DETERMINING A PHYSIOLOGICAL CONDITION USING AN ACOUSTIC MONITOR |
| 61/252083 | Oct. 15, 2009 | *DISPLAYING PHYSIOLOGICAL INFORMATION* |
| 12/904836 | Oct. 14, 2010 | *BIDIRECTIONAL PHYSIOLOGICAL INFORMATION DISPLAY* |
| 12/904823 | Oct. 14, 2010 | *BIDIRECTIONAL PHYSIOLOGICAL INFORMATION DISPLAY* |
| 61/141584 | Dec. 30, 2008 | *ACOUSTIC SENSOR ASSEMBLY* |
| 61/252076 | Oct. 15, 2009 | *ACOUSTIC SENSOR ASSEMBLY* |
| 12/643939 | Dec. 21, 2009 | *ACOUSTIC SENSOR ASSEMBLY* |
| 61/313645 | Mar. 12, 2010 | *ACOUSTIC RESPIRATORY MONITORING SENSOR HAVING MULTIPLE SENSING ELEMENTS* |
| 12/904931 | Oct. 14, 2010 | *ACOUSTIC RESPIRATORY MONITORING SENSOR HAVING MULTIPLE SENSING ELEMENTS* |
| 12/904890 | Oct. 14, 2010 | *ACOUSTIC RESPIRATORY MONITORING SENSOR HAVING MULTIPLE SENSING ELEMENTS* |
| 12/904938 | Oct. 14, 2010 | *ACOUSTIC RESPIRATORY MONITORING SENSOR HAVING MULTIPLE SENSING ELEMENTS* |
| 12/904907 | Oct. 14, 2010 | *ACOUSTIC PATIENT SENSOR* |
| 61/252062 | Oct. 15, 2009 | *PULSE OXIMETRY SYSTEM WITH LOW NOISE CABLE HUB* |
| 61/265730 | Dec. 01, 2009 | *PULSE OXIMETRY SYSTEM WITH ACOUSTIC SENSOR* |
| 12/904775 | Oct. 14, 2010 | *PULSE OXIMETRY SYSTEM WITH LOW NOISE CABLE HUB* |
| 12/905036 | Oct. 14, 2010 | *PHYSIOLOGICAL ACOUSTIC MONITORING SYSTEM* |
| 61/331087 | May 04, 2010 | *ACOUSTIC RESPIRATION DISPLAY* |
| 61/391098 | Oct. 08, 2010 | *ACOUSTIC MONITOR* |

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters. Physiological parameters include, for example, respiratory rate, oxygen saturation ($SpO_2$) level, pulse, and blood pressure, among others. Clinicians, including doctors, nurses, and certain other medical personnel, use the physiological parameters obtained from the medical patient to diagnose illnesses and to prescribe treatments. Clinicians also use the physiological parameters to monitor a patient during various clinical situations to determine whether to increase the level of medical care given to the patient.

Many monitoring devices receive physiological signals from one or more sensors, such as pulse oximetry sensors, other types of optical sensors, acoustic sensors, and the like. Medical cables attached to the sensors transmit signals from the sensors to the monitoring device.

Physiological signals in some monitoring systems can be relatively small or otherwise difficult to measure with a high degree of accuracy. As such, manufacturing tolerances for the various components in the system may be relatively tight, possibly leading to low yields, increased manufacturing cost and/or reduced flexibility in component design.

Additionally, sensors, cables and other components in the sensor path may be sold with a specific monitoring device and are factory calibrated for use with only that monitoring device, reducing flexibility in component selection. Alternatively, some systems may be manually calibrated in the field, increasing cost and setup time. Accordingly, there remains a need for a monitoring system capable of providing accurate physiological measurement while addressing these and other issues.

SUMMARY

According to certain aspects, a physiological monitor is provided for determining a physiological parameter of a medical patient with a multi-stage sensor assembly. The physiological monitor can include a signal processor configured to receive a signal indicative of a physiological parameter of a medical patient from a multi-stage sensor assembly. The multi-stage sensor assembly can be configured to be attached to the physiological monitor and the medical patient. The physiological monitor can further include an information element query module configured to obtain calibration information from an information element provided in a plurality of stages of the multi-stage sensor assembly. In certain embodiments, the signal processor is configured to determine the physiological parameter of the medical patient based upon said signal and said calibration information.

A method of determining a physiological parameter of a medical patient with a physiological monitor is provided according to certain aspects. The method may include receiving a signal indicative of a physiological parameter of a medical patient from a multi-stage sensor assembly. In some embodiments, the method further includes obtaining calibration from an information element provided in a plurality of stages of the multi-stage sensor assembly. The method can further include determining the physiological parameter of the medical patient based upon the signal and the calibration information.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIGS. 3A and 3B illustrate block diagrams of example monitoring systems that include one or more information elements usable for multi-stage calibration, according to certain embodiments;

FIGS. 7A and 7B illustrate block diagrams of example physiological monitoring systems having splitter cables;

FIG. 11A illustrates a side view of an example splitter cable;

FIG. 11B illustrates a bottom view of the example splitter cable of FIG. 6A;

DETAILED DESCRIPTION

Figure 1:
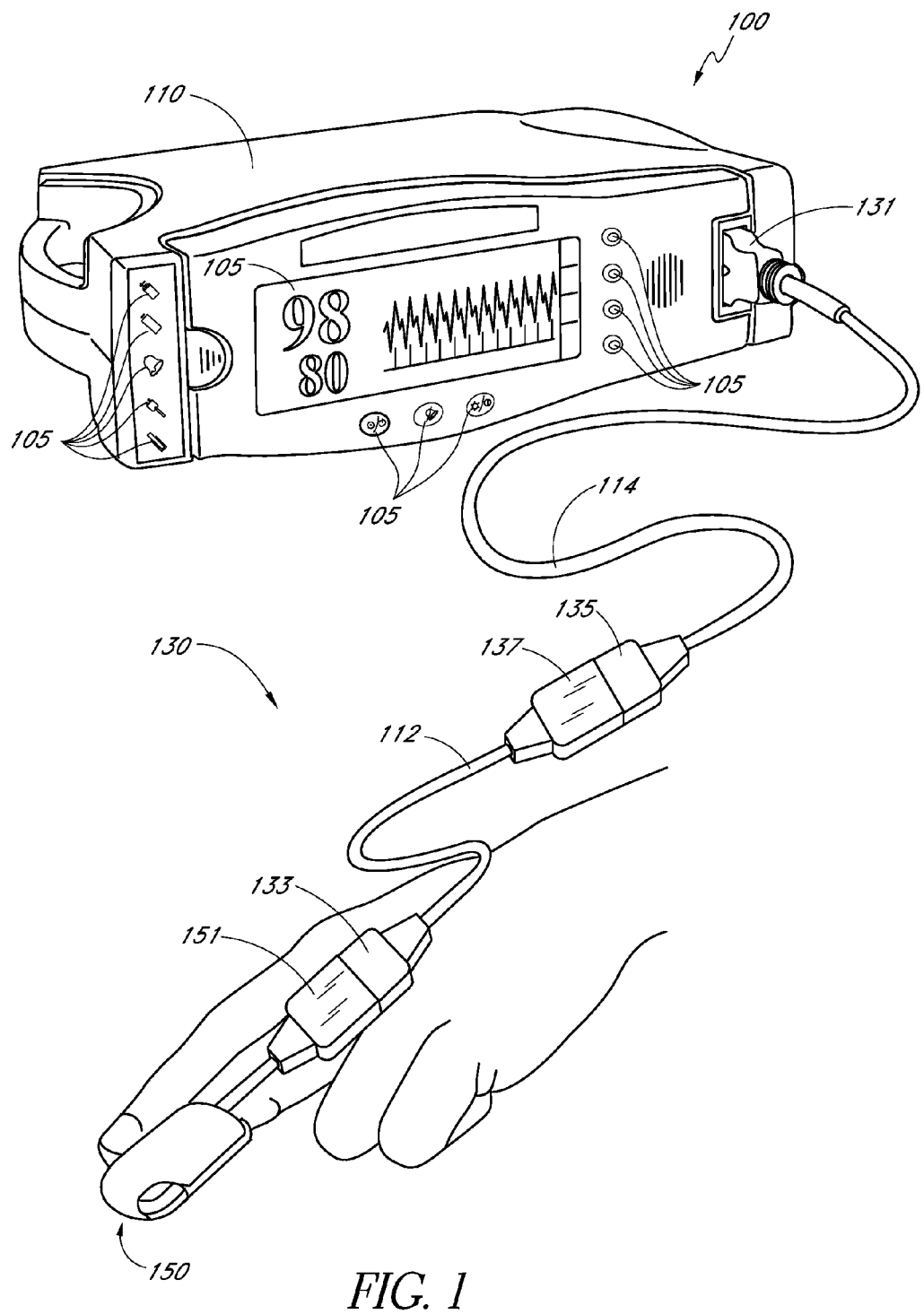
FIG. 1 illustrates a perspective view of an embodiment of a physiological monitoring system.

Systems described herein include various components, such as one or more cables, front end processing circuitry, and the like, interposed in the path between the sensor and signal processing circuitry in a monitoring device. The sensor and these components or portions thereof may be described as stages in the sensor path. Systems described herein may accordingly be referred to as multi-stage systems.

Multi-Stage Calibration Overview

Each stage in the sensor path has particular behavioral characteristics defining a response for that stage. Generally, each stage receives a version of the detected sensor signal and produces a modified version of that signal according to a characteristic response of the respective stage. The behavioral characteristics defining the characteristic responses of the stages can include a variety of parameters such as electrical properties (e.g., capacitances, impedances, etc.), mechanical properties, response characteristics (e.g., frequency responses, gain characteristics, etc.), among others. Information relating to these characteristics may be referred to through this disclosure interchangeably as calibration information, behavioral information and behavioral characteristic information, for example.

Due to inconsistencies in manufacture, materials, etc., certain behavioral characteristics and corresponding calibration information can vary significantly between components of the same type. Characteristics subject to these types of inconsistencies may be referred to as process variable characteristics as they are dependent on material or manufacturing inconsistencies. It is generally desirable for a monitoring system to be able to cooperate with components having as wide a range of process variable characteristics as possible. For example, manufacturing tolerances can be expanded as a result, leading to improved accuracy and repeatability, higher yields and reduced cost.

In addition to process variable characteristics, design variable characteristics can arise based on various component design schemes and associated parameters. Because they are based on known design choices, design variable characteristics are generally predetermined, unlike process variable characteristics.

As one example of a scenario involving design variable characteristics, an acoustic sensor of a first design scheme may include design characteristics optimized to use relatively low amplitude signals, such as for use with patients having a particularly shallow breath or to detect a certain type of relatively quiet physiological sound. Design choices for this sensor are tailored for such a use. For example, a relatively sensitive material may be used for the sensing element (e.g., a piezoelectric film), or the sensing element may be manufactured for relatively high sensitivity. Moreover, programmable variables such as gain settings may be set to a relatively high level. On the other hand, an acoustic sensor according to a second design may be optimized to detect relatively louder physiological sounds. For this sensor, different design parameters are used such as a relatively less sensitive sensing element, lower gain settings, etc. Beyond this illustrative example, a broad universe of design variable characteristics associated with monitoring systems exists, such as design variable characteristics associated with non-sensor components (e.g., cables, processing circuitry, etc.) or those related to other types of sensors (e.g., optical sensors such as $SpO_2$ sensors).

It is desirable for monitoring systems to be able to adapt to components having generally as wide a range of design variable characteristics as possible. For example, this can allow system designers to develop an array of components that are customized for particular applications.

Systems described herein are advantageously capable of accounting for process characteristic variability and/or design characteristic variability, allowing for system calibration (e.g., automatic calibration) based on the properties of the particular attached components. This calibration technique may be referred to interchangeably throughout this disclosure as automatic, dynamic, adaptive, or intelligent calibration. In some embodiments, the process may also be referred to as sensor path or signal acquisition, or as having an equalization effect on the sensor signal, for example. These terms are used for the purpose of illustration and are not intended to be limiting. In some other embodiments, at least a portion of the calibration process is achieved manually.

According to some embodiments, one or more of the stages in the sensor path has at least one information element storing calibration information relating to that stage. The calibration information may be determined and stored, such as during manufacture. For example, a test signal may be injected into a component such as a physiological sensor. Various characteristics such as frequency responses, capacitances, etc., of the sensor may be measured using the test signal and are stored in an information element on the sensor. Additionally, certain predetermined characteristics, which may primarily include design variable characteristics, may be stored on the information element without any separate calibration process.

According to certain embodiments, the monitoring device is configured to receive the calibration information from the sensor path stages. Based on the calibration information, the monitoring device can then intelligently adjust processing of the received sensor signal, accounting for the particular behavioral properties of the attached components.

Because monitoring systems according to such embodiments can adapt to the specific properties of the attached components, these systems can provide interchangeable use with a wide variety of components. For example, these systems can be used with components having a wide range of process and/or design characteristic variability.

Allowable manufacturing tolerances can be greatly expanded. Improved manufacturing repeatability and yields are achieved, as a result while maintaining a high degree of measurement accuracy.

The multi-stage calibration capability provides a generally fully interchangeable system in which existing components can be swapped out for components of the same type or for components customized for particular purposes. This type of mix and match capability provides enhanced ease of use and can also allow for the use of disposable components, such as disposable sensor components. The use of disposable components can provide a number of advantages including improved sanitation and convenience.

For example, a user can select a sensor for use with a monitoring device from a batch of sensors of the same type without verifying that the particular sensor has been calibrated for use with that particular monitoring device. The user can additionally combine this sensor with another component, such as an instrument cable selected from a batch of instrument cables having the same type. Again, the user can attach the cable and sensor to the monitor and begin monitoring without verifying that the particular cable has been calibrated for use with that particular monitoring device or sensor.

In some cases, sensor path components can be initially characterized at the factory, and the appropriate characterization information is stored on the component. The factory calibration can advantageously be transferred to the field as clinicians deploy the components with generally any compatible system without the need for independent field calibration.

For example, in one scenario, a user first attaches a first sensor to a first cable connected to a first monitoring device. The monitoring device reads the behavioral characteristics of the components and adjusts the signal processing parameters accordingly, such as when new sensor path components are attached. The user then replaces the first sensor with a second sensor of the same type, but having different behavior characteristics, such as process variable characteristics. In another scenario, the user replaces the first sensor with a second sensor having a different type, such as a sensor tailored for a particular use, and having different design variable characteristics. In both scenarios, the monitoring device reads the behavioral characteristics of the second sensor and again performs multi-stage calibration so as to cooperate with the second sensor.

The multi-stage calibration techniques described herein can benefit physiological monitoring systems incorporating generally any type of sensor. Additionally, in part because dynamic calibration allows for improved manufacturing tolerance, they can be of particular benefit to systems which measure relatively small signals, such as those including acoustic sensors for measuring respiratory rate, heart sounds, and the like.

Further embodiments of monitoring systems capable of multi-stage calibration techniques are described below with respect to FIGS. 1 through 6, for example.

Turning to FIG. 1, an embodiment of a physiological monitoring system 100 for monitoring a medical patient is shown. The physiological monitoring system 100 can be configured to implement the multi-stage calibration techniques described herein, and includes a physiological monitor 110 coupled with a sensor assembly 150 through a cable 130. The monitor 110 includes various visual indicia and user controls 105 for displaying sensor parameters, alarms, and the like and for receiving user input. The sensor assembly 150 could include any of a variety of physiological sensors. For example, the sensor assembly 150 could include one or more optical sensors that allow the measurement of blood constituents and related parameters, acoustic respiratory sensors, electrocardiograph sensors, and the like.

More generally, the sensor assembly 150 can include one or more sensors that measure one or more of a variety of physiological parameters, including oxygen saturation, carboxyhemologbin (HbCO), methemoglobin (HBMet), fractional oxygen, total hemoglobin (HbT/SpHb), pulse rate, perfusion index, electrical heart activity via electrocardiography, and blood pressure. Other examples of physiological parameters that may be measured include respiratory rate, inspiratory time, expiratory time, inspiration-to-expiration ratio, inspiratory flow, expiratory flow, tidal volume, end-tidal $CO_2$ ($ETCO_2$), $CO_2$, minute volume, apnea duration, breath sounds, rales, rhonchi, stridor, changes in breath sounds such as decreased volume or change in airflow, heart rate, heart sounds (e.g., S1, S2, S3, S4, and murmurs), and changes in heart sounds such as normal to murmur or split heart sounds indicating fluid overload.

In some embodiments, the sensor assembly 150 can be an optical sensor having one or more emitters, such as light emitting diodes. The emitters may emit multiple wavelengths of light that impinge on body tissue of a living patient, such as a finger, foot, ear, or the like. The emitters may also emit non-visible radiation. The sensor assembly 150 may further include one or more detectors that can receive light attenuated by the body tissue of the patient. The detectors can generate physiological signals responsive to the detected light. The sensor assembly 150 can provide these physiological signals to the monitor 110 for processing to determine one or more physiological parameters, such as certain of the parameters described above. An example of such a sensor assembly 150 is described in U.S. Publication No. 2006/0211924, filed Mar. 1, 2006, titled "Multiple Wavelength Sensor Emitters," the disclosure of which is hereby incorporated by reference in its entirety.

The cable 130 is connected to the sensor assembly 150 and to the monitor 110. In some embodiments, the cable 130 includes two or more cables or cable assemblies, although it should be noted that the cable 130 can also be a single cable 130. In the illustrated embodiment, the cable 130 includes a sensor cable 112 and an instrument cable 114. The sensor cable 114 is connected directly to the sensor assembly 150 through connectors 133, 151, and the instrument cable 114 is connected directly to the monitor 110 through a connector 131. The sensor cable 112 is connected to the instrument cable 114 through connectors 135, 137.

In certain embodiments, the sensor cable 112 is a lightweight, flexible cable used for a single medical patient and disposed of after use with that patient. In contrast, the instrument cable 112 of certain embodiments is used for multiple patients and may be more durable than the sensor cable 112. For example, the instrument cable 112 may be thicker, stiffer, or heavier than the sensor cable 112. Advantageously, in certain embodiments, the lightweight, flexible characteristics of the sensor cable 112 make the sensor cable 112 more comfortable to attach to a patient. A patient with a sensor assembly 150 attached to her finger, for instance, could more easily move her hand with a lightweight sensor cable 112 attached to the sensor assembly 150. However, if some or all of the cable 130 were lightweight and flexible, it might be less durable. Hence, a portion of the cable 130 (e.g., the instrument cable 114) is stronger and more durable, yet potentially heavier and less flexible. The instrument cable 114 could therefore be used for multiple patients, while the sensor cable 112 might be used for fewer patients, such as a single patient.

While the physiological monitor 110 of FIG. 1 is shown connecting to a single sensor assembly 150, it may be advantageous in certain embodiments to connect to multiple sensors, such as sensors that monitor different physiological parameters. For instance, the physiological monitor 110 could connect to a pulse oximetry sensor and an acoustic sensor that measures respiratory rate, heart sounds, and related parameters. One way to provide multiple sensor functionality to the physiological monitor 110 is to provide a splitter cable between the monitor and the cable 130 (see FIGS. 7 and 11). A splitter cable reduces or eliminates a need to build a second cable port into the chassis of the physiological monitor 110 to accommodate a second cable 130. Consequently, using a splitter cable can reduce costs. Moreover, using a splitter cable can reduce cross-talk noise between signal lines from the sensors.

However, as described above, upgrading the physiological monitor 110 to receive input from multiple sensors using a splitter cable or the like can create electrical shock hazards to the patient due to the possibility of conductive paths forming through the sensors, cabling, and the patient. For example, if an acoustic sensor is placed on the chest and a defibrillator paddle touches the acoustic sensor, a surge of current could discharge through a conductive path formed in the patient between the acoustic sensor and a second sensor, and through the physiological monitor 110. This current surge could injure the patient and damage the monitor 110.

Consequently, various embodiments of the cable 130 or an attached splitter cable can include one or more decoupling circuits (not shown) for reducing the risk of electric shock to the patient. Each decoupling circuit can electrically decouple the sensor assembly 150 from the monitor 110 or can decouple multiple sensor assemblies 150. In addition to having its ordinary meaning, electrical decoupling can mean breaking a conductive path (e.g., by providing a dielectric between two conductors) or increasing the resistance between conductors. Electrical decoupling can be accomplished using transformers and/or optocouplers, as described below. The electrical decoupling of the decoupling circuit can prevent or reduce harmful current surges from harming the patient. Example decoupling circuits compatible with certain embodiments are provided below with respect to FIGS. 7 through 11.

In addition to including decoupling circuitry in the cable 130 or in an attached splitter cable, it may be desirable to include other circuitry in the cable 130 or splitter cable. For example, the cable 130, a splitter cable, and/or the sensor assembly 150 may include one or more information elements (not shown), which can be memory devices such as EEPROMs or the like. The information elements may further store calibration information related to one or more of the components in the system. The monitoring device may use such calibration information to calibrate a multi-stage sensor path according to embodiments described herein. Example compatible information elements are described below with respect to FIGS. 3 through 6 and 11 through 17. In some embodiments, the information element stores other information such as cable management information, patient context information, and/or physiological information.

Figure 2:
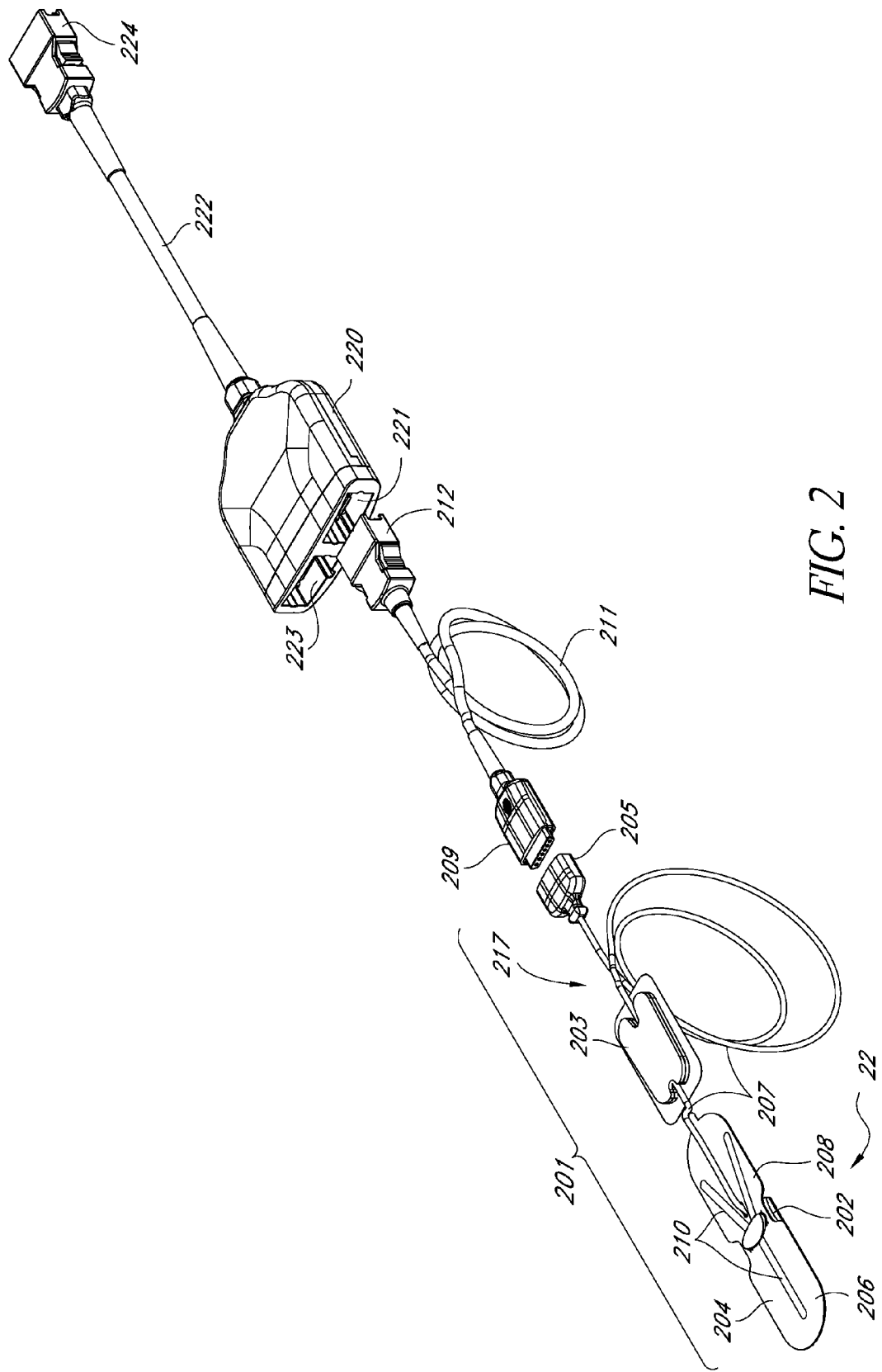
FIG. 2 is a top perspective view illustrating an embodiment of an example sensor assembly and cable.

FIG. 2 illustrates an embodiment of another sensor system capable of incorporating certain multi-stage calibration techniques described herein. The sensor system includes a sensor assembly 201, an instrument cable 211, and a hub 220 suitable for use with any of the physiological monitors and cables described herein. The sensor assembly 201 includes a sensor 215, a cable assembly 217, and a first connector 205, while the cable assembly 217 of one embodiment includes a sensor cable 207 and a patient anchor 203.

The sensor assembly 201 is removably attachable to the instrument cable 211 via the matable first and second connectors 205, 209. In turn, the instrument cable 211 can be attached to a cable hub 220, which includes a port 221 for receiving a connector 212 of the instrument cable 211 and a second port 223 for receiving another cable. The hub 220 is an example of the splitter cable described above, and as such, can include decoupling circuitry (see, e.g., FIG. 19). In certain embodiments, the second port 223 can receive a cable connected to an optical sensor (e.g., pulse oximeter) or other sensor. In addition, the cable hub 220 could include additional ports in other embodiments for receiving additional cables. The example hub 220 includes a cable 222 which terminates in a connector 224 adapted to connect to a physiological monitor (not shown).

In an embodiment, the acoustic sensor assembly 201 includes a sensing element, such as, for example, a piezoelectric device or other acoustic sensing device. The sensing element can generate a voltage that is responsive to vibrations generated by the patient, and the sensor can include circuitry to transmit the voltage generated by the sensing element to a processor for processing. In an embodiment, the acoustic sensor assembly 201 includes circuitry for detecting and transmitting information related to biological sounds to a physiological monitor. These biological sounds can include heart, breathing, and/or digestive system sounds, in addition to many other physiological phenomena. The acoustic sensor 215 in certain embodiments is a biological sound sensor, such as the sensors described or incorporated by reference herein. In some embodiments, the biological sound sensor is one of the sensors such as those described in U.S. patent application Ser. No. 12/044,883, filed Mar. 7, 2008, entitled "Systems and Methods for Determining a Physiological Condition Using an Acoustic Monitor," (hereinafter referred to as "the '883 Application"), the disclosure of which is hereby incorporated by reference in its entirety. In other embodiments, the acoustic sensor 215 is a biological sound sensor such as those described in U.S. Pat. No. 6,661,161, which is incorporated by reference herein in its entirety. Other embodiments include other suitable acoustic sensors.

The attachment mechanism 204 in certain embodiments includes first and second portions 206, 208 which can include adhesive (e.g., in some embodiments, tape, glue, a suction device, etc.). The adhesive can be used to secure the sensor 215 to a patient's skin. Moreover, one or more biasing members 210 included in the first and/or second portions 206, 208 can beneficially bias the sensor subassembly 202 in tension against the patient's skin and reduce stress on the connection between the patient adhesive and the skin. A removable backing can be provided with the patient adhesive to protect the adhesive surface prior to affixing to a patient's skin.

The sensor cable 207 can be electrically coupled to the sensor subassembly 202 via a printed circuit board ("PCB") (not shown) in the sensor subassembly 202. Through this contact, electrical signals are communicated from the multi-parameter sensor subassembly to the physiological monitor through the sensor cable 207 and the cable 211.

In various embodiments, not all of the components illustrated in FIG. 2 are included in the sensor system 200. For example, in various embodiments, one or more of the patient anchor 203 and the attachment subassembly 204 are not included. In one embodiment, for example, a bandage or tape is used instead of the attachment subassembly 204 to attach the sensor subassembly 202 to the measurement site. Moreover, such bandages or tapes can be a variety of different shapes including generally elongate, circular and oval, for example. In addition, the cable hub 220 need not be included in certain embodiments. For example, multiple cables from different sensors could connect to a monitor directly without using the cable hub 220.

Additional information relating to acoustic sensors compatible with embodiments described herein, including other embodiments of interfaces with the physiological monitor are included in applications incorporated by reference herein, such as the '883 Application, for example.

FIGS. 3A and 3B illustrate example layouts of a physiological monitoring systems 300A, 300B. FIGS. 3A and 3B illustrate various information elements 360, 362, and 364. In certain embodiments, the physiological monitoring systems 300 of FIGS. 3A and 3B implement multi-stage calibration. For example, the information elements 360, 362, and 364 can store calibration information usable to perform multi-stage calibration in accordance with embodiments described herein. The information elements 360, 362, 364 may additionally include other types of information (e.g., cable management, patient context, and/or physiological information). Although not shown, the information elements 360, 362, and 364 may also be included in any of the splitter cables described herein. Moreover, decoupling circuitry may be included in the cables of FIGS. 3A and 3B.

Referring to FIG. 3A, a physiological monitoring system 300A includes a physiological monitor 310 that communicates with a sensor 350 through an instrument cable 314 and a sensor cable 312. An information element 360 is included in the sensor cable 312.

The physiological monitor 310 interfaces with the instrument cable 314 using a connector 319, which mates with a connector 331 of the instrument cable 314. The instrument cable 314 mates in turn with the sensor cable 312 through a connector 335 on the instrument cable 314 and a corresponding connector 337 on the sensor cable 312. The sensor cable 312 in turn connects to a sensor 350 through a connector 333 and a corresponding connector 351 on the sensor 350. In alternative embodiments, the sensor cable 312 may be a splitter cable.

In the embodiment shown, the information element 360 is located in the connector 337. Other placements for the information element 360 are also possible. For example, the information element 360 could be located anywhere in the sensor 350 or in the sensor cable 312, including in a sensor cable section 332 or the connector 333. In addition, the information element 360 could also be located in the instrument cable 314 instead, or two or more information elements 360 could be used, one or more in each cable 312, 314 (see, e.g., FIG. 3).

The information element 360 can include any one or more of a wide variety of types of information elements. In an embodiment, the information element 360 is a non-volatile information element, such as, for example, an erasable programmable read-only memory ("EPROM"). "EPROM" as used herein includes its broad ordinary meaning known to one of skill in the art, including those devices commonly referred to as "EEPROM "EPROM," as well as any types of electronic devices capable of retaining their contents even when no power is applied and/or those types of devices that are reprogrammable. In an embodiment, the information element is an impedance value associated with the sensor, such as, for example, a resistive value, an impedance value, an inductive value, and/or a capacitive value or a combination of the foregoing. In addition, the cable's information element could be provided through an active circuit such as a transistor network, memory chip, flash device, or other identification device, including multi-contact single wire information elements or other devices, such as those commercially available from Dallas Semiconductor or the like. Moreover, the information element may be random access memory (RAM), read-only memory (ROM), or a combination of the same.

In an embodiment, the physiological monitor 310 communicates with the information element 360 via a serial transmission line 340. In one embodiment, the serial transmission line 340 is a multi-drop bus, although in alternative embodiments, the serial transmission line 340 is a 1-wire bus, a SCSI bus, or another form of bus. Once the physiological monitor 310 determines that it is connected to the sensor cable 312, it sends and receives signals to and from the information element 360 to access calibration information, cable management information and/or patient context information. Alternatively, the physiological monitor 310 does not access the information element 360 until requested to do so by a user (e.g., a clinician). In addition, the physiological monitor 310 may also automatically access the information element 360 or access the information element 360 in response to a user request.

FIG. 3B illustrates another embodiment of a monitoring system 300B. The monitoring system 300B preferably includes all the features of the monitoring system 300A and additionally includes an information element 362 in the instrument cable 314 and an information element 364 in the sensor 350. The information elements 362, 364 may have the same or different characteristics of the information element 360, including the same or different memory type, capacity, latency, or throughput.

In an embodiment, the serial transmission line 340 connects the physiological monitor 310 to the information element 360 in the sensor cable 312 as above. However, the serial transmission line 340 also connects to the information elements 362, 364. The physiological monitor 310 may therefore access the information elements 360, 362, 364 while running generally few transmission lines 340.

The information elements 362, 364 may have all or a portion of the functionality of the information element 360. In one embodiment, the same data is stored in each of the information elements 360, 362, 364, thereby providing data redundancy. Additionally, in such embodiments the instrument cable 314 may stay with the patient as the patient moves from one department to another, in place of or in addition to the sensor cable 312. Moreover, in one embodiment only the instrument cable 314 or the sensor assembly 350 has an information element 362 or 364, and the sensor cable 312 does not have an information element 360.

The placement of the information elements 362, 364 can be in any of a variety of locations. For example, the information element 362 may be located in either one or the connectors 331, 335 or in the instrument cable section 334. Likewise, the information element 364 of the sensor 350 may be located in the connector 351 or in another part of the sensor 350.

Although not shown, the sensor cable 312 and/or the instrument cable 314 may have multiple information elements in some embodiments. When multiple information elements are used, certain data may be stored on some information elements, and other data may be stored on others. For instance, calibration, cable management information, patient context information, physiological information, etc., or any combination thereof may be stored separate information elements.

Referring to FIG. 3B for the purposes of illustration, each of the components in the sensor path, including, for example, the sensor 350, the sensor cable 314 and the instrument cable 312 form one or more stages. Additionally, each stage can have a respective information element 364, 360, 362 associated with it.

One or more additional stages may be located in the monitor 310. For example, The monitor 310 can further include one or more components (e.g., front-end processing circuitry) and one or more information elements (not shown) storing calibration information related to those components. Example front end processing circuitry is described below with respect to FIG. 5. Further additional stages may be included, or one or more of the stages shown in FIG. 3B may not be included in certain embodiments.

The instrument cable 314 may include a splitter cable such as any of the splitter cables described herein. Additionally, in some embodiments, the sensor includes an integrated cable which connects to the sensor cable 312. Such a configuration is shown in FIG. 2, discussed above. For example, referring to FIG. 2, information elements storing calibration information may be included on one or more of the sensor assembly 201, the monitor cable 211 and the hub 220.

The monitor 310 includes at least one processor (not shown) such as any of those described herein which receives the signal detected by the sensor after it has gone through each of the stages. Thus, the signal or signals received by the processor has been modified according to the characteristic responses of each of the stages. The processor performs signal processing on the received signal to extract signals representative of one or more physiological parameters, such as any of the parameters described herein (e.g., respiratory rate, SpO$_2$, etc.).

In certain embodiments, the system 300B is further configured for calibration of the multi-stage signal path. The information elements store calibration information related to behavioral characteristics of one or more of the stages such as the sensor 350, the sensor cable 312, the instrument cable 314, and/or front-end processing circuitry in the monitor. Using the calibration information, the monitor 310 is configured to adjust the processing of the received signal or signals so as to account for the specific behavioral characteristics of the stages. Thus, the system dynamically accesses predetermined response information related to the attached components and can produce accurate measurements generally regardless of the variable characteristics of those components.

For example, in some embodiments the calibration information from each information element corresponds to a characteristic response of a corresponding stage or portions of that stage. Alternatively, the calibration information may not be directly representative of the response and the processor instead derives the response from the calibration information.

In some embodiments, the processor performs the inverse of the response of one or more of the stages to calibrate the system, although other suitable computations can be employed. In some embodiments, the processor determines a transfer function associated with one or more of the stages or portions thereof and performs the inverse transfer function to reconstruct the signal.

A multi-stage calibration module running on the processor may perform the calibration process, for example. The calibration module in some embodiments operates on the signal received from the final stage in the signal path before other signal processing is performed on the signal. In another embodiment, the multi-stage calibration is performed substantially in parallel with other signal processing. In one embodiment, the calibration module reconstructs the original sensor signal. For example, the calibration module generates a signal substantially representative of the voltage or current signal output by the sensor, removing the effects of the other components in the sensor path.

In one embodiment, rather than computing and compensating for the response of each stage individually, the processor uses the calibration information from all of the stages to determine a single combined multi-stage response. The processor can then automatically calibrate the signal processing algorithm based on the combined response, such as by performing the inverse of the combined response or by performing some other suitable computation.

In certain embodiments, one or more of the systems 300A, 300B of FIGS. 3A and 3B are configured to calibrate the processing of the sensor signal in response to calibration information stored on one or more of the information elements 362, 360, 364 and/or one or more other information elements in the sensor path.

In some embodiments, the system 300B may be capable of performing targeted noise compensation by reducing the effect of noisy components in the signal path. For example, the system of some embodiments identifies certain components or portions thereof which are contributing a relatively high amount of noise and adjusts the processing of the sensor signal accordingly. For example, the system 300B may identify and/or compensate for relatively high noise stages by manipulating the responses (e.g., transfer functions) associated with the corresponding stages during signal processing. One or more of the components can have programmable operating values, and the system may adjust one or more of those programmable values to identify and/or compensate for relatively high noisy stages.

As described, other types of information in addition to calibration information can be stored on one or more of the information elements. For example, cable management information that may be stored on the information element 360 may include information on cable usage, sensor usage, and/or monitor usage. Cable usage data may include, for example, information on the time the cable has been in use, enabling the physiological monitor 310 to determine when the sensor cable 312 is near the end of its life. Sensor usage data may include, for example, information on what sensors have been attached to the sensor cable 312, for how long, and the like. Similarly, monitor usage data may include, for example, information on what monitors have been attached to the sensor cable 312, for how long, and the like. More detailed examples of cable management information are described below, with respect to FIG. 4.

Patient context information that may be stored on the information element 360 may include patient identification data and patient flow data. In one example embodiment, patient identification data includes at least the patient's name and one or more identification numbers. Patient flow data may include, for example, details regarding the departments the patient has stayed in, the length of time therein, and devices connected to the patient. More detailed examples of patient context information may also be found below, with respect to FIG. 4.

Advantageously, in certain embodiments, the physiological monitor 310 uses the cable management information in various embodiments to determine when to replace a cable in order to prevent cable failure. The physiological monitor 310 may also use the information element 360 to track sensor 350 and physiological monitor 310 use. Some implementations of the physiological monitor 310 enable the physiological monitor 310 to transmit some or all of the cable management information to a central nurses' station or to a clinician's end user device, such as is described in further detail with respect to FIG. 4. In some implementations, the physiological monitor 310 or a central nurses' station sends an alarm to the end user device that alerts the user to impending cable failure. For example, a clinician might receive an alarm notification on a personal digital assistant (PDA), pager, or the like, which enables the clinician to replace the cable before it fails. Patient context information, including identification information, may also be provided along with the alarm to help the clinician identify the cable with the patient.

Figure 13:
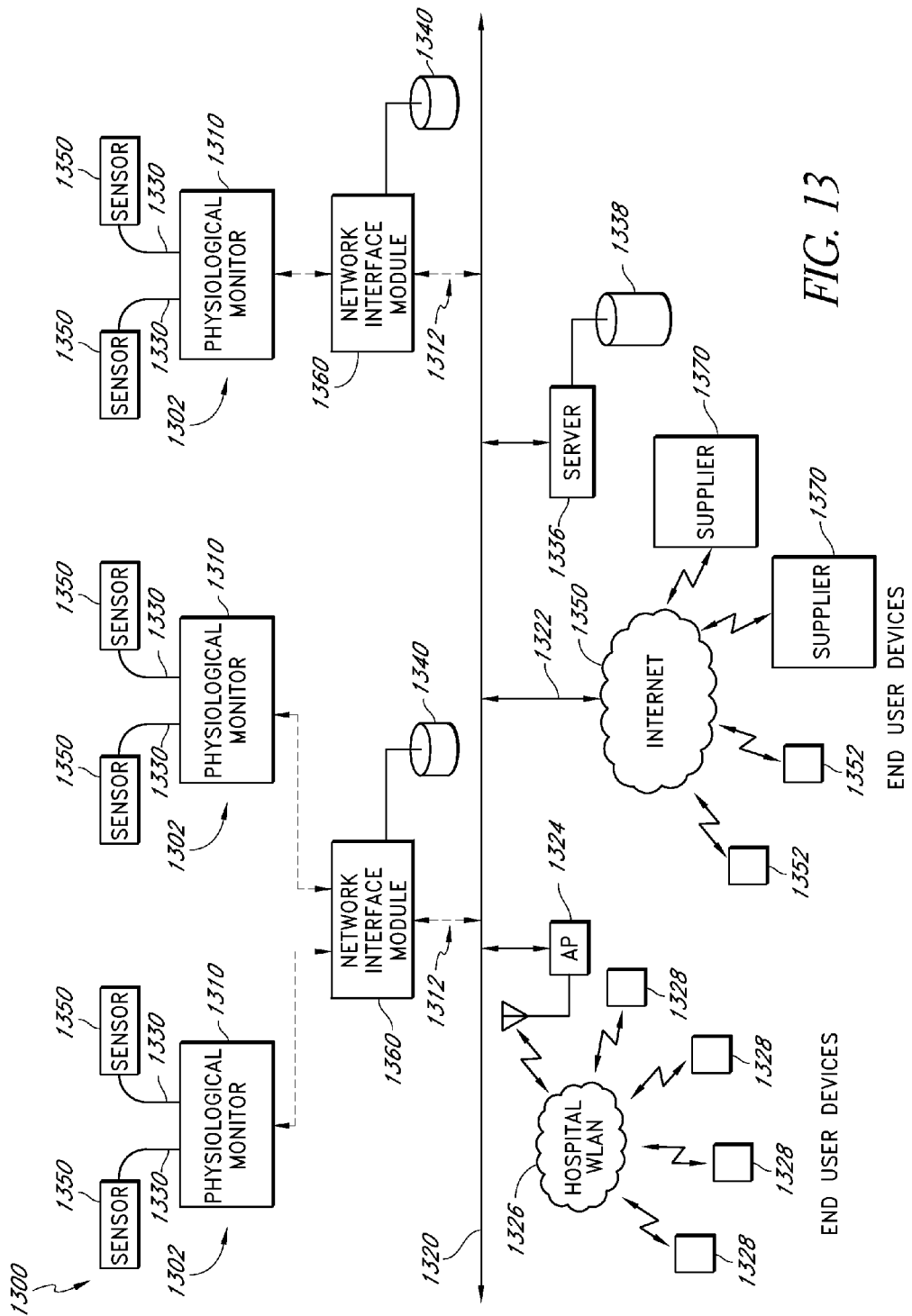
FIG. 13 illustrates an embodiment of a physiological monitoring system having multiple networked physiological monitors.

Moreover, the physiological monitor 310 may transmit some or all of the cable management information and/or patient context information to a central server (see, e.g., FIG. 13). Inventory software on the central server can use this information to preemptively order new cables when cable inventory is low or at other times.

Different sensors 350 and physiological monitors 310 may be attached to the same sensor cable 312. Thus, the cable management information may also include a list of which sensors 350 and physiological monitors 310 have been attached to the cable 312, how long they were attached, and the like. The physiological monitor 310 may also provide this information to the central server to keep track of or journal this information. The cable management information is therefore used in some embodiments to derive patient monitoring metrics, which may be analyzed to monitor or improve hospital operations. A hospital may use these metrics, for example, to determine when to replace cables or to determine whether personnel are using the cables improperly or are damaging the cables through improper use.

The patient context information in some embodiments also enables the sensor cable 312 to be identified with a particular patient. As the sensor cable 312 of some embodiments may be transported with the patient when the patient is moved about the hospital, when the sensor cable 312 is attached to different monitors 350, the data stored in the information element 360 may be transferred to the new monitor 350. Thus, during the patient's stay at the hospital or at discharge, the information element 360 of certain embodiments has patient flow data that a hospital can use to monitor or improve operations. The flow data of multiple patients may be used, for instance, to determine the number of patients staying in a particular department at a given time and the equipment used during those patients' stay. Knowing this information, the hospital can adjust equipment inventories and staff assignments to more efficiently allocate hospital resources among the various departments.

Figure 3C:
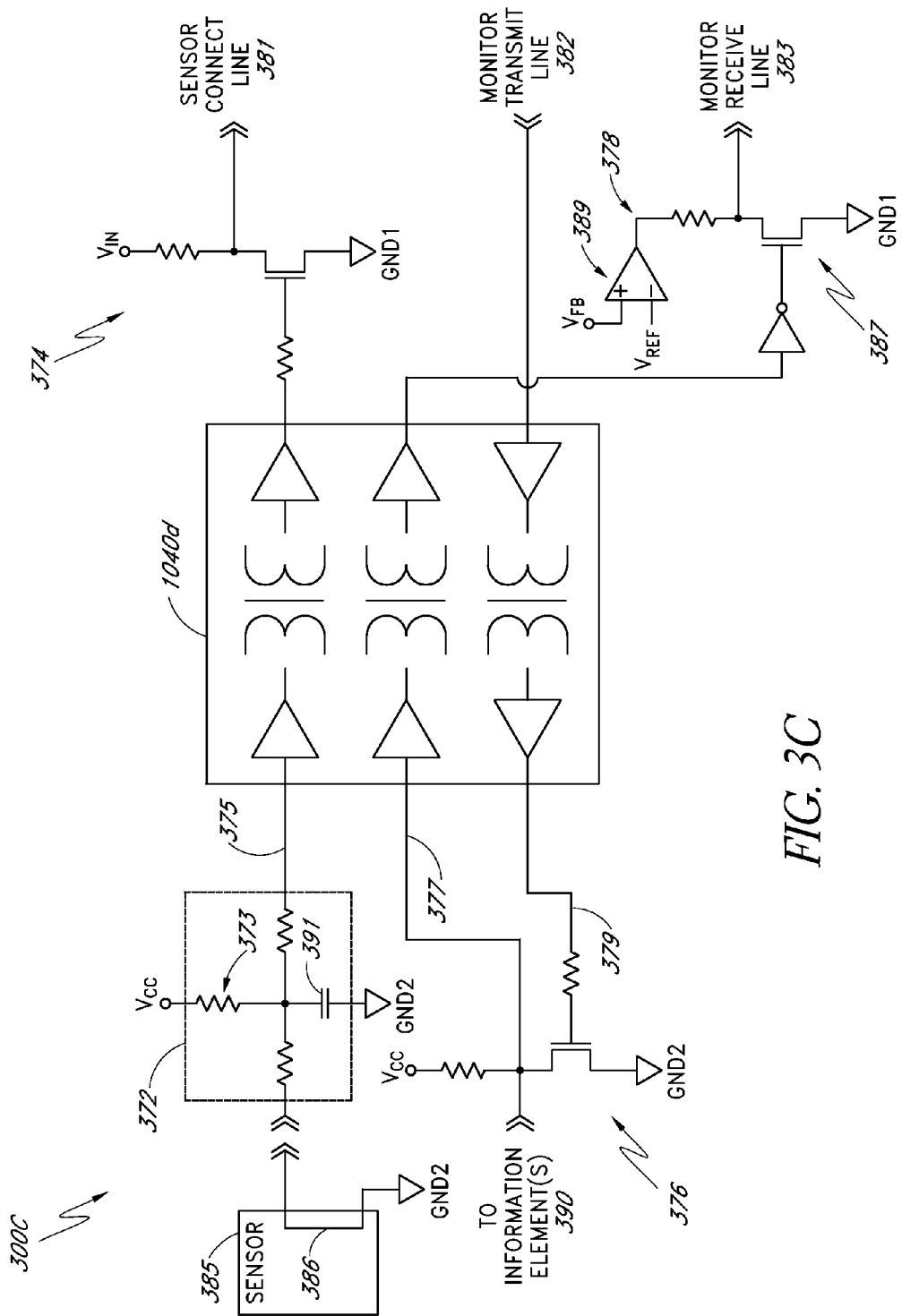
FIG. 3C illustrates an embodiment of a circuit for communicating with one or more information elements and a sensor.

FIG. 3C illustrates an embodiment of a circuit 300C for facilitating communication between a monitor and one or more information elements 390. The circuit 300C may be included in any of the cable or sensor assemblies described above, including in a splitter cable, a non-splitter cable, an instrument cable, a sensor cable, a sensor assembly, combinations of the same, and the like. In addition, the circuit 300C may be used in conjunction with the circuits 500B and 500C in a single cable, e.g., on the same circuit board, or in combination with multiple cables and/or sensor assemblies.

Advantageously, in certain embodiments, the circuit 300C provides electrical decoupling for communications lines 377, 379, 382, and 383, which provide communications between a monitor and one or more information elements. In addition, the circuit 300C may provide sensor connection status to a monitor via a sensor detect circuit 372.

A decoupling circuit 540d shown includes digital decoupling logic to electrically decouple one or more information elements and one or more sensors from the monitor. The decoupling circuit 540d includes transformers on a chip and associated logic that perform digital decoupling. In one embodiment, the decoupling circuit 540d is a ADuM130x series chip from Analog Devices. In other embodiments, optocouplers and/or other transformers are used.

Communications lines 382, 383 allow the monitor to transmit and receive data to and from one or more information elements 390. The line 382 is a monitor transmit line 382, and the line 383 is a monitor receive line 383. Each of these lines 382, 383 is electrically decoupled from the communications line 377 by the decoupling circuit 540d. The communication lines 377, 379 may be electrically coupled with the one or more information elements 390.

In an embodiment, the communications line 377 is a bus, such as a 1-wire bus. The communications line 377 may be used to both transmit and receive data to and from the monitor. The communications line 379 may be used to receive data from the monitor. A MOSFET switch 376 or the like is in communication with the depicted communications line 379, which selectively transmits signals to the one or more information elements 390.

The monitor receive line 383 is in communication with a power validation circuit 378, which determines whether the feedback power VFB described above with respect to FIG. 3C is high enough. If the feedback power VFB is too low, the data received from the information elements 390 may not be used because the data may be corrupt.

In the depicted embodiment, the power validation circuit 378 includes a comparator 389 that compares the feedback power VFB with a reference voltage. If the feedback power VFB is equal to or higher than the reference voltage, the comparator 389 might output a high voltage. This high voltage can be selectively overridden by a MOSFET switch 387 in response to communications received from the information elements 390. If the feedback power VFB is lower than the reference voltage, the comparator 389 might output a low voltage. The low voltage can override the MOSFET switch 387 such that communications from the information elements 390 are not sent to the monitor.

In the depicted embodiment, sensor connection status is provided to the monitor via the sensor detect circuit 372. The sensor detect circuit 372 includes a sensor detect line 375 in communication with a pull-up resistor 373. When a sensor 385 is not connected to the line 375, the line 375 may be pulled high. This high voltage may be inverted by a MOSFET switch 374 to provide a low signal to the monitor via sensor connect line 381. The switch 374 may be omitted in some embodiments.

In response to a sensor 385 being connected to the sensor detect line 375, a shorted line 386 (or low resistance line) in the sensor 385 can cause the line 375 to be pulled low. This low value can be inverted by the switch 374 to provide a high signal to the monitor. This signal can indicate that the sensor 385 is connected. Conversely, if the sensor 385 is disconnected, the line 375 may again be pulled high, resulting in a low output of the switch 374. As a result, the monitor may receive a rapid or near-immediate indication that the sensor 385 has been disconnected.

The sensor detect circuit 372 also includes passive elements in the depicted embodiment, such as a capacitor 391, to smooth or debounce contact oscillations from the sensor 385. Thus, the sensor detect circuit 372 can also be considered a debounce circuit. In other embodiments, the sensor detect circuit 372 can be replaced with other forms of debounce circuitry.

Advantageously, in certain embodiments, the sensor detect circuit 372 can be used instead of polling the one or more information elements 390 frequently to determine if the sensor 385 is connected. Alternatively, the polling cycle of the one or more information elements 390 may be reduced. Reducing or eliminating the polling cycle can reduce power consumption by the circuit 300C.

The sensor detect circuit 372 may be used to detect the connection of cables, such as a splitter cable, as well as or instead of detecting sensor connections. In some embodiments, a sensor detect line 375 may be provided for each sensor in a multi-sensor system, each cable, or the like. Moreover, the sensor detect circuit 372 may also be used with cables that do not have a decoupling circuit.

Figure 4:
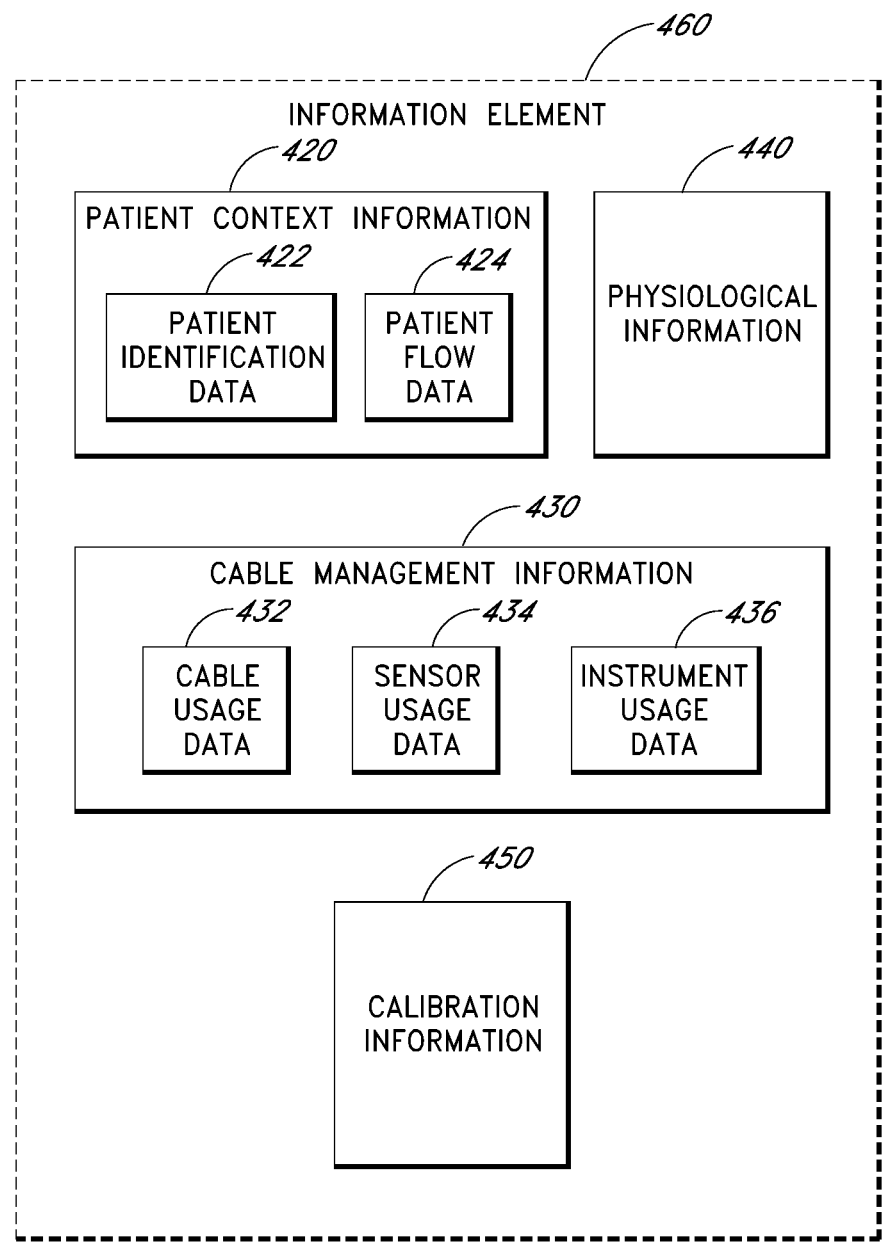
FIG. 4 illustrates a block diagram showing calibration information and other exemplary forms of data that can be stored in an information element.

FIG. 4 illustrates a block diagram of example forms of data that can be stored on an information element 460. In the depicted embodiment, patient context information 420, cable management information 430, physiological information 440 and calibration information 450 are shown. The patient context information can include patient identification data 422 and patient flow data 424. Cable management information 430 can include cable usage data 432, sensor usage data 434, and instrument usage data 436. However, while the data is depicted in FIG. 4 as comprising discrete categories, data from one category may be included within another. Data from one or more categories also may not be included, or alternatively, additional data categories than that shown may be included.

The calibration information 450 may be related to the characteristics of the components attached to the system. For example, each information element may store information related to behavioral characteristics of the corresponding component (e.g., a sensor or cable) to which it is attached.

Such information can include electrical properties such as capacitances, impedances, resistances, and the like. The information element 460 may further store mechanical properties such as a mechanical sensitivity of a sensing element. For example, in an embodiment, an acoustic sensor assembly includes a piezoelectric membrane that vibrates in response to mechanical vibrations generated by the physiological sounds of a patient. The membrane generates a corresponding voltage signal. The mechanical sensitivity of such a device, or the mechanical properties of other mechanical components can be stored in the information element 460.

Additionally, frequency response characteristics such as cut-in and cut-off values can be stored. These cut-in and cut-off values can be mechanical values, such as for a piezoelectric membrane of an acoustic sensor, or electrical cut-in and cut-off values, such as for one or more circuit components. In addition to having their ordinary meaning, mechanical cut-in and cut-off frequencies may correspond to the lowest and highest frequency values, respectively, at which a particular component passes a signal from its input to its output. Saturation values and/or gain characteristics of certain components (e.g., circuit components) may also be included.

In addition to these specific examples and categories of calibration information, a wide variety of other calibration data may be used. Generally, any data related to characteristics of components in the sensor path may be stored.

In one embodiment patient identification data 422 can include a patient's name, a patient's unique hospital identification number, type of patient or body tissue, information about the patient's age, sex, medications, and medical history, and other information that can be useful for the accuracy of alarm settings and sensitivities and the like. In addition, the patient identification data 422 may also include an $SpO_2$ fingerprint, determined by a pulse oximeter. In one such embodiment, the $SpO_2$ fingerprint is determined by calculating a ratio of an infrared detected wavelength and a red detected wavelength. The $SpO_2$ fingerprint can be used to detect if a sensor or cable is being improperly reused.

Patient flow data 424 can include a record of departments the patient has visited, length of stay (LOS) in those departments, overall LOS in the hospital, admittance date and time, discharge date and time, time stamps for events occurring in the hospital, and the like. Some or all of this information, in conjunction with the patient identification data, can constitute a patient flow profile.

Cable usage data 432 may include buyer or manufacturer information, cable type, serial number of the cable, date of purchase, time in use, and cable life monitoring functions (CLM), including near expiration percentage, update period, expiration limit, and an index of functions. In addition, the cable usage data 432 may include numerous read write parameters, such as the number of times the cable is connected to a monitoring system, the number of times the cable has been successfully calibrated, the total elapsed time connected to a monitor system, the number of times the cable has been connected to one or more sensors, the total time used to process patient vital parameters, the cumulative current, voltage, or power applied to the cable, the cumulative temperature of the cable, and the expiration status of the cable.

In an embodiment, the number of times the cable is placed on or removed from a patient is monitored and an indication is stored in the memory. The number of times a sensor connected to the cable is placed on or removed from a patient can be monitored by monitoring the number of probe off conditions sensed, or it can be monitored by placing a separate monitoring device on the cable or sensor to determine when a sensor clip is depressed, opened, removed, replaced, attached, or the like.

In an embodiment, the average operating temperature of the cable is monitored and an indication stored. This can be done, for example, through the use of bulk mass or through directly monitoring the temperature of the cable or the temperature of the cable's connectors. In an embodiment, the number of different monitors connected to the cable is tracked and an indication is stored in memory. In an embodiment, the number of times the cable is calibrated is monitored, and an indication is stored in memory. In an embodiment, the number of patients that use a cable is monitored and an indication is stored. This can be done by, for example, by storing sensed or manually entered information about the patient and comparing the information to new information obtained when the cable is powered up, disconnected and/or reconnected, or at other significant events or periodically to determine if the cable is connected to the same patient or a new patient. In an embodiment, a user is requested to enter information about the patient that is then stored in memory and used to determine the useful cable life. In an embodiment, a user is requested to enter information about cleaning and sterilization of the cable, and an indication is stored in the memory.

Although described with respect to measuring certain parameters in certain ways, various other electrical or mechanical measurements can be used to determine any useful parameter in measuring the useful life of a cable.

Sensor usage data 434 can include some or all of the same information as the cable usage data but applied to sensors attached to the cable, and may also include information on the type or operation of the sensor, type or identification of a sensor buyer, sensor manufacturer information, sensor characteristics including the number of wavelengths capable of being emitted, emitter specifications, emitter drive requirements, demodulation data, calculation mode data, calibration data, software such as scripts, executable code, or the like, sensor electronic elements, sensor life data indicating whether some or all sensor components have expired and should be replaced, encryption information, monitor or algorithm upgrade instructions or data, or the like. In an embodiment, the sensor usage data 434 can also include emitter wavelength correction data.

Sensor usage data 434 can also include the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters it is intended to measure (e.g., HbCO, HbMet, etc.) calibration data, software such as scripts, executable code, or the like, sensor electronic elements, whether it is a disposable, reusable, or multi-site partially reusable, partially disposable sensor, whether it is an adhesive or non-adhesive sensor, whether it is reflectance or transmittance sensor, whether it is a finger, hand, foot, forehead, or ear sensor, whether it is a stereo sensor or a two-headed sensor, sensor life data indicating whether some or all sensor components have expired and should be replaced, encryption information, keys, indexes to keys or has functions, or the like monitor or algorithm upgrade instructions or data, and some or all of parameter equations.

Instrument usage data 436 can include buyer or manufacturer information, information on the type of monitors that the cable has connected to, number of monitors the cable has connected to, duration of cable connections to the monitors, duration of use of the monitor, trend history, alarm history, sensor life, an identification number for a specific monitor, and the like. In addition, the instrument usage data 436 may include all or a portion of all the cable and sensor usage data described above.

The physiological information 440 may include any of the physiological parameters described above, obtained from the sensors or monitors attached to the information element 460. In one implementation, the information element 460 enables the physiological information 440 to be transferred between physiological monitors. As a result, a historical view of the patient's physiological parameters may be provided to different monitors throughout the hospital. Thus, clinicians in different departments can observe the patient's physiological information obtained in a previous department, enabling clinicians to provide a higher quality of care.

Figure 5:
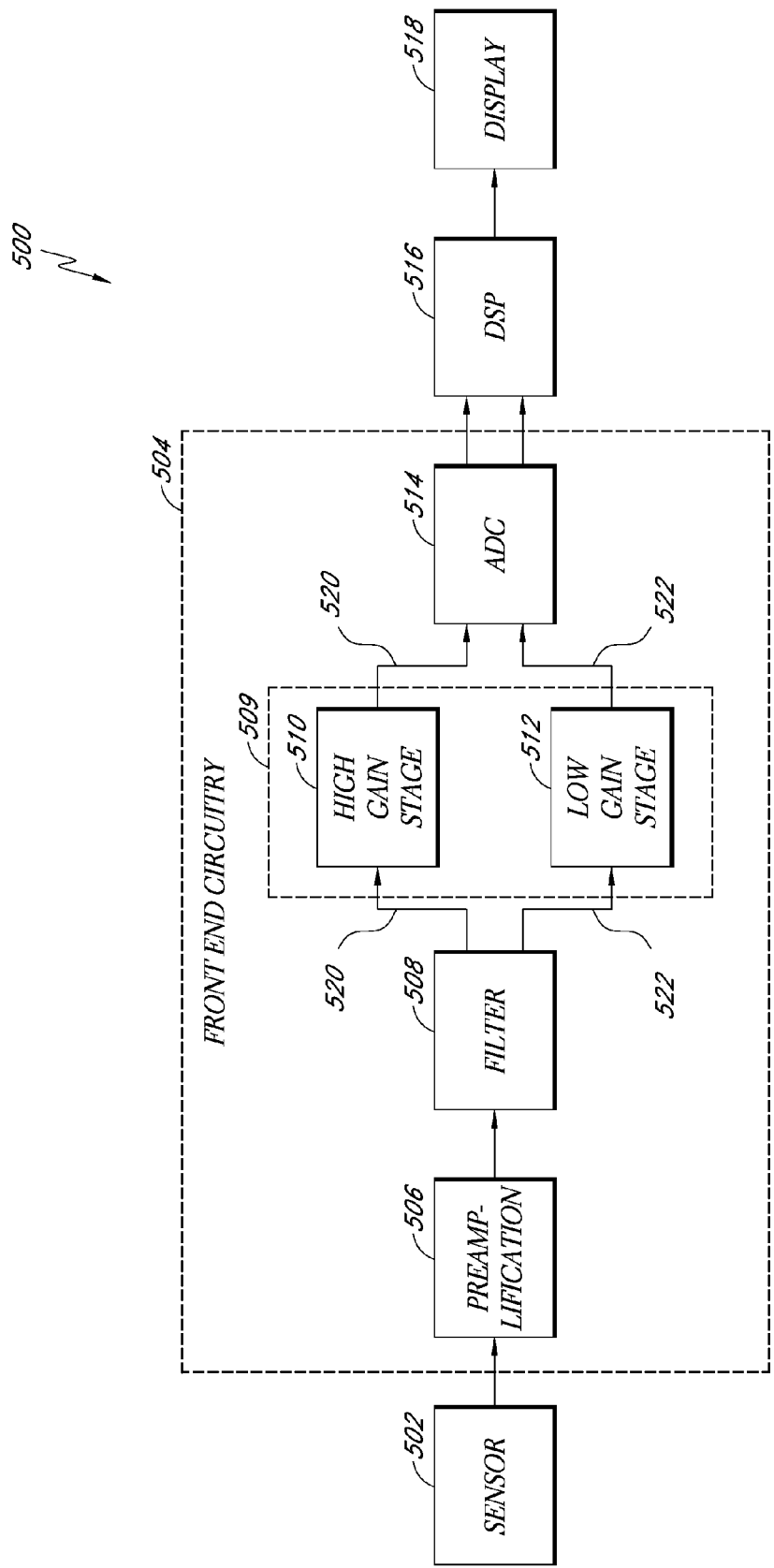
FIG. 5 illustrates a functional block diagram of an embodiment of a physiological monitoring system configurable to perform multi-stage calibration according to certain embodiments.

FIG. 5 illustrates a functional block diagram of an acoustic signal processing system 500. The block diagram illustrates components which may be included on portions of various stages of a monitoring system having a multi-stage sensor path, for example. The processing system 500 includes an acoustic sensor 502 which can detect a physiological signal and produces a corresponding voltage signal. In one embodiment, the sensor 502 is an acoustic sensor such as one of the acoustic sensors described herein and is configured to measure at least one of a patient's respiratory rate, heart sounds, and related parameters.

The system 500 further includes front end circuitry 504 configured to condition the analog electrical signal output by the sensor 502 for processing. The front end circuitry 504 includes a pre-amplification circuit 506, one or more filters 508, a high gain stage 510, a low gain stage 512, and an analog to digital converter (ADC) 514. The system 500 further includes a digital signal processor (DSP) and a display 518.

The preamplification circuit 506 receives and amplifies the voltage signal from the sensor, such as by a predetermined gain. The one or more filters 508 modify the preamplified signal by, for example, smoothing or flattening the signal. In one embodiment, the one or more filters 508 include a high pass filter which passes high frequency signals and attenuates low frequency signals. The one or more filters 508 may include other types of filters, such as low pass or bandpass filters may be used instead of, or in addition to a high pass filter in some embodiments.

The output from the filter 508 is divided into two channels, for example, first and second channels 520, 522. In some embodiments, more than two channels may be used. For example, 3, 4, 8, 16, 32 or more channels may be used. The voltage signal is transmitted on both first and second channels 520, 522 to gain bank 509. The gain bank 509 in certain embodiments includes one or more gain stages. In the depicted embodiment, there are two gain stages 510, 512. A high gain stage 510 amplifies the voltage signal into a higher voltage signal. A low gain stage 512 in certain embodiments does not amplify or attenuates the voltage signal. In alternative embodiments, the low gain stage 512 may amplify the voltage signal with a lower gain than the gain in the high gain stage 510.

The amplified signal at both first and second channels 520, 522 then passes to an analog-to-digital converter (ADC) 514. The ADC 514 has two input channels to receive the separate output of both the high gain stage 510 and the low gain stage 512. The ADC bank 514 samples and converts analog voltage signals into digital signals. The digital signals then pass to the DSP 516 for processing. A display 518 then outputs a graphical display of one or more physiological parameters such as a respiratory rate, heart sounds, etc., based on the processed signal. In certain embodiments, a separate sampling module samples the analog voltage signal and sends the sampled signal to the ADC 514 for conversion to digital form. Additionally, in certain embodiments two ADCs 514 may be used in place of one ADC 514.

A variety of configurations are possible for the processing system 500. For example, one or more of the illustrated components may not be included in certain embodiments. In other embodiments, additional components may be used instead of or in addition to the illustrated components. Example compatible processing systems 500 are described in the '883 Application and are incorporated by reference herein.

Example Multi-Stage Calibration System Implementation

As discussed, the various components of the acoustic processing system 500 may be dispersed throughout various stages of a monitoring system having a multi-stage sensor path. An example implementation of a multi-stage monitoring system capable of performing an example multi-stage calibration process will now be described with reference to FIGS. 2, 3 and 5. The example system includes a sensor path arrangement compatible with those depicted in FIGS. 2 and 3 implementing an acoustic processing system such as the processing system 500 of FIG. 5. This example implementation is provided for the purposes of illustration, and is not limiting.

Referring again to FIG. 2, the sensor assembly 201 including the sensor 215 and integrated sensor cable 217 form a first stage in the example implementation. The instrument cable 211 forms a second stage and includes preamplification circuitry, such as the preamplification circuitry 506 of FIG. 5. By placing the preamplification circuit in a component other than the sensor, such as the instrument cable 211, cost can be reduced. For example, in one embodiment, a disposable sensor is used, or the sensor 215 otherwise requires more frequent replacement than the reusable instrument cable 211. For example, the sensor 215 may become soiled or generally wear out more quickly than the instrument cable 211, due to repeated contact with the patient, relatively more fragile componentry, etc. Thus, it is advantageous to reduce the cost and complexity of constructing the sensor 215 by moving the preamplification circuit to the instrument cable 211.

Additionally, in order to amplify the sensed signal for processing before significant attenuation or other signal degradation occurs, it can be desirable to place the preamplification circuit generally as close to the sensor as possible. Thus, in one embodiment, the preamplification circuitry is located on the connector 209 of the instrument cable 211, which is adjacent to the sensor assembly 201 in an attached configuration. Thus, the preamplification circuitry in this embodiment is both relatively close to the sensor in the signal path and is on a separate component, achieving both performance benefit and cost savings. In other embodiments, the preamplification circuit resides on the sensor 215 or at some other location.

The hub 220 forms a third stage, and a front end module in the monitor (not shown) forms a fourth stage and includes the components of the front end circuitry other than the preamplification circuit. For example, the front end module includes one or more filters, high and low gain stages, and an ADC such as those of the system 500 of FIG. 5. In other embodiments, all of the front end circuitry is located in the monitor, some other stage, or is dispersed through the stages in some other manner. The monitor also houses a DSP and a display such as the DSP 516 and display 518 of FIG. 5.

Additionally, each of the four stages include at least one associated information element. While the information elements may be located in a variety of locations, in the example embodiment the information elements associated with stages one through four are located on the connector 205 of the integrated sensor cable 217, the connector 209 of the instrument cable, within the housing of the hub 220, and in the monitor, respectively.

In the example implementation, the information element associated with the example first (sensor) stage is a 1 Kbit EEPROM, although other types of information elements can be used. The information element stores data relating to the mechanical sensitivity of the piezoelectric sensing element, one or more mechanical cut-in and cut-off frequencies, and one or more capacitances associated with the sensor 215. In one embodiment, the mechanical sensitivity may be determined by comparing the amplitude of an acoustic input signal to the amplitude of the resulting voltage signal. In addition to having its ordinary meaning, mechanical cut-in and cut-off frequencies may correspond to the lowest and highest frequency values, respectively, of physiological sounds that the sensor 215 is capable of detecting to produce a corresponding voltage signal. The capacitance values may correspond to one or more of the output capacitance of the sensor 215, the capacitance of the integrated sensor cable 217, a combination thereof, or some other capacitance.

In one embodiment, the information element associated with the example second (instrument cable/preamplifier) stage is a 1 Kbit EEPROM and includes information relating to characteristics of the preamplifier 506 such as one or more of a differential gain value, input impedance, cut-in and/or cut-off frequencies, a minimum saturation value, and the like. In one embodiment, the cut-in frequency is not stored in the EEPROM but is instead computed (e.g., by the monitor) using the capacitance of the first stage and the input impedance of the second stage. Thus, by taking advantage of the information already stored in the previous stage, less memory space is used. As a result, smaller memory components or less memory components may be used, providing potential cost savings. In other embodiments, the cut-in frequency is stored on the information element.

The example third stage formed by the hub 220 includes a 20 Kbit EEPROM which stores information related to the hub 220. As discussed, the hub 220 can include electrical decoupling circuitry. In the example embodiment, the hub 220 includes decoupling circuitry having an optocoupler and/or transformer such as the decoupling circuitry described herein with respect to the example hub 1720 of FIG. 17.

The decoupling circuitry may exhibit some amount of phase change and/or non-linear behavior such as signal compression, for example. Information is stored in the information element which can be used to account for this behavior. For example, one or more coefficients are stored in the EEPROM which can be used to construct the curve of the non-linear response. Additional information related to the hub 220 is stored in the information element and can include, for example, a gain, cut-in and cut-off frequencies, output resistance, and minimum saturation level of the hub stage.

As discussed, the fourth stage in the example embodiment is located on the monitor and includes the front end circuitry other than preamplifier, which is stored in the instrument cable 211. The information element associated with the fourth stage can be a flash memory, for example, and is configured to store calibration data related to the properties of the front end circuitry components. For example, such information can include gain and frequency cut-off values for the high gain channel, gain and cut-off frequency values for the low gain channel, etc.

The fourth stage may also have a characteristic input gain value. In the example embodiment, this value is not stored by the information element but is instead computed (e.g., by the monitor) using the output resistance from the previous stage. Again, by taking advantage of stored information, less memory is used, providing cost savings. Alternatively, the input stage gain value may be stored on the information element.

A processor in the monitor downloads the calibration information from the information elements of the four stages and performs the multi-stage calibration based on the information. For example, the processor may acquire or generate a mathematical representation of the responses (e.g., transfer functions) associated with one or more of the stages or portions thereof. The processor may then perform an appropriate computation to generally remove or modify the effect of the four stages or portions thereof on the sensor signal. For example, the processor may perform the mathematical inverse (e.g., inverse transfer functions) of those responses. In general, any appropriate mathematical operation incorporating the calibration information may be used.

While a variety of types of calibration information have been described with respect to the above example embodiment, a wide variety of other kinds of information (e.g., quality control information, compatibility information, cable management information, patient context information, and/or physiological information, etc.) may be stored in other configurations. Additionally, other or additional types of components including different information elements, front end circuitry components, sensors, cables, etc., are contemplated. Moreover, while the example implementation involves a system incorporating an acoustic sensor, systems having other types of sensors (e.g., optical sensors such as pulse oximeter sensors) may also incorporate the multi-stage calibration described herein.

In the example implementation, physically separable components generally form separate stages. In other embodiments, stages may be delineated in some other manner, such as based on functionality rather than physical separability. Additionally, in some embodiments, one or more physically separable components do not include calibration information and the monitor does not factor in characteristics associated with that component in the adaptive processing.

In certain embodiments the monitoring system is a "restricted access" system, which generally only functions with quality-controlled components that are authorized or compatible, such as components or families of components from a specific manufacturer or licensed vendor. This restricted access functionality can ensure proper functioning and quality of the monitoring system, for example, providing safety benefits.

In such systems, each of the information elements may include authentication information indicating that the corresponding component is compatible with the system. The authentication information may include predetermined data such as a key or other information capable of identifying the respective component as a compatible with the system.

The monitoring device can be configured to read the authentication information and verify that each of the attached components is authorized or otherwise compatible with the system. If the components are compatible, the monitoring device enables physiological monitoring. On the other hand, if one or more of the components do not have the appropriate authentication information, the monitoring device disables the monitoring function. Such authentication information may be stored in combination with the calibration information discussed above.

In some embodiments, only select components in the system require authentication by the monitor. For example, in one embodiment, the sensor is the only device including authentication information.

Examples of restricted access technology compatible with embodiments described herein are provided in U.S. Pat. No. 7,843,729, titled "Pulse Oximeter Access Apparatus and Method," the disclosure of which is hereby incorporated by reference in its entirety.

Figure 6:
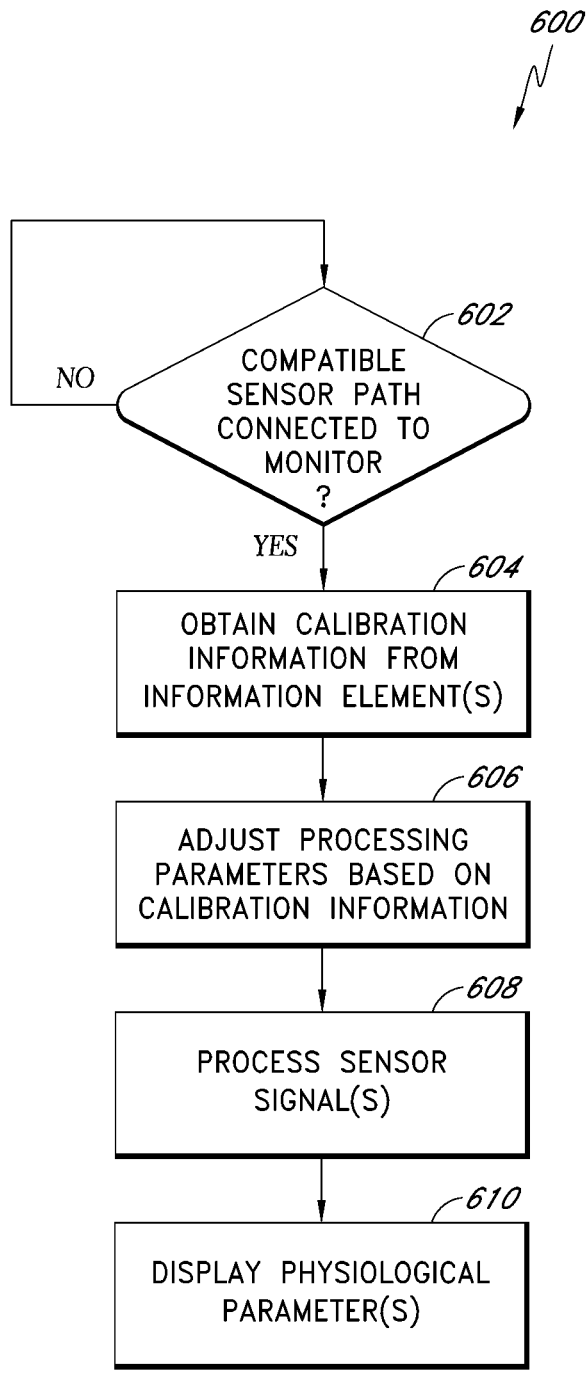
FIG. 6 illustrates a flowchart diagram of an example physiological monitoring process implementing multi-stage calibration according to certain embodiments.

FIG. 6 illustrates a flowchart diagram of an example physiological monitoring process 600 incorporating multi-stage calibration. In one embodiment, the process 600 begins at step 602, where the process 600 determines whether a compatible multi-stage sensor path is appropriately connected to the monitor. The process 600 may enter step 602 when it receives an indication that a user would like to begin physiological monitoring, for example. In another embodiment, the process 600 may enter step 602 when it detects that one or more components have been connected to the monitor.

At step 602, for example, the process 600 may electrically ping or otherwise communicate with the components in the sensor path (e.g., sensors, cables, etc.) to determine whether a compatible sensor path configuration is connected to the monitor. In one embodiment, the process 600 downloads and verifies quality control and/or authentication information from each of the stages in the sensor path at step 602 to determine if the sensor path configuration is compatible. Generally, any of the types of information described herein can be advantageously used in the compatibility determination (e.g., quality control information, cable management information, patient context information, and/or physiological information). If one or more of the sensor path stages are not compatible or are not appropriately connected, the process 600 waits.

If the components of the multi-stage sensor path are appropriately connected, the process 600 of some embodiments obtains calibration information from information elements associated with one or more of the stages at step 604. For example, the process may download calibration information from one or more of a sensor, instrument cable, splitter cable, front-end circuitry, and/or some other component. In one embodiment, the process 600 downloads the information from the attached components serially, such as in the order in which they are connected. In other embodiments, the process 600 may receive the information in parallel from one or more of the stages, or in another suitable manner.

The process 600 continues to step 606, where the process 600 adjusts one or more signal processing parameters of the physiological monitor based on the calibration information. For example, the process 600 determines the characteristic response associated with one or more of the stages or portions thereof using the calibration information. In some embodiments, the process 600 then adjusts one or more parameters of a signal processing algorithm using the determined responses or other calibration information.

At step 608, the process 600 processes the detected signal according to the adjusted processing parameters. For example, the process 600 may perform multi-stage calibration by applying the inverse of one or more of the calculated sensor path stage responses as described herein, or by performing some other compatible operation. In general, any of the automatic calibration techniques described herein may be used, such as those described with respect to FIG. 2, 3B, or 5, for example. In other configurations, some other appropriate algorithm or technique is used.

In addition to the automatic calibration operation, the process 600 at step 608 may apply appropriate further processing to the signals to extract the physiological signal or signals. At step 610, the process 600 provides a graphical display of one or more physiological parameters based on the processed signal or signals. Until monitoring is discontinued, the process 600 of certain embodiments generally continues to process the signal and display the physiological parameter by repeating steps 608 and 610.

Further Compatible Embodiments

Multiple sensors are often applied to a medical patient to provide physiological information about the patient to a physiological monitor. Some sensors, including certain optical and acoustic sensors, interface with the monitor using a cable having power, signal, and ground lines or wires. One or more these lines can pose an electric shock hazard when multiple sensors are attached to the patient. If an electrical potential exists in the ground line, for instance, a ground loop can form in the patient or in the ground line, allowing unwanted current to pass through the patient through the ground line. Power fluctuations or surges, such as from a defibrillator, can potentially harm the patient and damage the monitor or the sensors.

This disclosure describes decoupling circuitry that can be used to prevent or substantially prevent ground loops and other current loops from forming. Using decoupling circuitry in this manner can be referred to as providing sensor isolation, patient isolation, patient protection, sensor decoupling, or the like. Currently-available physiological monitors that connect to one sensor at a time using a single cable may not have this decoupling circuitry. Upgrading these monitors to receive two or more sensors can create the shock hazard described above unless protective circuitry is added to these monitors. For existing single-sensor monitors, adding this circuitry might require a costly upgrade of the monitors' internal components. For new single-sensor monitors, the decoupling circuitry could be added during manufacturing. But this approach would be cost-inefficient for buyers who wish to use only one sensor with the device.

Accordingly, in certain embodiments, the decoupling circuitry is provided in a medical cable assembly. The medical cable assembly includes, in some embodiments, a splitter cable that interfaces multiple physiological sensors with a single sensor port on a physiological monitor. Advantageously, in certain embodiments, the medical cable assembly allows multiple sensors to connect to a monitor while reducing the risk of electric shock to a patient.

FIGS. 7A and 7B illustrate embodiments of physiological monitoring systems 700A, 700B interfacing with multiple sensor assemblies 750. The physiological monitoring systems 700A, 700B each include a physiological monitor 710, a splitter cable 720, two cables 730, and two sensor assemblies 750. The physiological monitoring systems 700A, 700B may include all of the features of the physiological monitoring system 100 described above.

In the physiological monitoring system 700A of FIG. 7A, a patient decoupling circuit 740a is provided in one of the cables 730b. In the physiological monitoring system 700B of FIG. 7B, the patient decoupling circuit 740b is provided in the splitter cable 720b. These patient decoupling circuits 740a, 740b can reduce or prevent ground loops from forming in the patient and/or in the physiological monitoring system 700. Although not shown, a decoupling circuit could instead be provided in one or both of the sensor assemblies 750.

The physiological monitor 710 processes and outputs physiological information received from sensors included in the sensor assemblies 750a, 750b. The physiological monitor 710 of certain embodiments includes a power decoupling circuit 715, a processing board 717, and a connector 719. The power decoupling circuit 715 may be a transformer or the like that decouples power (e.g., AC electrical power) received from a power source (such as an electrical outlet) and the circuitry of the physiological monitor 710. The power decoupling circuit 715 prevents or substantially prevents current spikes from damaging the other components of the physiological monitor 710 or the patient. In embodiments where the physiological monitor 710 receives power from another source, such as batteries, the power decoupling circuit 715 may not be included.

The processor 717 of certain embodiments is a microprocessor, digital signal processor, a combination of the same, or the like. The processor 717 receives power from the power decoupling circuit 715. In some implementations, the processor 717 processes physiological signals received from the sensors 750 and outputs the processed signals to a display, storage device, or the like. In addition, the processor 717 may communicate with an information element (e.g., a memory device) included in a cable or sensor. Information elements are discussed in greater detail herein with respect to FIGS. 3 through 6 and 11 through 17.

The connector 719 includes a physical interface for connecting a cable assembly to the physiological monitor 710. In the embodiment shown in FIGS. 7A and 7B, a single connector 719 is provided. Additional connectors 719 may also be included in some implementations. One embodiment of a physiological monitor having additional connectors 719 is described below with respect to FIG. 8.

The splitter cable 720 is provided in some embodiments to enable the physiological monitor 710 having one connector 719 to interface with multiple sensors 750. The splitter cable 720 interfaces with the connector 719 through a monitor connector 721 in the splitter cable 720. In the depicted embodiment, where the splitter cable 720 interfaces with two sensors 750, cable sections 722 of the splitter cable 720, which branches into two sections generally forming a "Y" shape or the like. Thus, the splitter cable 720 can be a Y cable or the like. While the splitter cable 720 is shown forming a "Y" shape, other configurations and shapes of the splitter cable 720 may be used. For example, the splitter cable 720 could branch into more than two cable sections 722 to interface with more than two sensors 750.

The cable sections 722 are shown connected to the monitor connector 721 and two cable connectors 723. In some embodiments, the cable sections 722 branch into more than two parts and connect to more than two cable connectors 723. In addition, in some embodiments the splitter cable 720 couples directly to two or more sensors 750.

Some embodiments of the splitter cable 720 include one or more lines, conductors, or wires per cable connector 723. One line might be provided, for example, to interface with one or more electrocardiograph (ECG) sensors. Two or three lines might be provided per cable connector 723, for example, to interface with an optical or acoustic sensor. For instance, three lines might be provided, including a power line, a signal line, and a ground line (see FIGS. 4 and 5). The power line powers the sensor 750, the signal line receives signals from the sensor 750, and the ground line acts as an electrical return path for the power and/or signal lines. In some embodiments, one or more of the lines coming from one sensor 750a are placed at a predetermined distance from one or more of the lines coming from another sensor 750b to reduce cross-talk interference between the sensors 750. One or more electromagnetic shielding and/or insulating layers may also be provided to help reduce cross-talk. Lines from different sensors may merge into a shared line that connects electrically to the monitor 710, and some form of multiplexing might be used to allow the different sensors to communicate along the shared lines.

The cables 730a, 730b interface with the splitter cable 720 in the depicted embodiment through cable connectors 731. In certain embodiments, each cable 730 also includes a cable section 732 and a sensor connector 733 that connects to a sensor 750. The cable section 732 in some implementations includes one or more lines or wires for communicating with the sensor 750. For example, a power line, sensor line, and ground line may be provided that correspond to the power line, sensor line, and ground line in the example splitter cable 720 described above.

In an embodiment, one of the cables 730 includes the decoupling circuit 740a. In FIG. 7A, for example, the decoupling circuit 740a is shown in the cable section 732 of the cable 730b. The decoupling circuit 740a may also be placed in the cable connector 731 or the sensor connector 733, or in a combination of one or more of the connectors 731, 733 and/or the cable section 732. In another exemplary embodiment, FIG. 7B shows that the decoupling circuit 740b can be included in one of the cable sections 722 of the splitter cable 720b. The decoupling circuit 740b may also be placed in the monitor connector 721 or the sensor connector 723, or in a combination of the cable sections 722 and/or one or more of the connectors 721, 723.

Multiple decoupling circuits 740 may also be provided in one or more of the cables 730 and/or in the splitter cable 720 in other embodiments. In particular, in one embodiment when N cables 730 are provided (or one splitter cable 720 with N connectors 723), N−1 decoupling circuits 740 are provided in N−1 of the cables 730 or in the various sections of the splitter cable 720.

The decoupling circuit 740 of certain embodiments electrically decouples a sensor 750 from the physiological monitor 710. In addition, the decoupling circuit 740 can electrically decouple one sensor (e.g., the sensor 750*b*) from another sensor (e.g., the sensor 750*a*) in certain embodiments. The decoupling circuit 740 can be a transformer, an optocoupler, a DC-DC converter, a switched-mode converter, or the like or a combination of the foregoing. In addition, the decoupling circuit 740 can include one or more optical fibers. An optical fiber may be used in place of the signal line, for example. More detailed embodiments of the decoupling circuit 740 are described below with respect to FIGS. 9 and 10.

The sensors 750 connect to the sensor connectors 733 of the cables 730. In an embodiment, one of the sensors 750 is an optical sensor, such as a multiple wavelength oximetry sensor. The other sensor 750 in one embodiment is an acoustic sensor. In addition, the sensor 750 may be an acoustic sensor that also monitors ECG signals, such as is described in U.S. Provisional Application No. 60/893,853, titled "Multi-parameter Physiological Monitor," and filed Mar. 8, 2007, the disclosure of which is hereby incorporated by reference in its entirety and U.S. application Ser. No. 12/044,883, titled "SYSTEMS AND METHODS FOR DETERMINING A PHYSIOLOGICAL CONDITION USING AN ACOUSTIC MONITOR," and filed Mar. 7, 2008. Many other types of sensors 250 can also be used to monitor one or more physiological parameters.

Figure 8:
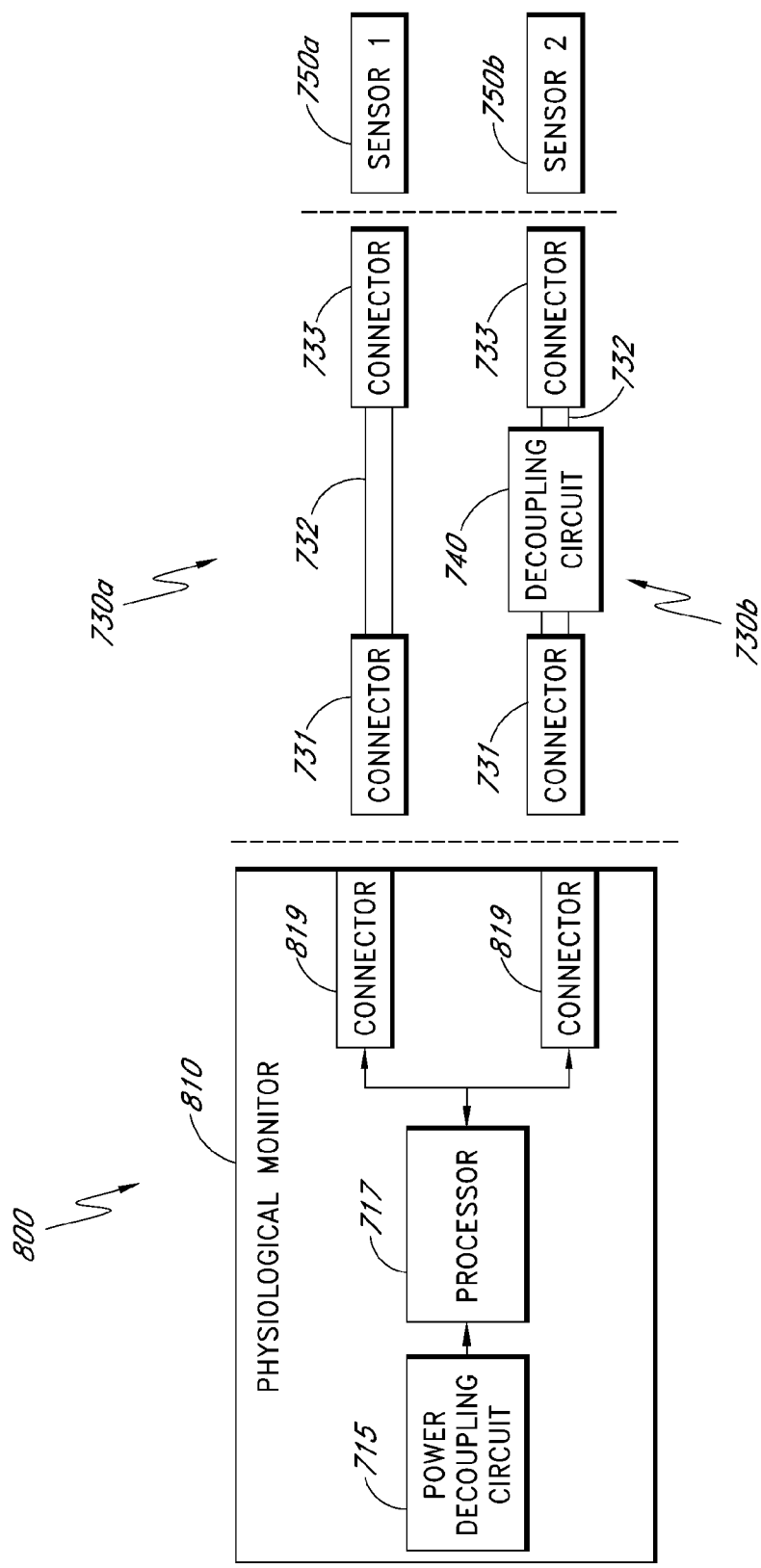
FIG. 8 illustrates a block diagram of another embodiment of a physiological monitoring system having multiple cables.

FIG. 8 illustrates another embodiment of a physiological monitoring system 800 having multiple cables 730. The physiological monitoring system 800 may have certain of the features of the physiological monitoring systems 100, 700 described above. For example, like the physiological monitoring system 700 described above, the physiological monitoring system 800 includes a physiological monitor 810, two cables 730, and two sensors 750. In the physiological monitoring system 800, a decoupling circuit 740 is provided in one of the cables 730*b*.

Like the physiological monitor 710, the physiological monitor 810 includes a power decoupling circuit 715 and a processor 717. Unlike the physiological monitor 710, however, the physiological monitor 810 includes two connectors 819 for interfacing directly with two cables without using a splitter cable. To save costs for users who will use only one sensor 750 with the physiological monitor 810, a decoupling circuit 740 is not provided in the physiological monitor 810. Instead, the decoupling circuit 740 can be provided in a separate cable 730*b* that can be used with the physiological monitor 810.

For example, a user might use one cable 730*a* and sensor 750*a* at a time with the physiological monitor 810. Since only one sensor 750*a* is being used, ground or other current loops are less likely to form in the patient. If the user later wishes to use additional sensors 750, the user can obtain a cable 730*b* having the decoupling circuit 740. Using the cable 730*b* can beneficially allow the user to continue using the physiological monitor 810 without performing an upgrade to the physiological monitor's 810 internal components.

Figure 9:
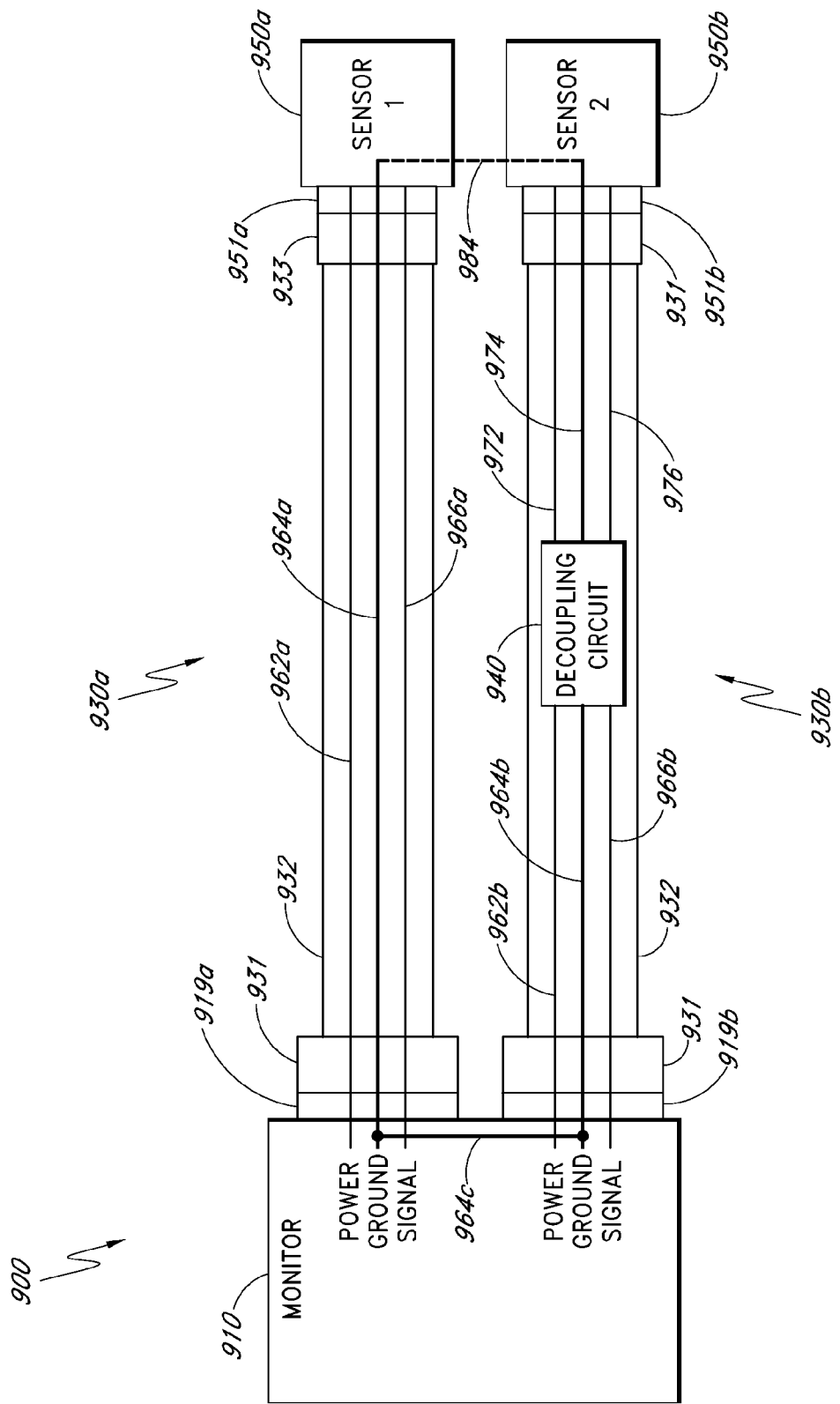
FIG. 9 illustrates a block diagram of yet another embodiment of a physiological monitoring system having multiple cables.

FIG. 9 illustrates another embodiment of a physiological monitoring system 900 having multiple cables 930. The physiological monitoring system 900 may have certain of the features of the physiological monitoring systems 100, 700, 300 described above. For example, like the physiological monitoring systems described above, the physiological monitoring system 900 includes a physiological monitor 910, two cables 930, and two sensors 950. The features described with respect to FIG. 9 may also be applied to a monitoring system having a splitter cable instead of multiple cables.

In the depicted embodiment, the cables 930 are shown connected to the physiological monitor 910 and to the sensors 950. Connectors 919 in the physiological monitor 910 couple with connectors 931 of the cables 930, and connectors 933 of the cables couple with connectors 951 of the sensors 950. A cable section 932 extends between the connectors 931, 933 of each cable.

The cable 930*a* includes a power line 962*a*, a ground line 964*a*, and a signal line 966*a* extending from the connector 931 to the connector 933. These lines form electrical connections with corresponding power, ground, and signal lines in the connector 919*a* of the physiological monitor 910 and in the connector 951*a* of the sensor 950*a*. Likewise, the cable 930*b* includes a power line 962*b*, a ground line 964*b*, and a signal line 966*b*. These lines form electrical connections with corresponding power, ground, and signal lines in the connector 919*b* of the physiological monitor 910. In addition, these lines extend from the connector 931 to a decoupling circuit 940. A power line 972, ground line 974, and signal line 976 extend from the decoupling circuit 940 to the connector 931 to form electrical connections with corresponding power, signal, and ground lines in the connector 951*b* of the sensor 950*b*. The cable section 932 can also include one or more electrical insulation and shielding layers, materials, or fillers. Although not shown, one or more of the cables 930*a*, 930*b* may also include one or more communications lines for communicating with information elements.

In the depicted embodiment, the ground line 964*a* is connected to the ground line 964*b* in the physiological monitor 910 through line 964*c*. When both sensors 950 are placed on a patient, the ground lines 964*a* and 979*b* may also be in electrical communication through the patient, as illustrated by the dashed line 984. If the decoupling circuit 940 were not present in one of the cables 930, a ground loop might be formed along the lines 964*a*, 964*b*, 964*c*, 974, and 984 (illustrated with bold lines) due to, for example, a difference in electrical potential in the lines 964*a*, 964*b*, 964*c*, and 974. While not shown in bold, current loops might also form in some cases among the power lines 962*a*, 962*b*, 972 or the signal lines 966*a*, 966*b*, 976.

Advantageously, in certain embodiments, the decoupling circuit 940 reduces the risk of a ground or other loop forming by decoupling one or more of the power lines 962*b*, 972, the signal lines 964*b*, 974, or the ground lines 964*b*, 974. More detailed embodiments illustrating how the decoupling circuit 940 could decouple one or more lines is described below with respect to FIGS. 10A through 10C and FIG. 3C.

While only one decoupling circuit is shown, in other embodiments, multiple decoupling circuits may be provided in one cable 930. For instance, a first decoupling circuit could be connected to the power line 962*b* and the ground line 966*b*, and a second decoupling circuit could be connected to the signal line 964*b* and to the ground line 966*b*. In addition, in certain embodiments, there may be a decoupling circuit in each cable 930*a*, 930*b*.

Figure 10A:
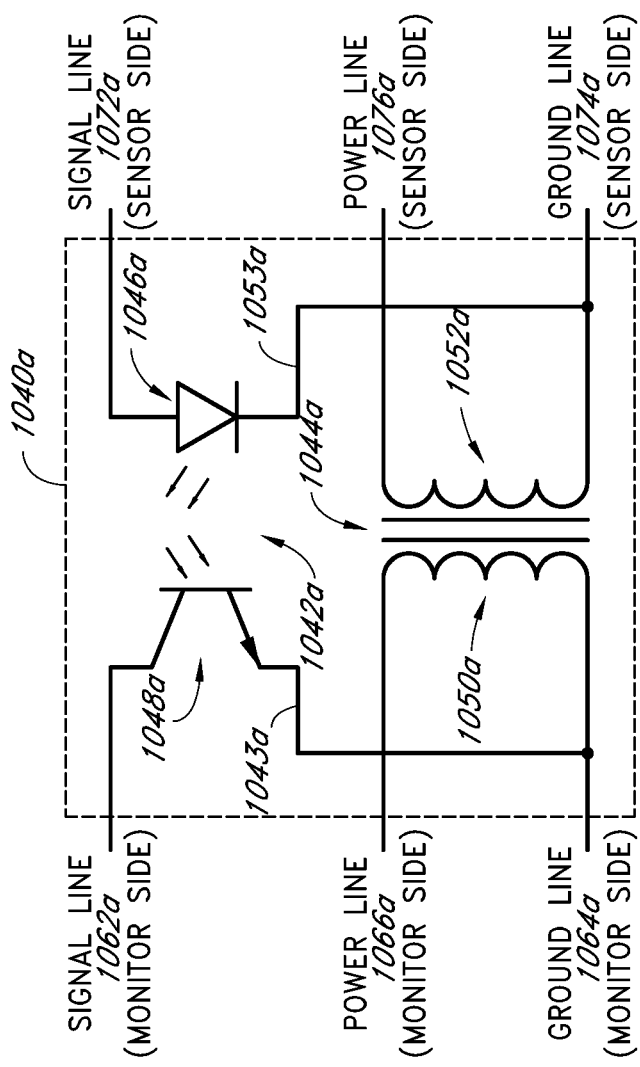
FIGS. 10A through 10C illustrate embodiments of decoupling circuits.

FIG. 10A illustrates a more detailed embodiment of a decoupling circuit 1040*a* suitable for use with any of the embodiments discussed herein. The decoupling circuit 1040*a* may include all the features of the decoupling circuits 740, 840, and 940 described above. For example, the decoupling circuit 1040*a* may be included in a medical cable assembly, such as a splitter cable, medical cable, or the like, or in a sensor assembly. The decoupling circuit 1040*a* can decouple electrical signals and prevent or reduce ground or other conducting loops from forming and can protect against current surges in a multi-sensor physiological monitoring system.

The decoupling circuit 1040*a* is shown within dashed lines. The decoupling circuit 1040*a* of various embodiments receives a signal line 1062*a*, a power line 1066*a*, and a ground line 1064*a*. These lines can be connected to a physiological monitor (not shown). In addition, the decoupling circuit 1040*a* receives a signal line 1072*a*, a power line 1076*a*, and a ground line 1074*a*, which may be connected to a sensor (not shown).

In an embodiment, the power line 1066*a* provides power from a physiological monitor to the decoupling circuit 1040*a*, which provides the power to the sensor through the power line 1076*a*. The signal line 1072*a* provides a physiological signal from the sensor to the decoupling circuit 1040*a*, which provides the physiological signal to the monitor through the signal line 1062*a*. The ground lines 1064*a* and 1074*a* act as return paths for their respective signal and power lines 1062*a*, 1066*a*, 1072*a*, 1076*a*.

The decoupling circuit 1040*a*, in some implementations, includes an optocoupler 1042*a* and a transformer 1044*a*. The optocoupler 1042*a* receives physiological signals from the sensor line 1072*a* and provides the signals to the sensor line 1062*a* optically using, for example, a photodiode 1046*a* and a phototransistor 1048*a*. Because the signals are transmitted optically, in certain embodiments there is no electrical contact between the signal lines 1062*a*, 1072*a*. Similarly, the transformer 1044*a* provides power from the power line 1066*a* to the power line 1076*a* without electrical contact between the lines 1066*a*, 1076*a*. Through mutual inductance, electromagnetic energy is transferred from one winding 1050*a* of the transformer 1044*a* to another winding 1052*a*. Because the signals are transmitted using mutual inductance, there is no electrical contact between the power lines 1066*a*, 1076*a*.

In certain embodiments, because the power lines 1066*a*, 1076*a* and signal lines 1062*a*, 1072*a* are electrically decoupled, the ground lines 1064*a*, 1074*a* can also be electrically decoupled. As shown, a ground line 1043*a* of the optocoupler 1042*a* on the monitor side connects to the ground line 1064*a*, and a ground line 1053*a* of the optocoupler 1042*a* on the sensor side connects to the ground line 1074*a*. As a result, the risk of ground loops forming in the patient may be reduced or eliminated.

Many other configurations of the decoupling circuit 1040*a* may be employed. For instance, a second optocoupler 1042*a* may be used in place of the transformer 1044*a*, or a second transformer 1044*a* may be used in place of the optocoupler 1042*a*. In addition, some forms of DC-DC converters or switched mode converters may be used in place of either the optocoupler 1042*a* or the transformer 1044*a*. Alternatively, one or more optical fibers may be used.

Moreover, one or more optical fibers can be used instead of the optocoupler 1042*a* or the transformer 1044*a*. Because the optical fibers transmit optical, rather than electrical signals, using optical fibers in certain embodiments beneficially reduces the likelihood of ground loops forming in the patient. In one example embodiment, the optocoupler 1042*a* in FIG. 10A is replaced with an optical fiber, but the transformer 1044*a* is still included in the decoupling circuit 1040*a*. The optical fiber allows signals to be transmitted through the signal line while preventing current from passing through the signal line. In addition, if optical fibers are used for the signal lines of multiple sensors, the optical fibers can also reduce cross-talk interference among the signal lines.

Figure 10B:
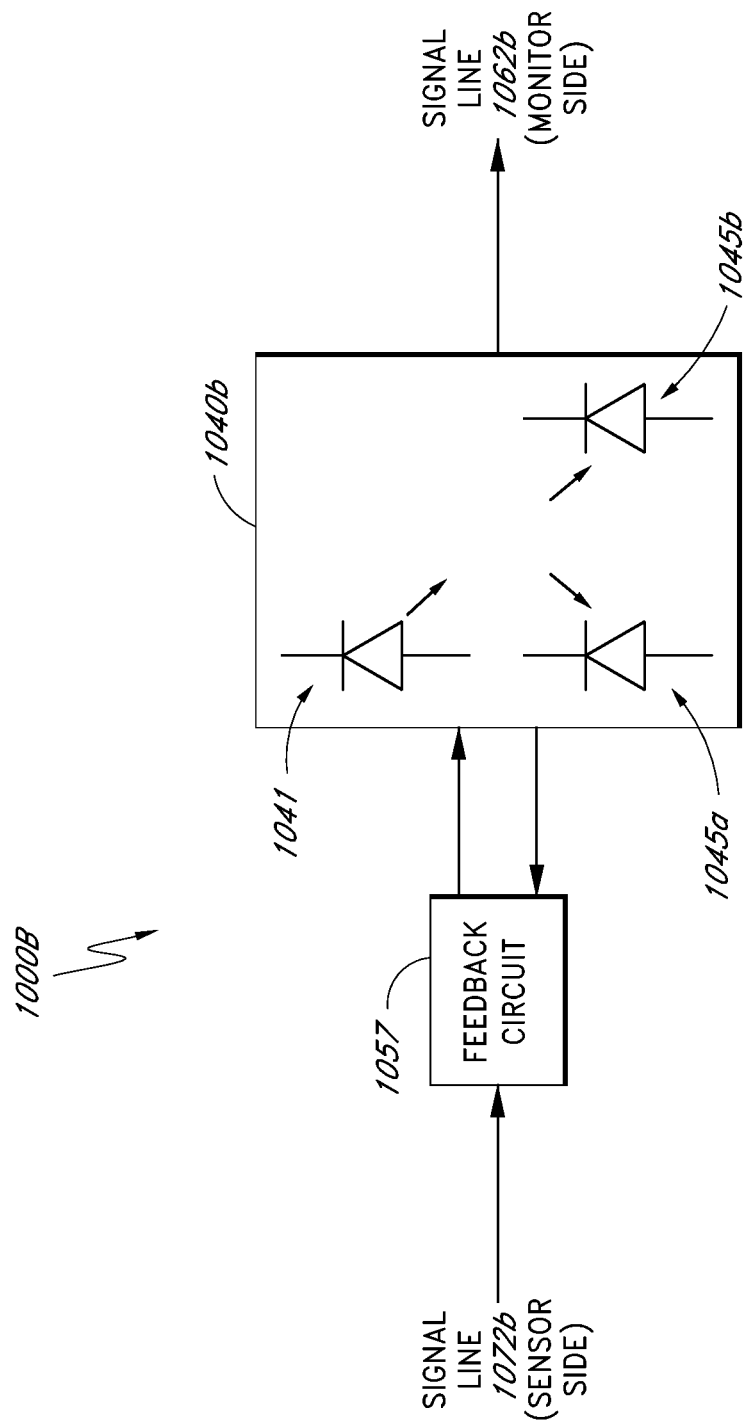

FIG. 10B illustrates an embodiment of a circuit 1000B that includes a decoupling circuit 1040*b*. The decoupling circuit 1040*b* may include all the features of the decoupling circuits 240, 340, and 440 described above. For example, the decoupling circuit 1040*b* may be included in a medical cable assembly, such as a splitter cable, medical cable, or the like, or in a sensor assembly.

The decoupling circuit 1040*b* is shown decoupling a signal line 1062*b* connected to a monitor from a signal line 1072*b* connected to a sensor. In the depicted embodiment, the decoupling circuit 1040*b* is an analog optocoupler. The decoupling circuit 1040*b* includes a transmitting photodiode 1041 and two receiving photodiodes 1045*a*, 1045*b* for feedback control.

The transmitting photodiode 1041 receives physiological signals from the signal line 1072*b* via a feedback circuit 1057 (described below). The transmitting photodiode 1041 transmits the physiological signals to both of the receiving photodiodes 1045*a*, 1045*b*. The receiving photodiode 1045*b* transmits the signals it receives from the transmitting photodiode 1041 to the monitor via signal line 1062*b*. The receiving photodiode 1045*a* transmits the signals it receives to a feedback circuit 1057.

Many diodes are inherently unstable due to nonlinearity and drift characteristics of the diodes. As a result of such instability, the signal produced by the transmitting photodiode 1041 may not correspond to the signal provided by the signal line 1072*b* from the sensor. The receiving diode 1045*a* can therefore be used as a feedback diode to provide a received signal to the feedback circuit 1057.

The feedback circuit 1057 can include an amplifier or the like that adjusts its output provided to the transmitting photodiode 1041 based at least partly on a difference between the signal of the transmitting photodiode 1041 and the receiving diode 1045*a*. Thus, the feedback circuit 1057 can correct for errors in the transmitted signal via feedback from the feedback or receiving diode 1045*a*.

Figure 10C:
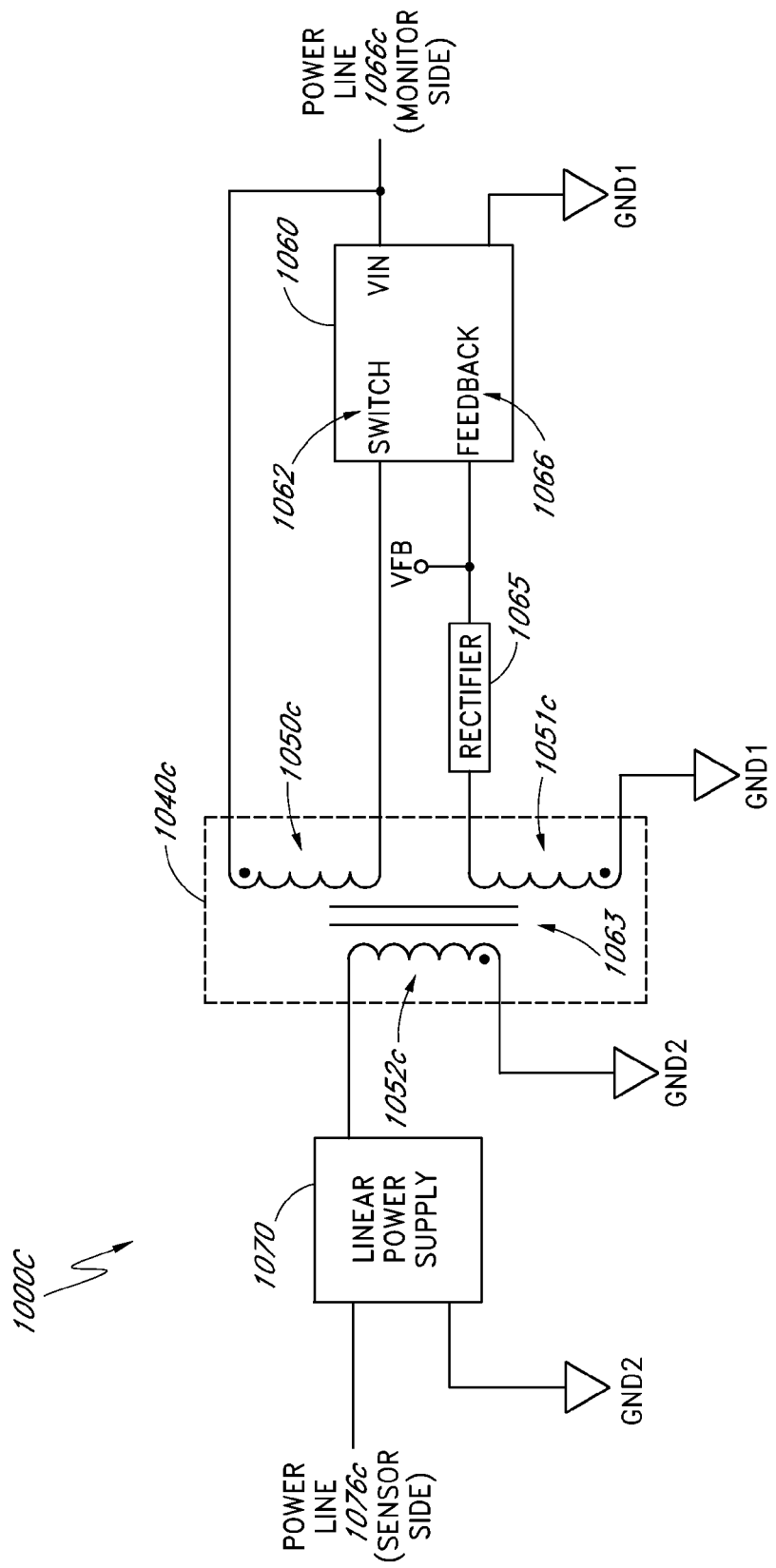

FIG. 10C illustrates another embodiment of a circuit 1000C that includes a decoupling circuit 1040*c*. The decoupling circuit 1040*c* may include all the features of the decoupling circuits 740, 840, and 940 described above. For example, the decoupling circuit 1040*c* may be included in a medical cable assembly, such as a splitter cable, medical cable, or the like, or in a sensor assembly.

The decoupling circuit 1040*c* is shown decoupling a power line 1066*c* connected to a monitor from a power line 1076*c* connected to a sensor. The decoupling circuit 1040*c* can be used together with the decoupling circuit 1040*b* of FIG. 10B in some embodiments. For example, the decoupling circuits 1040*b*, 1040*c* may be provided on the same circuit board. Like the decoupling circuit 1040*b*, the decoupling circuit 1040*c* uses feedback to dynamically correct or control the output of the decoupling circuit 1040*c*.

The decoupling circuit 1040*c* in the depicted embodiment is a flyback transformer having two primary windings 1050*c*, 1051*c* and one secondary winding 1052*c*. The primary winding 1050*c* receives power (VIN) from the power line 1066*c*. A switched mode power supply 1060 also receives power (VIN) from the power line 1066*c*. In an embodiment, the switched mode power supply 1060 is a DC-DC converter or the like. A switch pin 1062 of the power supply 1060 can be enabled or otherwise actuated to allow power (VIN) to cycle through the primary winding 1050*c*. The switch pin 1062 may cause the power to be switched according to a predetermined duty cycle. Feedback may be used, as described below, to maintain a stable or relatively stable duty cycle.

As the primary winding 1050c is being energized, the primary winding 1050c may store energy in itself and in a core 1063 of the transformer. Through inductive coupling, this energy may be released into the secondary winding 1052c and into the primary winding 1051c. The polarity of the windings 1052c, 1051c (as indicated by the dots on the windings) may be the same to facilitate the transfer of energy. Likewise, the polarity of the windings 1052c, 1051c may differ from the polarity of the winding 1050c.

Like the feedback receiving photodiode 1045a described above, the primary winding 1051c acts as a flyback winding in certain embodiments to transmit the received power as a feedback signal. A rectifier 1065 rectifies the power received from the primary winding 1051c and provides a feedback power VFB to a feedback pin 1066 of the power supply 1060. The power supply 1060 may then use the difference between the received feedback power VFB and the transmitted power VIN to adjust VIN to compensate for any error in the transmitted power. For example, the power supply 1060 can adjust the duty cycle described above based at least partly on the error, e.g., by increasing the duty cycle if the VFB is low and vice versa. This flyback operation can advantageously maintain a stable or substantially stable power duty cycle despite varying load conditions on the decoupling circuit 1040c.

The secondary winding 1050c can provide an output to a linear power supply 1070, which may rectify the received power, among other functions. The linear power supply 1070 may provide the power to the power line 1076c for transmission to the sensor.

FIGS. 11A and 11B illustrate an example splitter cable 1120. FIG. 11A depicts a side view of the splitter cable 1120 while FIG. 11B depicts a bottom view of the splitter cable 1120. The splitter cable 1120 includes a housing 1107 that includes a circuit board 1140 having a decoupling circuit, show in phantom. The housing 1107 further includes wires 1142, also shown in phantom, in communication with the circuit board 1140 and with first cable sections 1130a, 1130b and a second cable section 1122 of the splitter cable 1120. The housing 1107 is also shown connected to the second cable section 1122, which in turn connects to a connector 1121. In an embodiment, the connector 1121 is used to connect the splitter cable 1120 to a physiological monitor.

The housing 1107 of the splitter cable 1120 further connects to one of the first cable sections 1130a through a connector 1131. Another one of the first cable sections 1130b is integrally coupled to the housing 1107 of the splitter cable 1120 in the depicted embodiment. In one implementation, the splitter cable 1120 and the cable 1130b are used to obtain physiological information from a single sensor, and the cable 1130a may be added to the splitter cable 1120 to obtain physiological information from an additional sensor. It should be noted that in an alternative embodiment, the first cable section 1130b is not integrally attached to the housing 1107 but instead attaches to the housing using a second connector. Or, both of the first cable sections 1130 could be integral to the housing 1107.

The circuit board 1140 interfaces with both first cable sections 1130a, 1130b and with the second cable section 1122. The circuit board 1140 may include, for example, one or more integrated circuits or discrete circuit components that together are implemented as a decoupling circuit. In addition, the circuit board 1140 can include one or more information elements for storing various forms of data.

Figure 12:
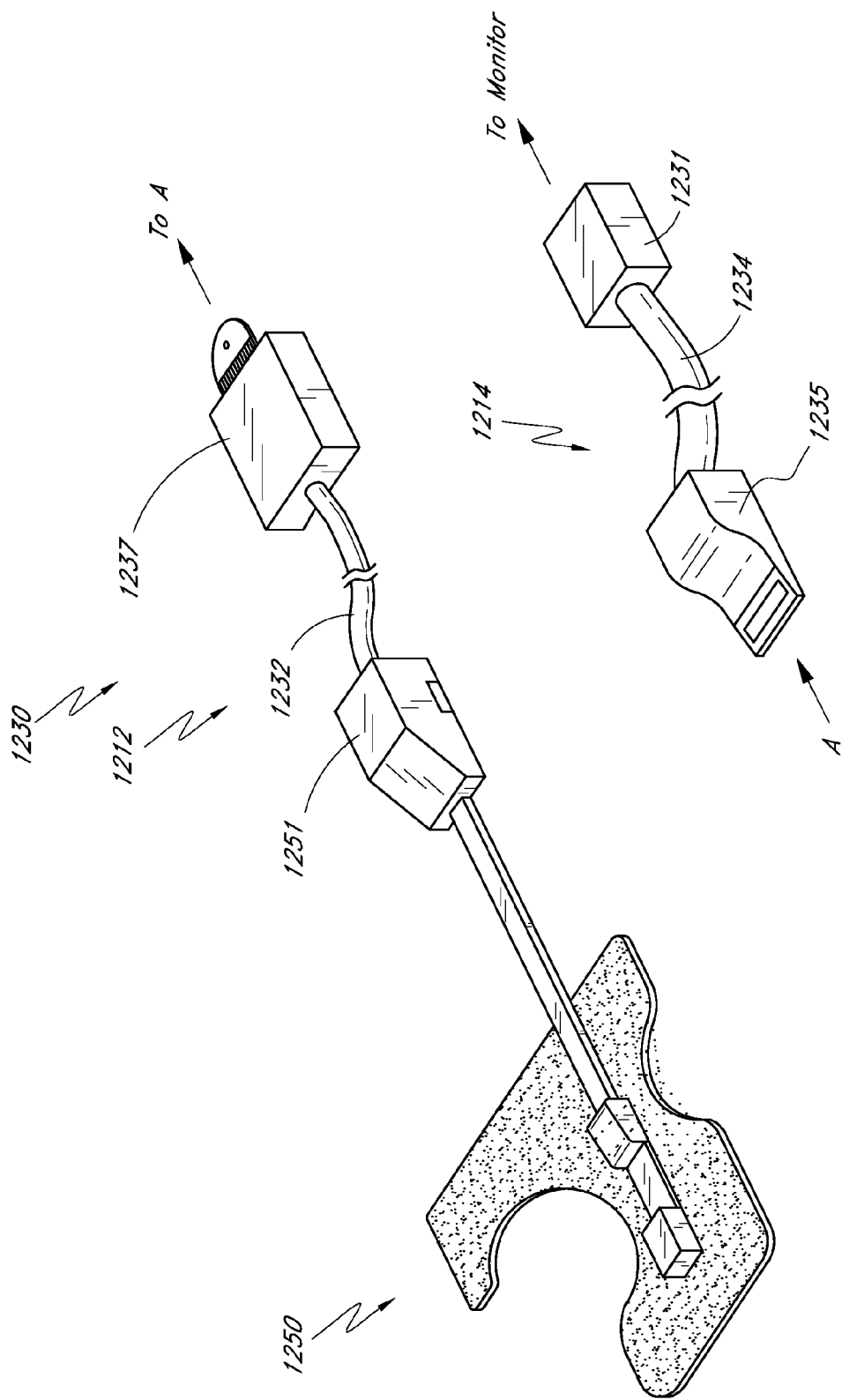
FIG. 12 illustrates a perspective view of an example sensor and cable assembly.

Turning to FIG. 12, additional embodiments of cable assemblies 1230 will be described. As explained above with respect to FIG. 1, cable assemblies having two separate cables may be provided in some embodiments. These separate cables can include a sensor cable 1212 and an instrument cable 1214. In one embodiment, the sensor cable 1212 is a short, lightweight cable, adapted to facilitate comfortable attachment of sensors to a medical patient. In certain embodiments, the instrument cable 1214 is a heavier, sturdier cable, acting as a durable interface between the sensor cable 1212 and a monitor. Sensor cables 1212 and instrument cables 1214 may be periodically replaced. Periodic replacement is advantageous in certain embodiments for a wide variety of reasons. For example, the cable can become soiled or damaged, causing cable failure, inaccurate results, or patient cross-contamination.

In addition, one or more decoupling circuits or information elements (see FIGS. 3 and 15) may be incorporated into the cable assembly 1230 in certain embodiments. The information elements may store cable management information related to usage of the cable assembly and devices connected to the cable assembly. The information elements may also store patient context information related to patient identification and patient movement (flow) among hospital departments, thereby tracking the patient's progress throughout the hospital. Examples of patient context information are described more fully in U.S. patent application Ser. No. 11/633,656, titled "Physiological Alarm Notification System," filed Dec. 4, 2006, which is hereby incorporated by reference in its entirety. Moreover, the information elements can store physiological information in some implementations. The information elements may further store calibration information related to the particular components presently attached to the system. For example, each information element may store information related to behavioral characteristics of the stage to which it is attached (e.g., a sensor, cable, etc.). The monitoring device may use such information to automatically calibrate a multi-stage sensor path, for example. Example calibration information is described herein, with respect to FIGS. 2 through 6, for example.

Referring again to FIG. 12, a sensor cable 1212 is shown connected to a sensor assembly 1250. The sensor cable 1212 may include a flexible cable section 1232 having an elongated shape, a connector 1251 for interfacing with a sensor assembly 1250, and a connector 1237 for interfacing with an instrument cable 1214. The flexible nature of the cable section 1232 in one embodiment is provided to enable greater patient comfort, as the patient can move more easily with a flexible sensor cable 1212 attached.

The depicted example instrument cable 1214 includes a stiff or relatively rigid, durable cable section 1234 having an elongated shape, a connector 1235 for interfacing with the sensor cable 1212, and a connector 1231 for interfacing with a physiological monitor. As the instrument cable 1214 of various embodiments is not connected directly to the patient, the instrument cable section 1234 may be less flexible (and more durable) than the sensor cable section 1232, thereby extending the life of the instrument cable 1214.

Decoupling circuitry and/or information elements may be included within the sensor cable 1212, the instrument cable 1214, or both. The decoupling circuits and/or information elements may be placed in any of the connectors 1237, 1251, 1235, or 1231 or in either cable section 1232, 1234. In other embodiments, one or more information elements may be included in any of the splitter cables described above. In alternative embodiments, the sensor cable 1212 can be a splitter cable.

FIG. 13 illustrates an embodiment of a physiological monitoring system 1300 which may be used in a hospital, nursing home, or other location where medical services are administered (collectively "hospital"). Certain aspects of the physiological monitoring system 1300 are described in more detail in U.S. patent application Ser. No. 11/633,656, titled "Physiological Alarm Notification System," filed Dec. 4, 2006, which is hereby incorporated by reference in its entirety.

The physiological monitoring system 1300 of certain embodiments includes patient monitoring devices 1302. The patient monitoring devices 1302 of various embodiments include sensors 1350, one or more physiological monitors 1310, cables 1330 attaching the sensors 1350 to the monitors 1310, and a network interface module 1306 connected to one or more physiological monitors 1310. Each patient monitoring device 1302 in some embodiments is part of a network 1320 of patient monitoring devices 1302. As such, the patient monitoring devices 1302 in these embodiments can communicate physiological information and alarms over a hospital wireless network (WLAN) 1326 or the Internet 1350 to clinicians carrying end user devices 1328, 1352.

The network interface module 1302 of certain embodiments transmits physiological information on demand or in the event of an alarm to the end-user devices 1328, 1352 and/or transmits the alarm to a central nurses' station. Alternatively, the network interface module 1302 transmits information and alarms to a server 1336. The server 1336 is a computing device, such as an appliance server housed in a data closet or a workstation located at a central nurses' station. The server 1336 passes the information or alarms to the end user devices 1328, 1352 or to the central nurse's station. The alarms may be triggered when certain physiological parameters exceed safe thresholds, thereby enabling clinicians to respond rapidly to possible life-threatening situations. Situations giving rise to an alarm might include, for example, decreased heart rate, respiratory rate, low SpO$_2$ levels, or any other physiological parameter in an abnormal range.

The network interface module 1302 in one embodiment also performs cable management by generating an alarm when one of the cables 1330 is nearing the end of its life. The network interface module 1302 determines whether the cable's 1330 life is close to expiring by, for example, analyzing some or all of the data described above with respect to FIG. 4. In one embodiment, if the network interface module 1302 determines that the cable life is close to expiration, the network interface module 1302 provides an expiration message as an alarm.

In one embodiment, the server 1336 receives this expiration message. The server 1336 then checks an inventory stored in a database 1338 to see if a replacement cable is available. If there is no replacement cable in the inventory, the server may forward the message to a supplier 1370 over the Internet 1350 (or through a WAN, leased line or the like). In an embodiment, the server 1336 transmits an email message to a supplier 1370 that indicates the cable location, cable condition, and/or other cable usage data. The supplier 1370 in one embodiment is a cable seller. Upon receiving the message, the supplier 1370 may automatically ship a new cable to the hospital. Consequently, cable 1330 inventories are able to be maintained with minimal or no user intervention in this implementation, and cables 1330 may be replaced preemptively, before cable failure.

In additional embodiments, the network interface module 1306 may monitor sensor utilization, such as the number of sensors used during the patient's stay, the types of sensors, and the length of time in use before replacement. Such data can be used by the hospital to preemptively plan restocking and set department par inventory levels. In addition, a supplier can use this data to restock the hospital or implement a just in time inventory control program. Moreover, such information can be used by the supplier to improve overall cable reliability and for the hospital to better plan and manage consumables.

The network interface module 1306 of various implementations also performs context management. In one embodiment, context management includes associating context information with physiological information to form a contextual data package. As described above, context information may include patient identification data and patient flow data. In addition, context information may include context information related to usage of the network interface module 1306 and context information related to the network. For example, this additional context information may include an identification number of the network interface module 1306, time stamps for events occurring in the physiological monitoring system 1300, environmental conditions such as changes to the state of the network and usage statistics of the network interface module 1306, and identification information corresponding to the network (e.g., whether the network connection is WiFi or Ethernet).

The network interface module 1306 receives context information in one embodiment by a nurse entering the information in the network interface module 1306 or from the server 1336. The network interface module 1306 transmits or communicates the contextual data package to clinicians during an alarm, upon clinician request, or on a scheduled basis. In addition, the network interface module 1306 may transmit a continuous stream of context information to clinicians.

The server 1336 receives contextual data packages from a plurality of network interface modules 1306 and stores the contextual data package in a storage device 1338. In certain embodiments, this storage device 1338 therefore archives long-term patient data. This patient data may be maintained even after the patient is discharged. Thus, context information may be stored for later analysis to, for example, develop patient care metrics and improve hospital operations. The patient data could be deleted after the care metrics are developed to protect patient privacy.

Although the functions of cable management and context management have been described as being performed by the network interface module 1306, in certain embodiments, some or all of these functions are instead performed by the physiological monitor 1310. In addition, the physiological monitor 1310 and the network interface module 1306 may both perform cable management and/or context management functions.

Figure 14:
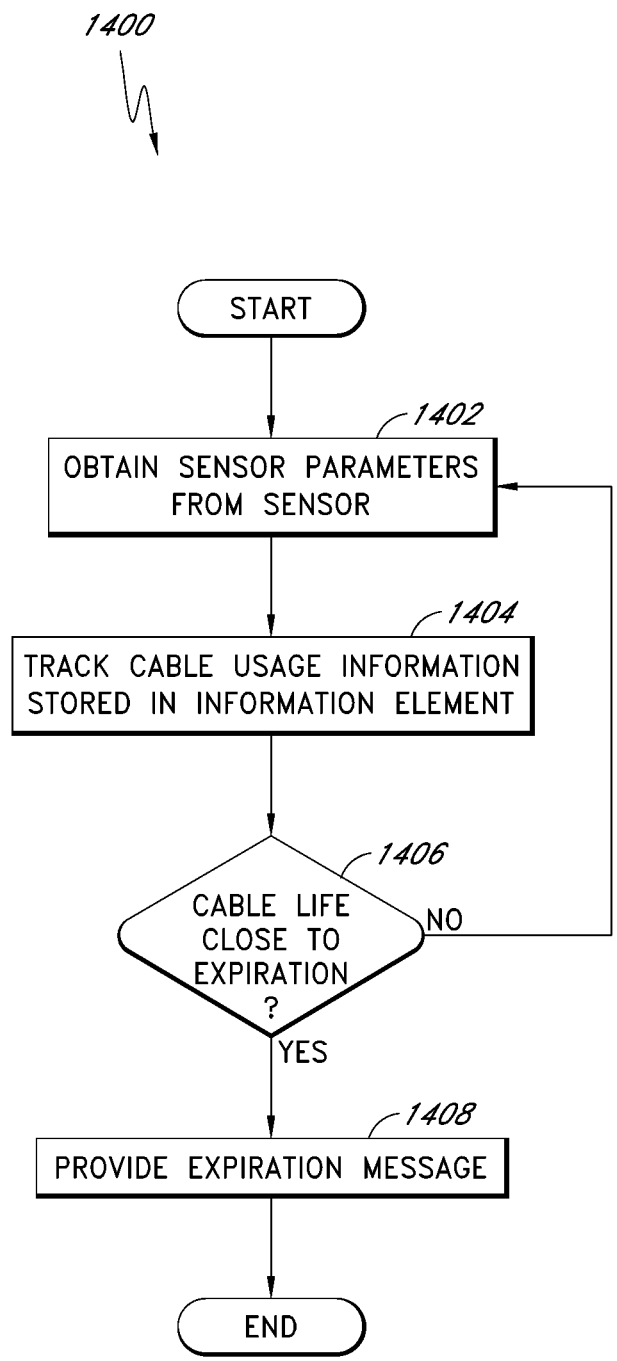
FIGS. 14 and 15 illustrate flowchart diagrams of example cable management processes.

FIG. 14 illustrates an embodiment of a usage tracking method 1400 for tracking the life of a medical cable. In one implementation, the usage tracking method 1400 is performed by the network interface module and/or one of the physiological monitors described above. More generally, the usage tracking method 1400 may be implemented by a machine having one or more processors. Advantageously, in certain embodiments, the usage tracking method 1400 facilitates replacing a cable prior to failure of that cable.

The usage tracking method 1400 begins by obtaining sensor parameters from a sensor at block 1402. At block 1404, cable usage information stored in an information element is tracked. The cable usage information can be tracked by at the same time or substantially the same time as obtaining sensor parameters from the sensor. Alternatively, the cable usage information may be tracked by determining cable usage at the start or end of monitoring (e.g., obtaining sensor parameters), or periodically throughout monitoring. In addition, the cable usage information may be tracked even if the block 1402 were not performed, e.g., when the monitor is not currently obtaining parameters from the sensor.

At decision block 1406, it is determined whether the cable's life is close to expiring (or whether the cable has in fact expired). This determination may be made using the data described above with respect to FIG. 4. In addition, the this determination may be made using sensor life functions applied analogously to the life of the cable.

If it is determined that the cable life is close to expiration (or has expired), an expiration message is provided at block 1408. In one embodiment, this message is provided as an alarm on the monitor or at a central nurses' station. The message may also be provided to a clinician's end user device, which may be located in the hospital or at a remote location. Moreover, the message may be provided to a server, which forwards the message to a supplier, which ships a new cable. In an embodiment, the message is an email that indicates the cable location, cable condition, and/or other cable usage data. If, however, it is determined that the cable life is not close to expiration (or is not expired), the usage tracking method 1400 loops back to block 1402 to continue monitoring. In effect, the usage tracking method 1400 may continue monitoring and/or tracking cable usage information until the cable is close to expiration or has expired.

Figure 15:
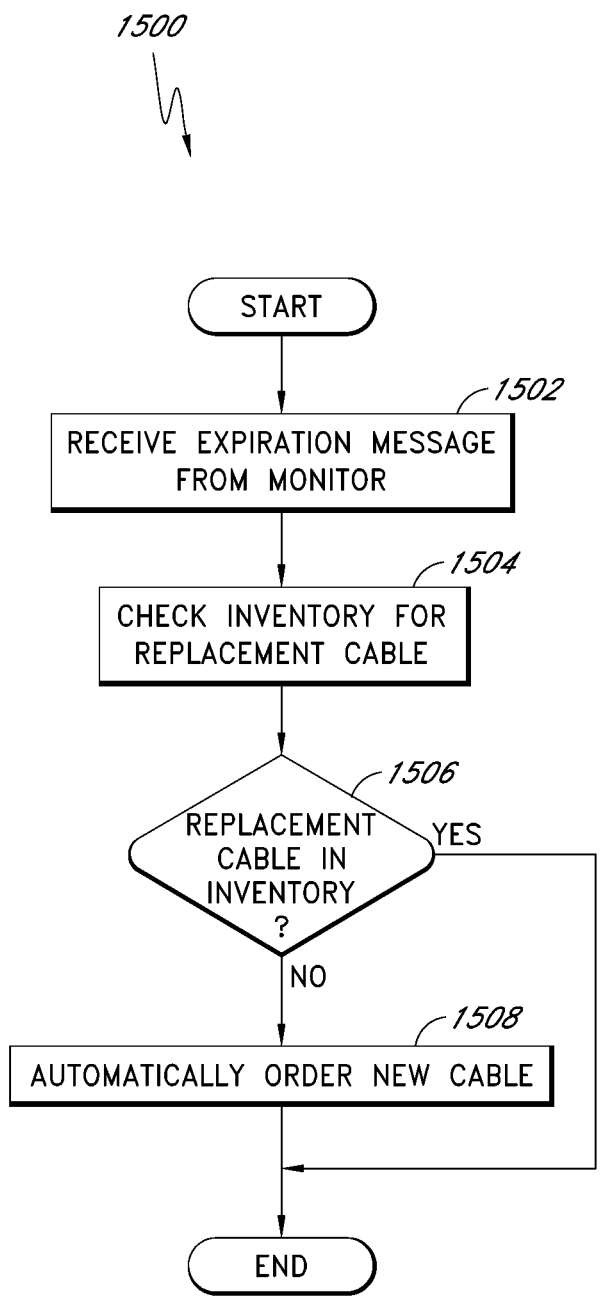

FIG. 15 illustrates an embodiment of a cable inventory method 1500 for controlling cable inventory. The cable inventory method 1500 may be performed by a server, such as the server 1038 described above. More generally, the cable inventory method 1500 may be implemented by a machine having one or more processors. In one embodiment, the method 1500 is performed in response to the method 1400 providing an expiration message at step 1408.

At block 1502, an expiration message is received from a monitor, indicating that a cable is close to expiration or has expired. At block 1504, an inventory is checked for a replacement cable. This inventory may be a hospital inventory, a record of which may be maintained in a hospital database or the like.

If it is determined at decision block 1506 that there is no replacement cable in the inventory, a new cable is ordered automatically to order a at block 1508. In an embodiment, this block 1508 is performed by electronically contacting a supplier to order the cable, for example, by sending a request over a network such as the Internet. Consequently, in certain embodiments, the cable inventory method 1500 enables the cable to be replaced preemptively, before cable failure. If, however, there is a replacement cable in inventory, the cable inventory method 1500 ends. However, in alternative embodiments, the cable inventory method 1500 orders a replacement cable regardless of the inventory, such that a predetermined level of cable inventory is maintained.

In additional embodiments, the cable inventory method 1500 may monitor sensor utilization, such as the number of sensors used during the patient's stay, the types of sensors, and the length of time in use before replacement. Such data can be used by the hospital to preemptively plan restocking and set department par inventory levels. In addition, a supplier can use this data to restock the hospital or implement a just-in-time program. Moreover, such information can be used by the supplier to improve overall cable reliability, and for the hospital to better plan and manage consumables.

Figure 16:
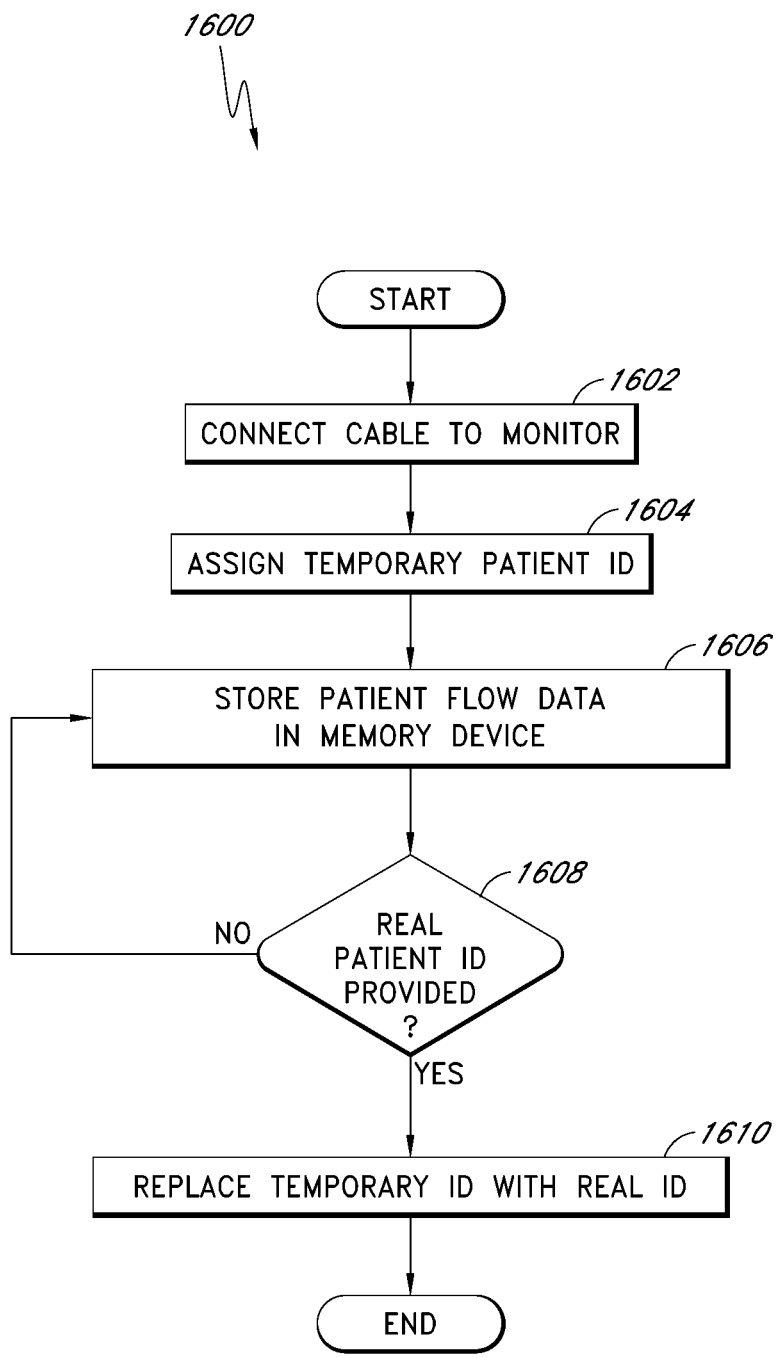
FIGS. 16 and 17 illustrate flowchart diagrams of example patient context management processes.

FIG. 16 illustrates an example context management method 1600 for managing patient context. In an embodiment, the context management method 1600 is performed by a physiological monitor, such as any of the monitors described above. More generally, certain blocks of the context management method 1600 may be implemented by a machine having one or more processors. The context management method 1600, in certain embodiments, advantageously enables a patient to be assigned a cable with a unique identifier upon the first connection of the cable to the patient or to a monitor.

At block 1600, a cable is connected to a monitor, for example, by a clinician such as a nurse. Thereafter, a temporary patient ID is assigned to the cable at block 1604. The temporary ID may be automatically assigned when power is provided to the information element in the cable, or a prompt may be provided to a clinician, who then assigns the ID. In addition, the temporary ID may also be previous stored on the cable. The temporary patient ID enables the cable to be identified as uniquely relating to the patient, prior to the patient's identification information being provided to the cable. The temporary patient ID may be stored in the information element of the cable.

At block 1606, patient flow data is stored in the information element. The patient flow data may include flow data described above with respect to FIG. 4. For example, the patient flow data may include information regarding connected devices, a department ID associated with the cable, and time spent by the cable in a department. By storing patient flow data, the context management method 1600 can enable the flow of the patient may be monitored upon connection of the cable to a monitor. Thus, even if the nurse neglects to identify the cable with the patient, the cable can have data indicating when it is being used on the same or a different patient.

At decision block 1608 it is determined whether a real patient ID has been provided. If so, then the temporary ID is replaced with the real patient ID at block 1610. The real patient ID may include any of the patient identification information described above, with respect to FIG. 4. If, however, it is determined that a real patient ID has not been provided, the context management method 1600 loops back to block 1606 to continue storing patient flow data in the information element.

Figure 17:
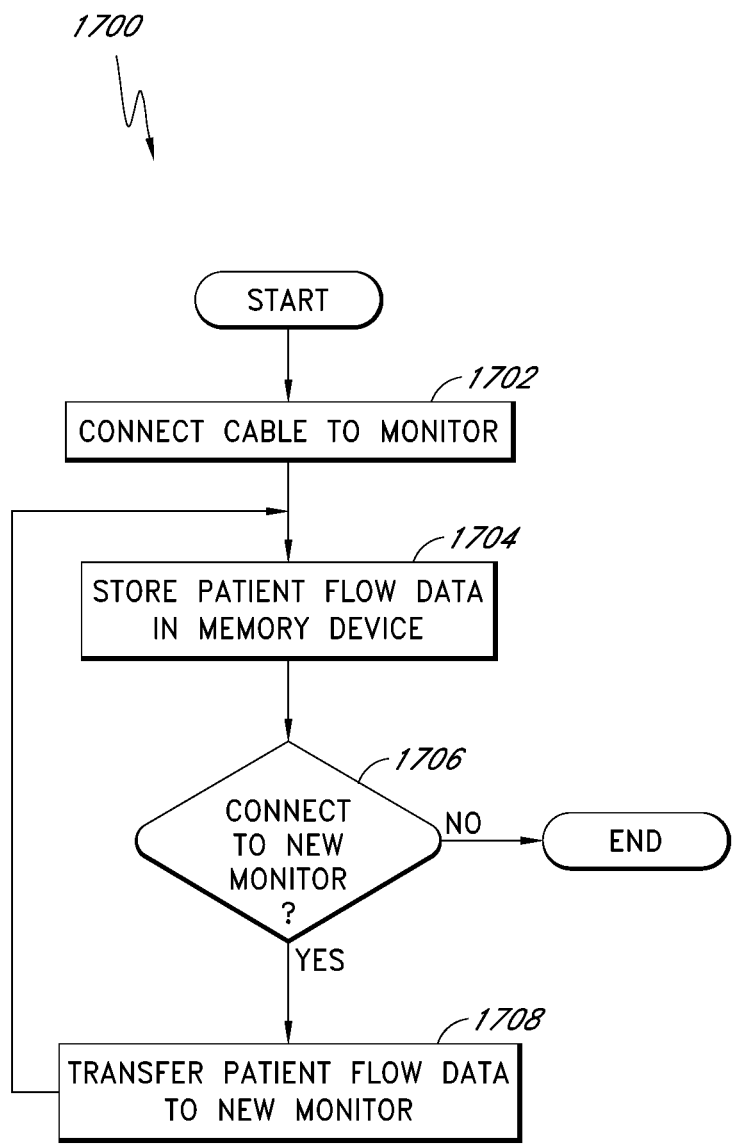

FIG. 17 illustrates another example context management method 1700 for managing patient context. In an embodiment, the context management method 1700 is performed by one or more monitors, such as any of the monitors described above. More generally, certain blocks of the context management method 1700 may be implemented by a machine having one or more processors.

At block 1702, a cable is connected to a monitor. In one embodiment, this block is performed by a clinician, such as a nurse. Patient flow data is then stored in an information element at block 1704. The patient flow data may include the flow data described above with respect to FIG. 4.

At decision block 1706, it is determined whether the cable has been connected to a new monitor. If it has, patient flow data is transferred from the cable to the new monitor at block 1708. In an embodiment, the new monitor determines whether the cable has been connected to the new monitor. Alternatively, the cable makes this determination. Transferring the patient flow data to the new monitor provides, in certain embodiments, the advantage of enabling the monitor to know where the patient has been in the hospital and for how long. If a new monitor has not been connected, the context management method 1700 ends.

Figure 18:
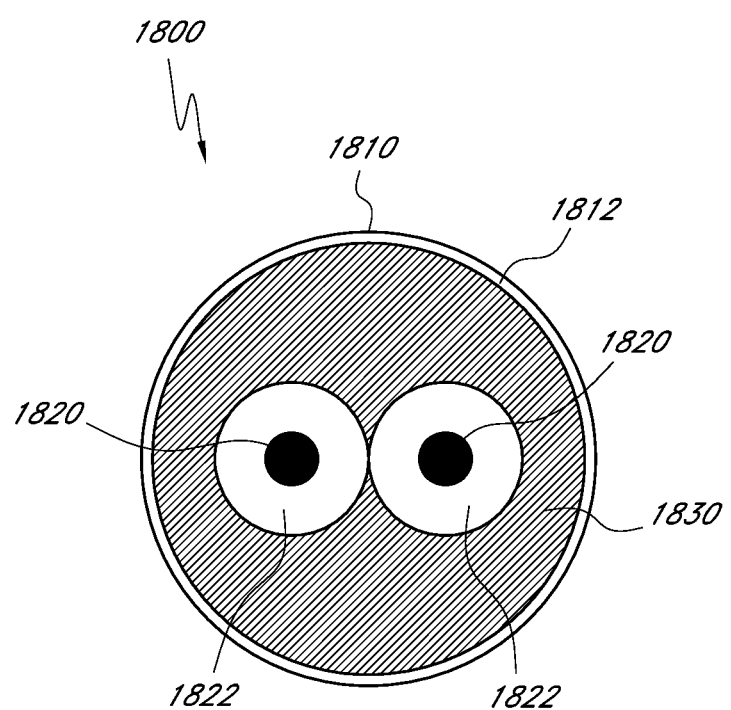
FIG. 18 illustrates an embodiment of a coextruded cable.

FIG. 18 illustrates a front elevation view of an embodiment of a coextruded cable 1800. The coextruded cable 1800 can be used as a cable or cable section in place of any of the cables mentioned herein. The coextruded cable 1800 can advantageously reduce noise due to a triboelectric effect.

Noise can adversely affect acoustic signals detected by any of the acoustic sensors described herein by corrupting a waveform detected by an acoustic or other sensor. Once source of noise is triboelectric noise, which can be present when a cable is squeezed, bringing conductors in the cable closer together. The closer the conductors are, the greater a capacitance can form between the conductors and/or between the conductors and shielding. This capacitance can be a source of triboelectric noise.

The example coextruded cable 1800 shown includes features that can reduce the amount of triboelectric noise generated by squeezing, rubbing, or other touching of the cable 1800. The cable 1800 includes an outer jacket 1810, which encompasses an outer shielding layer 1812. The outer shielding layer 1812 can reduce ambient noise from reaching conductors 1820 that extend through the cable 1800. Insulation 1822 surrounds each conductor 1820.

For ease of illustration, the coextruded cable 1800 is shown having two conductors 1820. However, the features of the coextruded cable 1800 can be extended to more than two conductors in certain embodiments. For example, more than two conductors can be surrounded by the insulation 1822, or each of two or more conductors can be individually surrounded by insulation. Further, a group of acoustic sensor-related conductors can be surrounded by insulation, and a group of optical sensor-related conductors can be surrounded by separate insulation.

Although not shown, the insulation 1822 can be shielded as well. Thus, in one embodiment, some or all acoustic sensor-related conductors can be shielded by a separate, inner shielding layer from the outer shielding layer 1812. Similarly, some or all optical sensor-related conductors can be shielding by a separate, inner shielding layer from the outer shielding layer 1812. One or both of the acoustic and optical sensor-related sets of conductors can include their own inner layer of shielding to reduce crosstalk between the acoustic and optical sensor-related conductors. Reducing crosstalk can be particularly beneficial for reducing noise on a communications line or lines in the cable 1800 (such as the serial transmission line 340 of FIGS. 3A, 3B).

Filling or substantially filling the space between the insulation 1822 and the shielding layer 1812 is a coextruded material 1830. The coextruded material 1830 can be conductive PVC or the like that reduces space between the conductors 1820, so that the cable 1800 does not compress the conductors 1822 together as easily. The cable 1800 can still be flexible or relatively flexible, however. Because the cable 1800 may compress less than other cables, less triboelectric noise may be generated. In addition, the conductive property of the conductive material 1830 can dissipate charge that builds up from the triboelectric capacitance occurring between the conductors 1820 and/or between the conductors 1820 and the shielding 1812. This dissipative property of the material 1830 can further reduce noise.

Moreover, in certain embodiments, the outer jacket 1810 of the cable 1800 can be coated or can be composed of a glossy material that has a reduced coefficient of friction. Accordingly, materials that rub, brush against, or otherwise contact the outer jacket 1810 can slide smoothly off, thereby further reducing triboelectric noise.

Many other configurations of the cable 1800 are possible. For example, in one embodiment, the cable 1600 can include a flexible or "flex" circuit having conductive traces disposed on a substrate. Acoustic and/or optical sensor-related conductors can be disposed in the flex circuit (or in separate flex circuits). Further, the decoupling circuitry described above can also be included in the flex circuit or circuits. The flex circuit can be used as a sensor cable (see above), an instrument cable (see above), as a hub cable (see below), portions of the same, or any combination of the same. Some examples of flex circuits that can be employed with any of the sensors, circuits, and cables described herein are described in U.S. Pat. No. 6,986,764, filed May 2, 2002, titled "Flex Circuit Shielded Optical Sensor," and U.S. Pat. No. 7,377,794, filed Mar. 1, 2006, titled "Multiple Wavelength Sensor Interconnect," the disclosures of which are both hereby incorporated by reference in their entirety.

Figure 19:
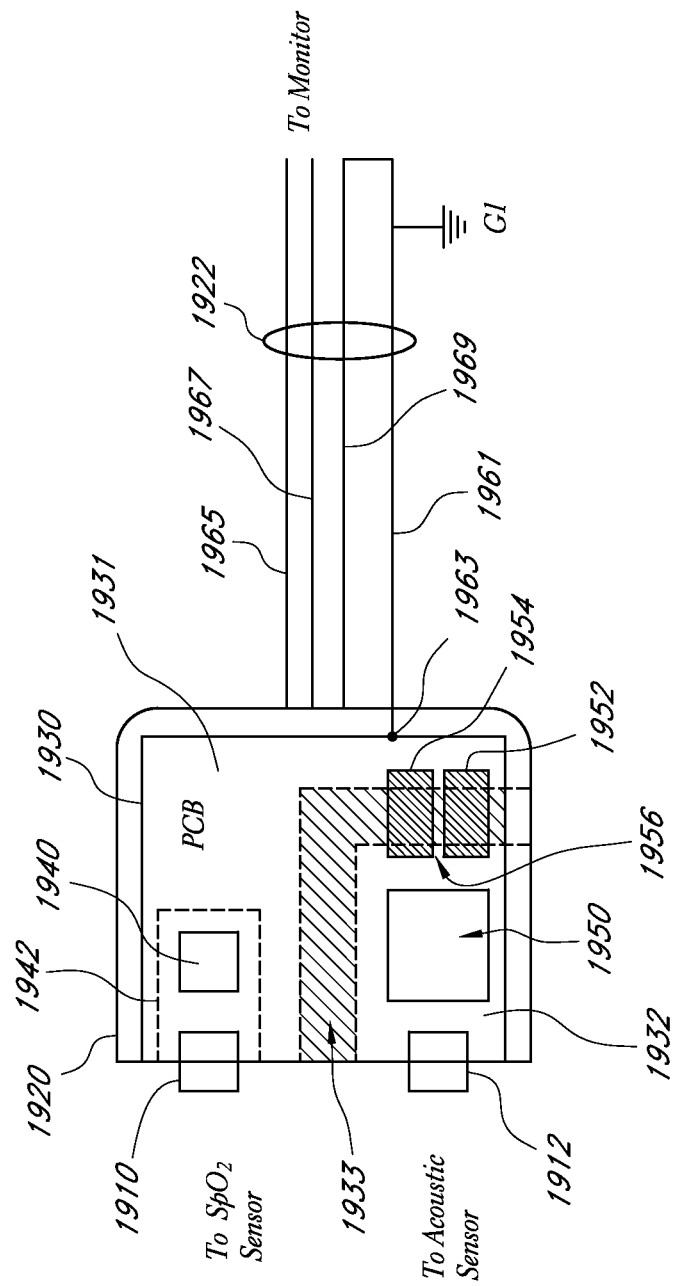
FIG. 19 illustrates an embodiment of a splitter cable.

FIG. 19 illustrates example internal components of an example hub 1920 or splitter cable. The hub 1920 shown is an example implementation of the hub 220 of FIG. 2 and can be used in place of any of the splitter cables described herein. Advantageously, in certain embodiments, the hub 1920 includes localized shielding 1942 to reduce the effects of electromagnetic noise on one or more physiological signals.

The hub 1920 includes connectors 1910, 1912 that connect to sensor or patient cables (see, e.g., FIG. 2). For purposes of illustration, the connector 1910 can be connected to an optical sensor via a cable, and the connector 1912 can be connected to an acoustic sensor via a cable. Other physiological sensors can be connected via cables to the connectors 1910, 1912.

The connectors 1910, 1912 can be soldered to a printed circuit board (PCB) 1930 housed within the hub 1920. The PCB 1930 includes front-end signal conditioning circuitry 1940, 1950, which can filter and condition optical signals and acoustic signals, respectively. The optical signal conditioning circuitry 1940 is disposed on a first area 1931 of the PCB 1930, and the acoustic signal conditioning circuitry 1950 is disposed on a second area 1932 of the PCB 1930. An electrical decoupling region 1933, which may be a nonconductive portion of the PCB 1930, separates the two areas 1931, 1932 of the PCB 1930 electrically. In other embodiments, the two areas 1931, 1932 are separate PCBs. For example, one of the areas 1931, 1932 can be a daughter board attachable to the other area.

Decoupling circuitry 1956 electrically decouples the two areas 1931, 1932. The decoupling circuitry 1956 can include any of the decoupling features described above. For example, the decoupling circuitry 1956 can include a transformer 1954 for decoupling power signals and an optocoupler 1952 for decoupling physiological signals. The decoupling circuitry 1956 is shown coupled to the acoustic signal conditioning circuitry 1950 in the depicted embodiment. In other embodiments, the decoupling circuitry 1956 is coupled with the optical signal conditioning circuitry 1940. Decoupling circuitry can also be applied separately to both the optical and acoustic signal conditioning circuitry 1940, 1950.

Due to regulations on winding insulation, to increase power efficiency of the transformer 1954, and possibly other factors, the transformer 1954 can be physically large relative to the size of other components in the hub 1920. As a result, the hub 1920 can be relatively large. The size of the hub 1920 can be reduced in certain embodiments by incorporating the decoupling circuitry in a patient monitor (not shown) attached to the hub 1920. However, if the hub 1920 is used with existing monitors that do not have decoupling circuitry, there may be little or no available space inside the monitor to fit a power-efficient transformer 1954. Thus, including the transformer 1954 in the hub 1920 can be advantageous to avoid making expensive modifications to an existing patient monitor.

A schematic view of a cable 1922 is also shown. The cable 1922 is attached to the hub 1920. The cable 1922 can be permanently attached to the hub 1920 or can be selectively detachable from the hub 1920. The cable 1922 includes various example conductors 1961, 1965, 1967, and 1969 in the depicted embodiment. Certain of the conductors 1961, 1965, 1967, and 1969 can be used for power transmission, signal acquisition, and grounding, among other potential uses.

One of the conductors 1969 is shown as a first ground (G1) and is electrically coupled with the optical signal conditioning circuitry 1940. Another of the conductors 1961 is shown as a second ground (G2) and is electrically coupled with the decoupling circuit 1952 (and, optionally, the decoupling circuit 1954 as well). The first and second grounds 1969, 1961 are therefore separated for optical and acoustic signals, respectively, in the depicted embodiment. Providing separate ground lines for the optical and acoustic signals can beneficially reduce crosstalk between these signals. The ground lines 1969, 1961 can be connected together at the end of the cable 1922 (e.g., in a monitor connector) or in a patient monitor (e.g., on a processing board).

To reduce noise, various components of the hub 1920 (e.g., including the PCB 1930) can be enclosed in an electromagnetic shield. The electromagnetic shield can be tied to ground conductors in the hub 1920, including the conductors 1961, 1969, and ground conductors in the acoustic signal conditioning circuitry 1950. However, doing so can cause the ground lines 1961, 1969 to come in electrical communication with both electrically-decoupled areas 1931, 1932 of the PCB 1930. As a result, patient isolation or decoupling would be broken, causing potentially unsafe conditions.

Advantageously, in certain embodiments, shielding can be provided locally within the hub 1920 instead of over all or substantially all of the components in the hub 1920. For instance, a local shield can enclose or at least partially enclose the acoustic circuitry 1950 and/or connector 1912. Alternatively, a local shield can enclose or at least partially enclose the optical circuitry 1940 and/or connector 1910. Advantageously, in certain embodiments, substantial noise-reduction benefit can be achieved by locally shielding one of the optical and acoustic circuitry 1940, 1950 with a local shield 1942. The local shield 1942 can beneficially shield solder joints of the connector 1910 and/or components 1940 as well. The shield can include a metal box, grate, perforated box, conductive glass, combinations of the same, or the like.

In other embodiments, a first local shield is disposed about the optical circuitry 1940 and a second local shield is disposed about the acoustic circuitry 1950. Each of these shields can be tied to different grounds or common potentials by virtue of the decoupling circuitry 1952, 1954.

Although the hub 1920 is illustrated with respect to optic and acoustic signals, more generally, the hub 1920 can interface with any type of physiological signals. Further, some or all of the features of the hub 1920 can be used in certain applications outside of the medical field where cables are joined together in a single hub. Moreover, the features of the hub 1920 can be extended to more than two sensor cables. Such a hub can optionally include decoupling circuitry for some or all of the sensor cables that interface with the hub.

In some embodiments, one or more of the steps are performed substantially in parallel, in an overlapping manner, or in another order. For example, some of the calibration information may change during operation (e.g., due to changes in operating temperatures and the like). In such situations, the process 1900 can periodically or continually perform steps 1904 and 1906 to obtain, and automatically adjust to, the most up to date calibration information, providing improved calibration and measurement accuracy. The process 1900 may further continually or periodically perform step 1902 (e.g., during processing), thereby detecting sensor path disconnection or changes during use.

Those of skill in the art will understand that information and signals can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

Those of skill will further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of this disclosure.

The various illustrative logical blocks, modules, and circuits described in connection with the embodiments disclosed herein can be implemented or performed with a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, processor, controller, microcontroller, state machine, etc. A processor can also be implemented as a combination of computing devices, e.g., a combination of a DSP and a microprocessor, a plurality of microprocessors, one or more microprocessors in conjunction with a DSP core, or any other such configuration. In addition, the term "processing" is a broad term meant to encompass several meanings including, for example, implementing program code, executing instructions, manipulating signals, filtering, performing arithmetic operations, and the like.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, a DVD, or any other form of storage medium known in the art. A computer-readable storage medium is coupled to the processor such that the processor can read information from, and write information to, the storage medium. In the alternative, the storage medium may be integral to the processor. The processor and the storage medium can reside in an ASIC. The ASIC can reside in a user terminal. In the alternative, the processor and the storage medium can reside as discrete components in a user terminal.

The modules can include, but are not limited to, any of the following: software or hardware components such as software object-oriented software components, class components and task components, processes, methods, functions, attributes, procedures, subroutines, segments of program code, drivers, firmware, microcode, circuitry, data, databases, data structures, tables, arrays, and/or variables.

In addition, although certain inventions have been disclosed in the context of certain embodiments, it will be understood by those skilled in the art that the inventions disclosed herein extend beyond the specifically disclosed embodiments to other alternative embodiments and/or uses of the inventions and obvious modifications and equivalents thereof. In particular, while the system and methods have been described in the context of certain embodiments, the skilled artisan will appreciate, in view of the present disclosure, that certain advantages, features and aspects of the acoustic signal processing system, device, and method may be realized in a variety of other applications and software systems. Additionally, it is contemplated that various aspects and features of the inventions disclosed herein can be practiced separately, combined together, or substituted for one another, and that a variety of combination and subcombinations of the features and aspects can be made and still fall within the scope of the inventions disclosed herein. Furthermore, the systems described above need not include all of the modules and functions described in certain embodiments. Thus, it is intended that the scope of the inventions disclosed herein disclosed should not be limited by the particular disclosed embodiments described above, but should be determined only by the claims that follow.

What is claimed is:

1. An acoustic physiological monitor for determining an acoustic physiological parameter of a medical patient with a multi-stage sensor assembly, the acoustic physiological monitor comprising:
a signal processor configured to receive a signal indicative of an acoustic physiological parameter of a medical patient from a multi-stage sensor assembly configured to be attached to the acoustic physiological monitor and the medical patient, the multi-stage sensor assembly including a plurality of stages, the plurality of stages including a first stage and a second stage; and
an information element query module configured to obtain calibration information from one or more information elements provided in each of the plurality of stages of the multi-stage sensor assembly, the calibration information including at least a first characteristic associated with a cable forming at least a part of the first stage and a process variable characteristic associated with an acoustic sensor forming at least a part of the second stage,
wherein the signal processor is further configured to:
in response to detecting attachment of the cable to the acoustic physiological monitor, adjust one or more signal processing parameters of the signal processor based on the first characteristic associated with the cable;
in response to detecting attachment of the acoustic sensor to the cable, further adjust the one or more signal processing parameters of the signal processor based on the process variable characteristic associated with the acoustic sensor;
based on the adjusted one or more signal processing parameters, generate a modified version of the signal representative of physiological sounds detected by the acoustic sensor; and
determine the acoustic physiological parameter of the medical patient based upon the modified version of the signal.

2. The physiological monitor of claim 1, wherein the signal processor is further configured to calculate an inverse of a transfer function associated with each stage of the multi-stage sensor assembly.

3. The physiological monitor of claim 2, wherein the signal processor is further configured to determine the physiological parameter of the medical patient based upon said signal, said calibration information, and said inverse of each of said transfer functions.

4. The physiological monitor of claim 1, wherein the plurality of stages comprises all of the stages of the multi-stage sensor assembly.

5. The physiological monitor of claim 1, wherein the signal processor compensates for variations in sensor assembly components by analyzing said calibration information.

6. The physiological monitor of claim 1, wherein said calibration information further includes a cut-off frequency associated with at least one of said plurality of stages.

7. The physiological monitor of claim 6, wherein said calibration information further includes a cut-off frequency associated with each of said plurality of stages.

8. The physiological monitor of claim 1, wherein said signal processor is further configured to automatically adjust the one or more signal processing parameters when a stage of said multi-stage sensor assembly is replaced.

9. The physiological monitor of claim 1, wherein said calibration information further includes process variable characteristics associated with at least one other stage of said plurality of stages.

10. The physiological monitor of claim 1, wherein said calibration information further includes a design variable characteristic of at least one stage of said plurality of stages.

11. The physiological monitor of claim 1, wherein said plurality of stages further includes second cable stage.

12. The physiological monitor of claim 1, wherein said plurality of stages further includes a splitter cable stage.

13. The physiological monitor of claim 1, further comprising a front end processor configured to condition the signal for processing by said signal processor, wherein said signal processor is further configured to determine the physiological parameter of the medical patient based upon calibration information associated with the front end processor.

14. The physiological monitor of claim 1, wherein said calibration information includes at least one of a sensitivity, a mechanical cut-in frequency, a mechanical cut-off frequency, a capacitance, a gain, an input impedance, an output impedance, a minimum saturation level, a resistance, a linear curve, a non-linear curve, a response, or a transfer function.

15. The physiological monitor of claim 1, wherein the information element query module is further configured to obtain authentication information from the information element.

16. The physiological monitor of claim 1, wherein the process variable characteristic associated with the acoustic sensor includes at least one of an acoustic sensitivity, an acoustic mechanical cut-in frequency, an acoustic mechanical cut-off frequency, a capacitance, a gain, an input impedance, an output impedance, a minimum saturation level, a resistance, a linear curve, a non-linear curve, a response, or a transfer function.

17. A method of determining an acoustic physiological parameter of a medical patient with an acoustic physiological monitor, comprising:

receiving a signal indicative of an acoustic physiological parameter of a medical patient from a multi-stage sensor assembly, the multi-stage sensor assembly including a plurality of stages, the plurality of stages including at least a cable corresponding to a first stage of the multi-stage sensor assembly and a first acoustic sensor corresponding to a second stage of the multi-stage sensor assembly;

obtaining calibration information from one or more information elements provided in each of the plurality of stages of the multi-stage sensor assembly, the calibration information including at least a first characteristic associated with the cable and a process variable characteristic associated with the first acoustic sensor;

in response to detecting attachment of the cable to the acoustic physiological monitor, adjusting one or more signal processing parameters of a signal processor based on the first characteristic associated with the cable;

in response to detecting attachment of the first acoustic sensor to the cable, further adjusting the one or more signal processing parameters of the signal processor based on the process variable characteristic associated with the first acoustic sensor;

based on the adjusted one or more signal processing parameters, generating a modified signal representative of physiological sounds detected by the first acoustic sensor;

determining the acoustic physiological parameter of the medical patient based upon the modified signal;

in response to detecting attachment of a second acoustic sensor to the cable, re-adjusting the one or more signal processing parameters of the signal processor based a the process variable characteristic associated with the second acoustic sensor, wherein the second acoustic sensor is of a same type as the first acoustic sensor and the second acoustic sensor replaces the first acoustic sensor; and based on the re-adjusted one or more signal processing parameters, generating a second modified signal representative of physiological sounds detected by the second acoustic sensor;

determining the acoustic physiological parameter of the medical patient based upon the second modified signal.

18. The method of claim 17, further comprising receiving authentication information associated with said plurality of stages.

19. The method of claim 17, wherein adjusting and/or re-adjusting one or more signal processing parameters comprises compensating for variations in sensor assembly components with said calibration information.

20. The method of claim 17, further comprising automatically adjusting the one or more signal processing parameters when a stage of said multi-stage sensor assembly is replaced.

21. The method of claim 17, wherein said determining the acoustic physiological parameter of the medical patient is also based upon calibration information associated with a front end processor of the physiological monitor.

22. The method of claim 17, wherein the process variable characteristic associated with the first acoustic sensor includes at least one of an acoustic sensitivity, an acoustic mechanical cut-in frequency, an acoustic mechanical cut-off frequency, a capacitance, a gain, an input impedance, an output impedance, a minimum saturation level, a resistance, a linear curve, a non-linear curve, a response, or a transfer function.

* * * * *

UNITED STATES PATENT AND TRADEMARK OFFICE
CERTIFICATE OF CORRECTION

PATENT NO. : 8,801,613 B2
APPLICATION NO. : 12/960325
DATED : August 12, 2014
INVENTOR(S) : Ammar Al-Ali et al.

Page 1 of 1

It is certified that error appears in the above-identified patent and that said Letters Patent is hereby corrected as shown below:

On the Title Page,

In column 2 (page 8, item 56) at line 50, Under Other Publications, change "Experieances," to --Experiences,--.

In column 2 (page 8, item 56) at line 75, Under Other Publications, change "Sheete," to --Sheet,--.

In column 2 (page 10, item 56) at line 12, Under Other Publications, change "Anaylsis" to --Analysis--.

In column 2 (page 10, item 56) at line 21, Under Other Publications, change "1244-125000110.1378" to --1244-1250 00110.1378--.

In the Specification,

In column 6 at lines 23-24, Change "carboxyhemologbin" to --carboxyhemoglobin--.

In column 10 at line 6, Change "EEPROM" to --EEPROM",--.

In column 11 at line 19, Change "The" to --the--.

In column 33 at line 6, Change "the this" to --the--.

In column 33 at line 41, Change "a at" to --at a--.

In the Claims,

In column 42 at line 5, In Claim 17, change "a" to --on--.

Signed and Sealed this
Seventeenth Day of March, 2015

Michelle K. Lee
*Director of the United States Patent and Trademark Office*